US011465989B2

(12) United States Patent
Kim et al.

(10) Patent No.: US 11,465,989 B2
(45) Date of Patent: Oct. 11, 2022

(54) GUANIDINE COMPOUNDS AND USE THEREOF

(71) Applicant: IMMUNOMET THERAPEUTICS INC., Houston, TX (US)

(72) Inventors: Sung Wuk Kim, Seongnam-si (KR); Hong Woo Kim, Daejeon (KR); Sang Hee Yoo, Daejeon (KR); Ji Sun Lee, Daejeon (KR); Hye Jin Heo, Daejeon (KR); Hong Bum Lee, Daejeon (KR); Ji Ae Kook, Daejeon (KR); Young Woo Lee, Daejeon (KR); Mi Jeong Kim, Seoul (KR); Woong Cho, Seongnam-si (KR)

(73) Assignee: ImmunoMet Therapeutics, Inc., Houston, TX (US)

( * ) Notice: Subject to any disclaimer, the term of this patent is extended or adjusted under 35 U.S.C. 154(b) by 0 days.

(21) Appl. No.: 15/304,798

(22) PCT Filed: Apr. 17, 2015

(86) PCT No.: PCT/KR2015/003884
§ 371 (c)(1),
(2) Date: Oct. 17, 2016

(87) PCT Pub. No.: WO2015/160220
PCT Pub. Date: Oct. 22, 2015

(65) Prior Publication Data
US 2017/0073331 A1    Mar. 16, 2017

(30) Foreign Application Priority Data

Apr. 17, 2014 (KR) .................. 10-2014-0046290
Jun. 27, 2014 (KR) .................. 10-2014-0080133
Oct. 2, 2014 (KR) .................. 10-2014-0133135

(51) Int. Cl.
*C07D 295/13*      (2006.01)
*C07D 213/38*      (2006.01)
(Continued)

(52) U.S. Cl.
CPC .......... *C07D 403/12* (2013.01); *C07C 279/04* (2013.01); *C07C 279/06* (2013.01); *C07C 279/08* (2013.01); *C07C 279/12* (2013.01); *C07C 279/16* (2013.01); *C07C 279/24* (2013.01); *C07C 279/26* (2013.01); *C07C 311/47* (2013.01); *C07C 311/49* (2013.01); *C07D 207/16* (2013.01); *C07D 209/40* (2013.01); *C07D 209/44* (2013.01); *C07D 211/14* (2013.01); *C07D 211/54* (2013.01); *C07D 213/38* (2013.01); *C07D 213/40* (2013.01); *C07D 233/88* (2013.01); *C07D 233/91* (2013.01); *C07D 239/42* (2013.01); *C07D 249/14* (2013.01); *C07D 251/18* (2013.01); *C07D 251/48* (2013.01); *C07D 263/48* (2013.01); *C07D 277/46* (2013.01); *C07D 295/13* (2013.01); *C07D 317/58* (2013.01); *C07D 319/18* (2013.01); *C07D 333/16* (2013.01); *C07D 333/20* (2013.01);
(Continued)

(58) Field of Classification Search
CPC .. C07D 295/13; C07D 213/40; C07D 213/38; C07D 319/18; C07D 209/40; C07D 209/44; C07D 233/88; C07D 233/91; C07D 317/58; C07D 333/20; C07D 333/16; C07D 277/46; C07D 211/14; C07D 211/54; C07D 239/42; C07D 251/18; C07D 251/48; C07D 249/14; C07D 207/16; C07D 263/48; C07D 403/12; A61P 35/00; A61P 35/04; A61P 3/00; A61P 3/10; A61P 3/04; A61P 21/00; A61P 43/00; A61P 3/06; A61P 1/16; A61P 9/00; A61P 5/50; A61P 19/10; A61P 15/00; C07C 2602/08; C07C 2602/10; C07C 279/16; C07C 279/26; C07C 279/24; C07C 279/12; C07C 279/04; C07C 279/06; C07C 279/08; C07C 311/49; C07C 311/47; C07C 2601/08; C07C 2601/02; C07C 2601/14; C07C 2601/04; C07C 2603/74
See application file for complete search history.

(56) References Cited

U.S. PATENT DOCUMENTS 2,631,152 A    3/1953   Ritter et al.
2,961,377 A    11/1960  Shapiro et al.
(Continued)

FOREIGN PATENT DOCUMENTS

CA    1072962 A     3/1980
CN    102725263 A   10/2012
(Continued)

OTHER PUBLICATIONS

Derivative, 2017, https://en.wikipedia.org/wiki/Derivative_(chemistry).*
(Continued)

*Primary Examiner* — Sun Jae Yoo
(74) *Attorney, Agent, or Firm* — Clark & Elbing LLP

(57) ABSTRACT

The present invention relates to guanidine compounds for inhibiting mitochondrial oxidative phosphorylation (OXPHOS) and use thereof. More specifically, the present invention relates to a pharmaceutical composition for preventing or treating a OXPHOS-related disease, particularly cancer, by inhibiting mitochondrial oxidative phosphorylation and reprogramming cellular metabolism.

6 Claims, 3 Drawing Sheets

(51) Int. Cl.

| | | |
|---|---|---|
| C07D 213/40 | (2006.01) | |
| C07D 333/20 | (2006.01) | |
| C07D 333/16 | (2006.01) | |
| C07D 249/14 | (2006.01) | |
| C07D 251/18 | (2006.01) | |
| C07D 251/48 | (2006.01) | |
| C07D 211/14 | (2006.01) | |
| C07D 211/54 | (2006.01) | |
| C07D 209/44 | (2006.01) | |
| C07D 209/40 | (2006.01) | |
| C07D 233/88 | (2006.01) | |
| C07D 233/91 | (2006.01) | |
| C07D 207/46 | (2006.01) | |
| C07D 279/08 | (2006.01) | |
| C07D 203/12 | (2006.01) | |
| C07D 239/42 | (2006.01) | |
| C07D 263/48 | (2006.01) | |
| C07D 319/18 | (2006.01) | |
| C07D 317/58 | (2006.01) | |
| C07D 277/46 | (2006.01) | |
| A61P 3/00 | (2006.01) | |
| A61P 3/04 | (2006.01) | |
| A61P 3/10 | (2006.01) | |
| A61P 3/06 | (2006.01) | |
| A61P 5/50 | (2006.01) | |
| A61P 13/00 | (2006.01) | |
| A61P 21/00 | (2006.01) | |
| A61P 35/00 | (2006.01) | |
| A61P 35/04 | (2006.01) | |
| A61P 9/00 | (2006.01) | |
| A61P 19/10 | (2006.01) | |
| A61P 1/16 | (2006.01) | |
| A61P 15/00 | (2006.01) | |
| C07C 279/16 | (2006.01) | |
| C07C 311/47 | (2006.01) | |
| C07C 311/49 | (2006.01) | |
| C07C 279/12 | (2006.01) | |
| C07C 279/26 | (2006.01) | |
| C07C 279/24 | (2006.01) | |
| C07C 279/08 | (2006.01) | |
| C07C 279/04 | (2006.01) | |
| C07C 279/06 | (2006.01) | |
| C07D 403/12 | (2006.01) | |
| C07D 207/16 | (2006.01) | |

(52) U.S. Cl.
CPC ...... *C07C 2601/02* (2017.05); *C07C 2601/04* (2017.05); *C07C 2601/08* (2017.05); *C07C 2601/14* (2017.05); *C07C 2602/08* (2017.05); *C07C 2602/10* (2017.05); *C07C 2603/74* (2017.05)

(56) References Cited

U.S. PATENT DOCUMENTS

| 3,170,925 A | 2/1965 | Doub |
|---|---|---|
| 3,270,036 A | 8/1966 | Bernstein et al. |
| 3,502,695 A | 3/1970 | Molho et al. |
| 3,531,499 A | 9/1970 | Beregi et al. |
| 3,960,949 A | 6/1976 | Ahrens et al. |
| 4,017,539 A | 4/1977 | Bosies et al. |
| 4,562,209 A | 12/1985 | Chou |
| 6,174,924 B1 | 1/2001 | Goldin et al. |
| 8,642,647 B2 | 2/2014 | Kim et al. |
| 8,648,111 B2 | 2/2014 | Kim et al. |
| 9,133,110 B2 | 9/2015 | Kim et al. |
| 2003/0187036 A1 | 10/2003 | Potier et al. |
| 2006/0100194 A1 | 5/2006 | Blackburn et al. |
| 2006/0127309 A1 | 6/2006 | Raffel et al. |
| 2009/0176773 A1 | 7/2009 | Klussmann et al. |
| 2010/0114898 A1 | 5/2010 | Wasserman et al. |
| 2010/0249108 A1 | 9/2010 | Tandon et al. |
| 2012/0283299 A1 | 11/2012 | Kim et al. |
| 2012/0309799 A1 | 12/2012 | Kim et al. |

FOREIGN PATENT DOCUMENTS

| CN | 102757285 A | 10/2012 |
|---|---|---|
| GB | 973882 A | 10/1964 |
| GB | 1040542 A | 9/1966 |
| JP | S51-6950 A | 1/1976 |
| JP | H9-509156 A | 9/1997 |
| JP | 2005-145973 A | 6/2005 |
| JP | 2008-540586 A | 11/2008 |
| JP | 4391422 B2 | 12/2009 |
| JP | 2012-526554 A | 11/2012 |
| JP | 2013-516461 A | 5/2013 |
| JP | 6487031 B2 | 3/2019 |
| KR | 10-2011-0081095 A | 7/2011 |
| KR | 20110081093 A | 7/2011 |
| KR | 10-2014-0108595 A | 9/2014 |
| WO | WO 95/20950 A1 | 8/1995 |
| WO | WO-99/18053 A1 | 4/1999 |
| WO | WO-01/91696 A2 | 12/2001 |
| WO | WO 02/02100 A1 | 1/2002 |
| WO | WO-2004/026241 A2 | 4/2004 |
| WO | WO-2009/113092 A2 | 9/2009 |
| WO | WO-2010/044581 A2 | 4/2010 |
| WO | WO-2010/044582 A2 | 4/2010 |
| WO | WO-2013103384 A1 | 7/2013 |
| WO | WO-2014/052305 A2 | 4/2014 |
| WO | WO-2015/026215 A1 | 2/2015 |

OTHER PUBLICATIONS

Bami et al., 1949, caplus an 1949:438987.*
Prodrug, 2017, https://en.wikipedia.org/wiki/Prodrug.*
Pierron, 1909, caplus an 1909:239.*
Augstein et al., 1965, caplus an 1965:424110.*
RN-1549479-60-8, registry file record, entry date Feb. 19, 2014.*
King et al., 1947, caplus an 1947:7917.*
RN-1551642-20-6, Feb. 20, 2014, registry index.*
Church et al., 1972, caplus abstract AN 1972:443232.*
Dawes et al., 1950, caplus abstract AN 1950:30912.*
RN 1548858-06-5, Feb. 18, 2014, registry index.*
Diamond et al., 1974, caplus an 1974:463361.*
Naranayan et al., 1970, caplus an 1970:12772.*
RN 1555309-48-2, registry compound, date Feb. 25, 2014.*
RN 13357-99-8, 1984, registry database compound.*
Ishikawa et al., 1993, caplus an 1993:516980.*
RN 1515513-59-3, Jan. 9, 2014, registry database compound.*
RN 1549257-77-3, registry database, Feb. 19, 2014.*
RN62658-42-8, registry database, Nov. 16, 1984.*
RN 59238-18-5, registry database compound, entry date Nov. 16, 1984.*
RN 55154-92-2, registry database compound, entry date Nov. 16, 1984.*
RN 1546065-93-3, registry database compound, date Feb. 16, 2014.*
RN4767-42-4, 1984, registry compound entry date Nov. 16, 1984.*
RN 1536705-60-8, 2014, registry database compound, entry date Feb. 4, 2014.*
RN 1542399-50-7, 2014, registry database compound, entry date Feb. 13, 2014.*
Dvornik et al., "The effect of some inhibitors of the postganglionic sympathetic mechanism on monoamine oxidase," Biochemical Pharmacology. 12(3):229-40 (1963).
First Office Action for Chinese Patent Application No. 2015800201535, dated Aug. 10, 2017 (28 pages) (English language translation provided).
Johnson et al., "Chemical sympathectomy by guanidinium adrenergic neuron blocking agents," Biochem Pharmacol. 28(9):1525-31 (1979).

(56) References Cited

OTHER PUBLICATIONS

Li et al., "Ligustrazine derivatives. Part 6: design, synthesis and evaluation of novel ligustrazinyl acylguanidine derivatives as potential cardiovascular agents," Med Chem. 8(5):928-33 (2012) (7 pages).
Malmquist et al., "Effects of adrenergic neuron-blocking guanidine derivatives on mitochondrial metabolism," Biochem Pharmacol. 17(9):1845-54 (1968).
Mayer et al., "An expedient and facile one-step synthesis of a biguanide library by microwave irradiation coupled with simple product filtration. Inhibitors of dihydrofolate reductase," J Comb Chem. 6(5)776-82 (2004).
Michel et al., "Influence sur les oxydophosphorylations des guanidines et biguanides dérivés de la 2-phényléthylamine, tyramine et 3,5-diiodotyramine," Comptes Rendus des Seances de la Societe de Biologie et de Ses Filiales. 163(7):1524-7 (1969).
Notice of Reasons for Rejection for Japanese Patent Application No. 2017-506240, dated Oct. 24, 2017 (7 pages).
Ozawa et al., "Effects of guanidine derivatives on the oxidative phosphorylation of rat liver mitochondria," Nihon Yakurigaku Zasshi. 64(2):21-8 (1968).
Schäfer et al., "Influence of electrostatic surface potential on mitochondrial ADP-phosphorylation," FEBS Lett. 59(1):48-51 (1975).
Schäfer, "Site-specific uncoupling and inhibition of oxidative phosphorylation by biguanides. II," Biochim Biophys Acta. 172(2):334-7 (1969).
Shapiro et al., "Hypoglycemic agents. III. 1-3 N1-Alkyl-and Aralkylbiguanides," J Am Chem Soc. 81(14):3728-36 (1959).
Vallin et al., "The effect of piericidin A on energy-linked processes in submitochondrial particles," Eur J Biochem. 5(3):402-8 (1968).
Yamamoto et al., "Protective effect of Na+ /H+ exchange inhibitor, SM-20550, on impaired mitochondrial respiratory function and mitochondrial Ca2+ overload in ischemic/reperfused rat hearts," J Cardiovasc Pharmacol. 39(4):569-75 (2002).
Extended European Search Report for European Patent Application No. 15780117.6, dated Apr. 20, 2017 (7 pages).
Second Office Action and Search Report with Translation for Chinese Patent Application No. 2015800201535, dated May 2, 2018 (27 pages).
Buzzai et al., "Systemic treatment with the antidiabetic drug metformin selectively impairs p53-deficient tumor cell growth," Cancer Res. 67(14):6745-6752 (2007).
Carrington et al., "Synthetic antimalarials. Part XLIX. The structure and synthesis of the dihydrotriazine metabolite of proguanil," J. Chem Soc. 1017-1031 (1954).
Chinese Office Action for CN Patent Application No. 201180005604. X, dated May 29, 2013 (13 pages).
Franklin, "The ammono carbonic acids," J Am Chem Soc. 44(3):486-509 (1922).
International Search Report dated Sep. 2, 2011 for International Patent Application No. PCT/KR2011/000098 (7 pages).
Paul et al., "Synthesis of biguanides as potential hypoglycaemic agents: part IV—structure-activity relationship," Indian J. Chem. 1: 218-220 (1963).
Notice of Preliminary Rejection for Korean Patent Application No. 10-2016-7032056, dated Nov. 6, 2017 (58 pages).
Communication pursuant to Article 94(3) EPC for European Patent Application No. 15780117.6, dated Aug. 9, 2018 (5 pages).
English Translation of Notice of Reasons for Rejection for Japanese Patent Application No. 2017-506240, dated Jul. 9, 2018 (4 pages).
Skowronska-Serafin et al., "Preparation of Derivatives of Amidineurea and Their Reactions," Tetrahedron. 10(1-2):12-25 (1960).
English Translation of Notice of Preliminary Rejection for South Korean Patent Application No. 10-2016-7032056, dated May 31, 2018 (18 pages).
Michel et al., "Influence sur les oxydophosphorylations des guanidines et biguanides dérivés de la 2-phényléthylamine, tyramine et 3,5-diiodotyramine," C R séances Soc Biol ses fil. 163(7):1524-7 (1969).

CAS RN: 1552485-06-9; STN entry date: Feb. 23, 2014; 1-Carbamimidamido-N-[2-(morpholin-4-yl)ethyl]methanimidamide (1 Page).
CAS RN: 1551042-67-1; STN entry date: Feb. 20, 2014; 1-Carbamimidamido-N-[2-(2,3-dihydro-1,4-benzodioxin-6-yl)ethyl]methanimidamide (1 Page).
CAS RN: 802873-61-6; STN entry date: Dec. 27, 2004; Imidodicarbonimidic diamide, N-(1,3-benzodioxol-5-ylmethyl)—(1 Page).
CAS RN: 737695-52-2; STN entry date: Sep. 2, 2004; Imidodicarbonimidic diamide, N-[2-(1-piperidinyl)ethyl]—(1 Page).
Notice of Preliminary Rejection for Korean Patent Application No. 10-2016-7032056, dated Dec. 28, 2018 (17 pages).
King et al., "Antiplasmodial Action and Chemical Constitution. Part VIII. Guanidines and Diguanides." J. Chem. Soc., 0:1063-1069 (1946).
Augstein et al., "Adrenergic Neurone Blocking Agents Derived from 1,4-Benzodioxan," J Med. Chem. 8(4):446-456 (1965).
Decision on Rejection and English Translation for Chinese Patent Application No. 2015800201535, dated Nov. 26, 2018 (12 pages).
Notice of Preliminary Rejection for Korean Patent Application No. 10-2016-7032056, dated May 30, 2019 (with English translation) (11 pages).
Saha et al., "Copper(II) Complexes with Schiff Bases Derived from O-Alkylamidinourea & Salicylaldehyde," Ind J Chem. 25A:340-44 (1986).
Yuan et al., "An Efficient Method for the Preparation of Amidinoureas," Tetrahedron Lett. 37(12):1945-48 (1996).
Ying et al., "A New Synthetic Approach to Carbamoylguanidinium Salts from N-Chloroguanidine and Aryl Isocyanates," Chinese J Chem. 23(4):448-53 (2005).
Kasetti et al., "Pharmacophoric features of drugs with guanylurea moiety: an electronic structure analysis," J Mol Model. 19(4):1865-74 (2013).
Gholivand et al., "Differential pulse voltammetric determination of metformin using copper-loaded activated charcoal modified electrode," Anal Biochem. 438(1):53-60 (2013).
Dukat et al., "The binding of arylguanidines at 5-HT(3) serotonin receptors: a structure—affinity investigation," Bioorg Med Chem Lett. 11(12):1599-1603 (2001).
Notice of Preliminary Rejection for Korean Patent Application No. 10-2013-0132381, dated Sep. 25, 2019 (with English translation) (28 pages).
Notice on Reexamination for Chinese Patent Application No. 201580020153.5, dated Jan. 16, 2020 (19 pages).
Alkalay et al., "Conversion of biguanides into substituted s-triazines assayable by GC or mass fragmentography," J Pharm Sci. 65(4):525-9 (1976).
CAS RN: 36397-25-8; STN entry date Nov. 16, 1984; Imidodicarbonimidic diamide, N-[3-(4-methoxyphenyl )propyl] (1 page).
CAS RN: 36397-26-9; STN entry date Nov. 16, 1984; Imidodicarbonimidic diamide, N-[3-(4-methoxyphenyl) propyl] (1 page).
CAS RN: 51023-64-4; STN entry date Nov. 16, 1984; Imidodicarbonimidic diamide, N-[(2-bromophenyl) methyl] (1 page).
Notice of Reasons for Rejection for Japanese Patent Application No. 2019-000435, dated Oct. 12, 2020 (13 pages) (English language translation provided).
Yen et al., "Response of "diabetic" mice (db/db) to p-fluorophenethylbiguanide," Pharmacol Res Commun. 9(1):39-47 (1977).
Petition for Trial for Korean Patent Application No. 10-2061390 dated Dec. 8, 2020 (97 pages).
Roberts et al., "The effects of biguanides on the reactions of thrombin and on the one-stage prothrombin time of standard human plasma," Ann N Y Acad Sci. 148(3):714-23 (1968).
Yuan P., et al., "Phenformin enhances the therapeutic benefit of $BRAF^{V600E}$ inhibition in melanoma", Proceedings of the National Academy of Sciences of the United States of America, Nov. 5, 2013, vol. 110, No. 45, pp. 18226-18231, USA.

(56) References Cited

OTHER PUBLICATIONS

Alexander Roesch, et al., "Overcoming intrinsic multi-drug resistance in melanoma by blocking the mitochondrial respiratory chain of slow-cycling JAROD1B$^{high}$ cells", Cancer Cell, Jun. 10, 2013, 23(6), pp. 811-825.
International Search Report in connection with PCT International Application No. PCT/KR2015/003884.
Written Opinion of the International Searching Authority in connection with PCT International Application No. PCT/KR2015/003884.

* cited by examiner

[FIG. 1]
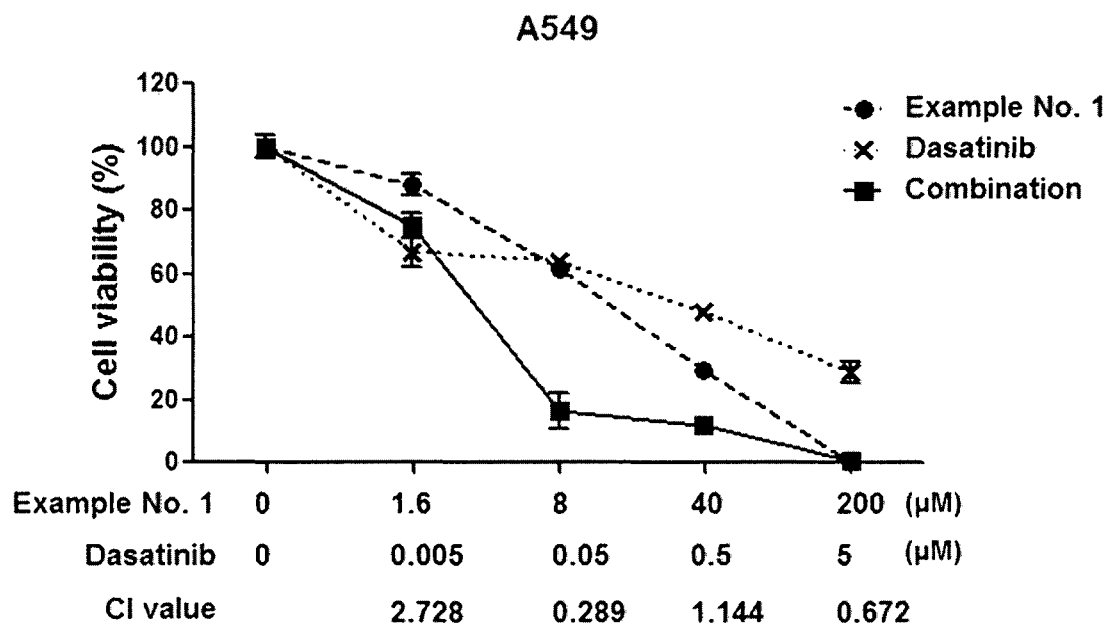
[FIG. 2]
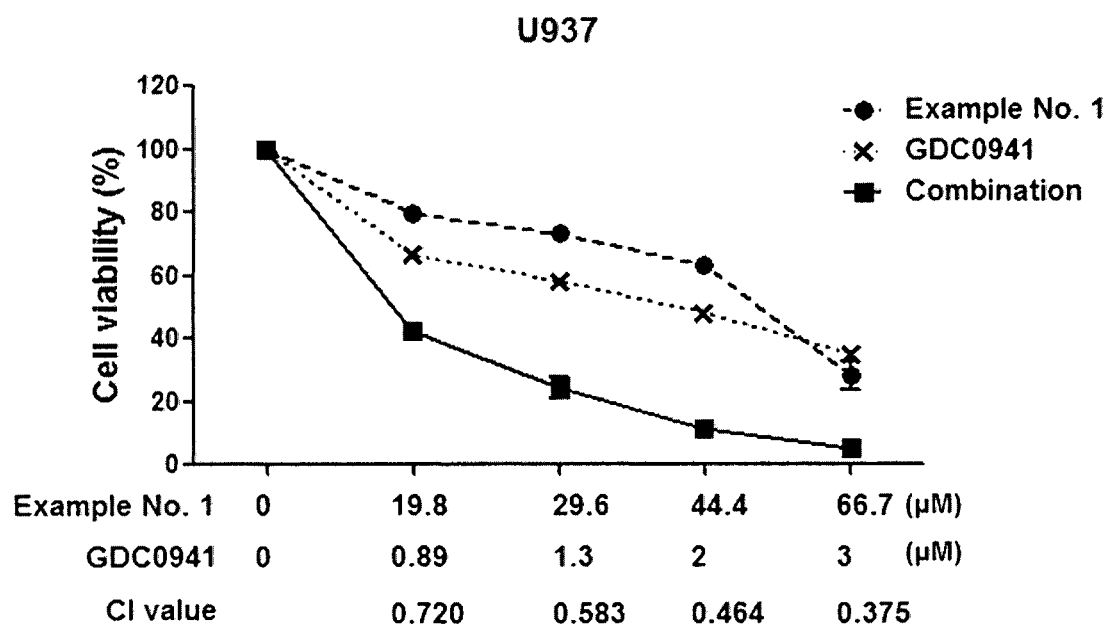

[FIG. 3]
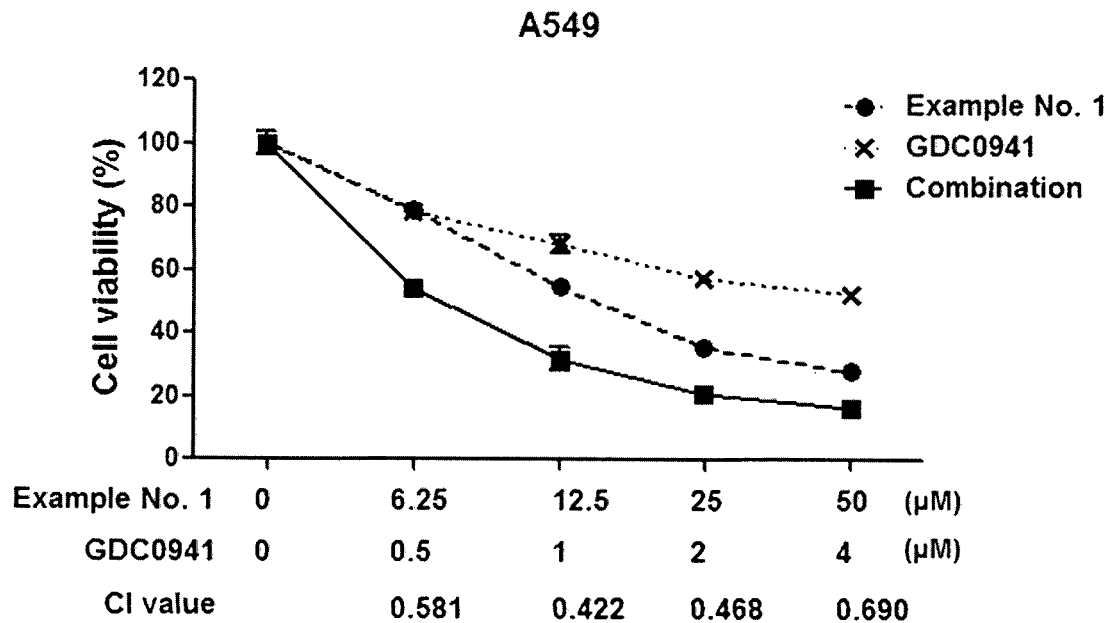
[FIG. 4]
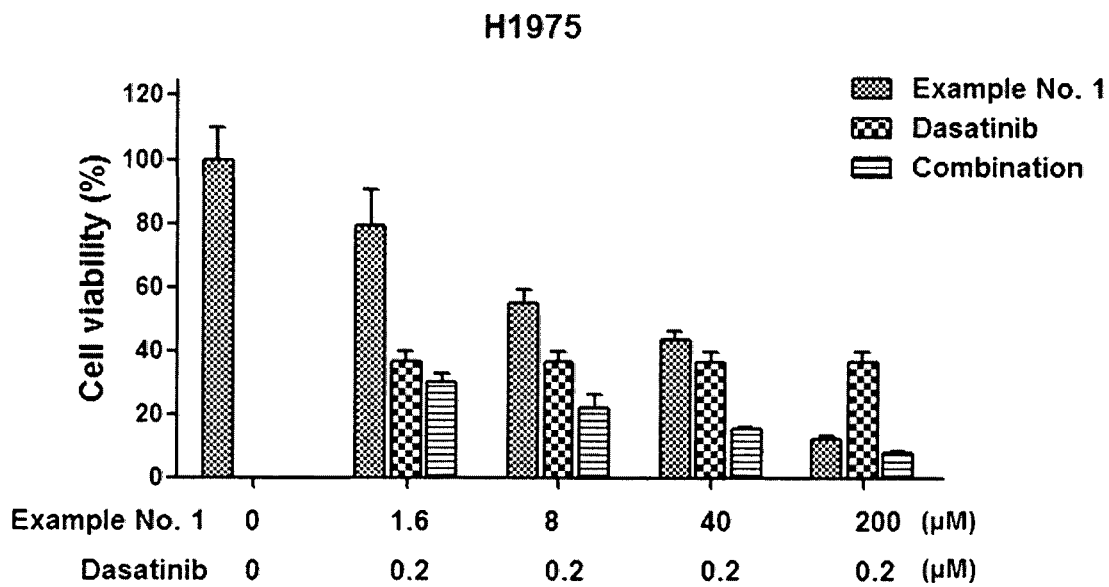

[FIG. 5]
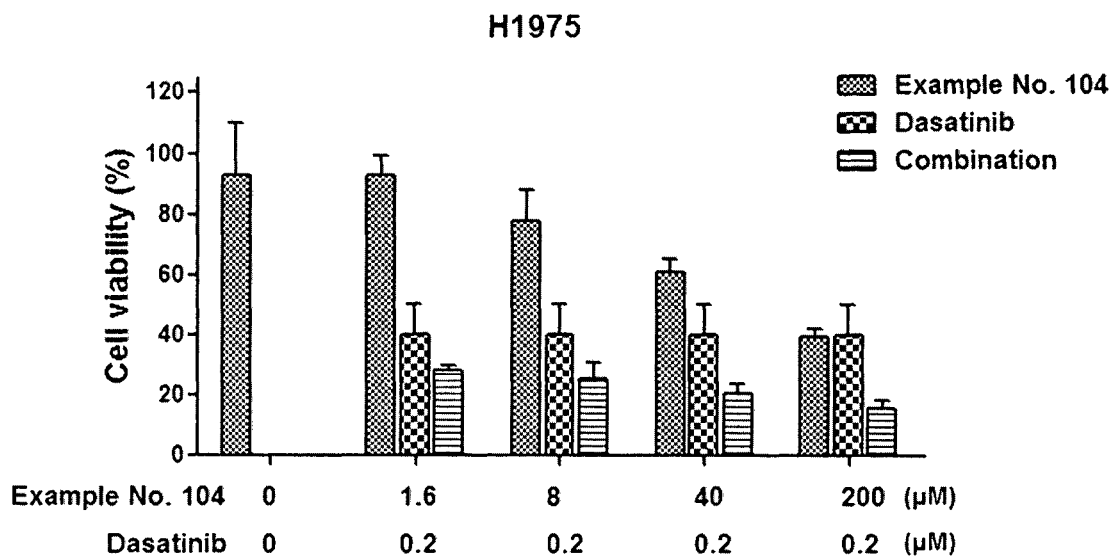
[FIG. 6]
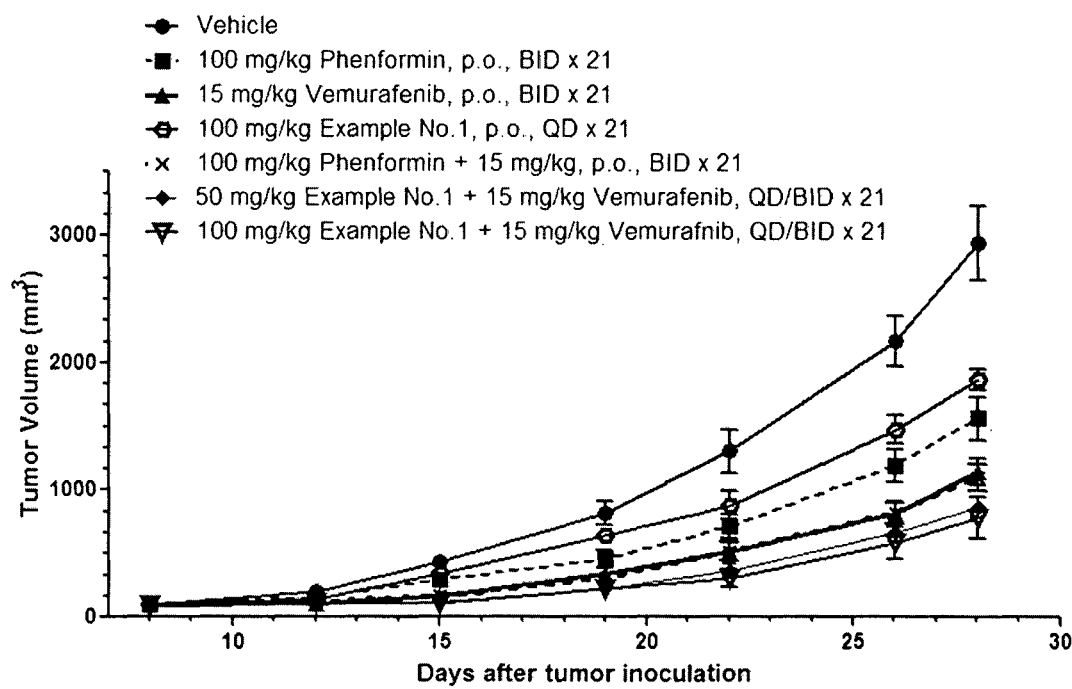

GUANIDINE COMPOUNDS AND USE THEREOF

CROSS-REFERENCE TO RELATED APPLICATIONS

This application is a § 371 national stage of PCT International Application No. PCT/KR2015/003864, filed Apr. 17, 2015, claiming priority of Korean Patent Applications Nos. KR 10-2014-0046290, filed Apr. 17, 2014, KR 10-2014-0080133, filed Jun. 27, 2014, and KR 10-2014-0133135, filed Oct. 2, 2014, the content of each of which is hereby incorporated by reference into the application.

TECHNICAL FIELD

The present invention relates to guanidine compounds for inhibiting mitochondrial oxidative phosphorylation (OXPHOS) and use thereof. More specifically, the present invention relates to a pharmaceutical composition for preventing or treating a disease associated with OXPHOS, particularly cancer by inhibiting mitochondrial oxidative phosphorylation and reprogramming cellular metabolism.

BACKGROUND ART

The cellular metabolism is essential to generate resources such as ATP and biomass for their growth. The metabolic pathway to generate ATP is glycolysis and OXPHOS in mitochondria. Normal cells generate ATP via OXPHOS in mitochondria since 38 ATP molecules are generated per glucose molecule. However fast growing cells use glycolysis to generate ATP and lactate is the final metabolite in the process. For a long time, the dependency on OXPHOS is thought to be determined by availability of oxygen because oxygen is the molecule that accepts electrons during OXPHOS. Recently, the studies have shown that oxygen is not the determinant for OXPHOS, but rather cellular demands for biomass and NADH/NADPH in fast growing cells actively choose to use glycolysis rather than OXPHOS. Cancer cells are the best example of transformed metabolism and uncontrolled proliferation. Dr. Otto Warburg in 1920s noticed the cancer cells mainly use glycolysis and produce high level of lactate. The highly glycolytic nature of cancer metabolism is currently named "Warburg effect". The glycolytic metabolic feature leads to a speculation that cancer cells might have dysfunctional mitochondria. Recent studies however showed the significance of OXPHOS in cancer cells, in particular, cancer stem cell-like population, migrating cancer cells, circulating cancer cells in metastasis.

Metformin is a biguanide used for the treatment of diabetes. It is known to be an OXPHOS inhibitor that has been clinically used for a long time. Several retrospective epidemiology studies pointed out that cancer incidence was lower in diabetic patients who were treated with metformin. The anticancer effect of metformin has been demonstrated in in vitro and in vivo models of breast, colon, prostate and lung cancer. The efficacy of metformin is limited by its weak potency and distribution due to the cationic property, therefore the dependency on Organic Cation Transporter 1 (OCT1) in order to enter cells. Many studies used a more potent biguanide and antidiabetic drug, phenformin to demonstrate the anticancer effect of OXPHOS inhibitor. Phenformin is more lipophilic than metformin and shows less dependency on OCT1 to enter cells. Several studies showed phenformin has activity of tumor growth inhibition and moreover prevent rising of cells resistant to targeted therapies (Yuan P, Proc Natl Acad Sci. 2013, 110(45): pp 18226-18231). Phenformin was shown to inhibit the growth of slow growing cancer cells or JARID1B$^{high}$ cells that might be responsible for drug resistance and relapse of disease (RoeschA, Cancer Cell, 2013, 23(6), pp 811-825) In the last decade, the main anticancer therapy was focused on development of inhibitors of oncogenes or signaling proteins such as kinases and growth factor receptors. The response rates were marginal in most cases. The initial responses by the best therapies apparently looked promising, but majority of patients relapsed with much more aggressive and drug resistant form of cancers. The true mechanism of relapse is still needed to be discovered, but multiple relapse mechanism have been reported such as secondary mutations on the same target or activation of different route of signaling pathway The mechanism of phenformin in overcoming drug resistance is not still clear. The OXPHOS inhibition may prevent further reprogramming after reprogramming upon co-treatment with targeted therapy, therefore it may cause energy crisis or prevent growth of slow growing population depending on OXPHOS.

Metformin has limited efficacy and tissue distribution and phenformin has been withdrawn from the market due to fatal safety issues. Thus, the conventional biguanide used for diabetic treatment have limitations as an anticancer agent.

DISCLOSURE

Technical Problem

The present invention relates to guanidine compounds or pharmaceutically-acceptable salts thereof with an improved activity of inhibiting mitochondrial oxidative phosphorylation (OXPHOS) and reprogramming cellular metabolism.

Another embodiment of the present invention is to provide a pharmaceutical composition for preventing or treating a disease-associated with mitochondrial oxidative phosphorylation (OXPHOS) or a method of preventing or treating a disease-associated with mitochondrial oxidative phosphorylation (OXPHOS) including administering the compound of the present invention to a subject in need.

Further embodiment of the present invention is to provide an anti-cancer pharmaceutical composition comprising the guanidine compounds or pharmaceutically-acceptable salts thereof as active ingredient.

Technical Solution

To achieve the technical object, an embodiment of the present invention relates to the guanide compounds, pharmaceutically acceptable salts, pharmaceutically acceptable solvates and prodrug derivatives which have superior inhibitory effect on cancer cell growth, cancer metastasis and cancer reoccurrence to conventional drugs, even though smaller amount of the compounds are used.

In addition, an embodiment of the present invention relates to a use of the guanidine compounds for inhibiting mitochondrial oxidative phosphorylation (OXPHOS) or reprogramming cellular metabolism.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing, wherein:

FIG. 1 shows the treatment effect of the Compound obtained in Example 1 in combination with Dasatinib on A549 cell.

FIG. 2 shows the treatment effect of the Compound obtained in Example 1 in combination with GDC0941 on U937 cell.

FIG. 3 shows the treatment effect of the Compound obtained in Example 1 in combination with GDC0941 on A549 cell.

FIG. 4 shows the treatment effect of the Compound obtained in Example 1 in combination with Dasatinib on H1975 cell.

FIG. 5 shows the treatment effect of the Compound obtained in Example 104 in combination with Dasatinib on H1975 cell.

FIG. 6 shows the treatment effect of the Compound obtained in Example 1 or Phenformin on Vemurafenib in xenograft model using SK-MEL-239 cell.

DETAILED DESCRIPTION OF THE INVENTION

Hereinafter, the present invention can be explained in more detail.

In further aspect, the present invention provides the compounds including the compounds having Chemical Formula 1 and Chemical Formula 6, pharmaceutically acceptable salts, pharmaceutically acceptable solvates and prodrug derivatives.

In another aspect, the present invention provides the compound selected from the group consisting of the guanidine compounds having Formula 1, pharmaceutically acceptable salts, pharmaceutically acceptable solvates and prodrug derivatives:

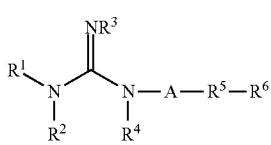

[Chemical formula 1]

Where, $R^1$ is H, $C_1$-$C_4$ alkyl or $C_1$-$C_4$ alkoxy, preferably H or $C_1$-$C_4$ alkyl, $R^2$, $R^3$ and $R^4$ are independently H or $C_1$-$C_4$ alkyl, A is a single bond or —C(NH)—NH—, —C(O)—, —C(NR$^7$)—, —C(O)NH— or —O—, —S—, where $R^7$ is H or $C_1$-$C_4$ alkyl, $R^5$ is a single bond or —(CH$_2$)n-, $R^6$ is at least one selected from the group consisting of $C_3$-$C_{10}$ cycloalkyl, 3 to 7-membered heterocycloalkyl, $C_6$-$C_{12}$ aryl group, 6 to 12-membered heteroaryl group, 7 to 11-membered benzocycloalkyl, and 7 to 11-membered benzoheterocycloalkyl, where cycloalkyl, heterocycloalkyl, aryl, heteroaryl, benzocycloalkyl, and benzoheterocycloalkyl can be substituted with at least one selected from the group consisting of hydrogen, hydroxyl group, halogen, $C_1$-$C_4$ alkyl, $C_1$-$C_4$ haloalkyl, $C_3$-$C_7$ cycloalkyl, $C_6$-$C_9$ arylalkyl, SO$_2$NH$_2$, OR$^8$ and NR$^{10}$R$^{11}$ where $R^8$, $R^{10}$ and $R^{11}$ are independently hydrogen, $C_1$-$C_4$ alkyl, $C_1$-$C_4$ haloalkyl, or $C_6$-$C_{12}$ aryl.

In an aspect, the present invention provides the compounds selected from the group consisting of the guanidine compounds having Formula 6, pharmaceutically acceptable salts, pharmaceutically acceptable solvates and prodrug derivatives:

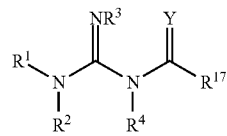

[Chemical Formula 6]

Where $R^1$ and $R^2$ are independently H, $C_1$-$C_4$ alkyl, $C_1$-$C_4$ alkoxy, or $C_6$-$C_{12}$ aryl; or are linked with an adjacent substituent to form 3 to 7-membered saturated or unsaturated cycloalkyl or heterocycloalkyl group, $R^3$ and $R^4$ are independently H or $C_1$-$C_4$ alkyl, Y is NH or O, and $R^{17}$ is —OR$^{18}$, —SR$^{19}$ or —NR$^{20}$R$^{21}$ where $R^{18}$, $R^{19}$, $R^{20}$ and $R^{21}$ are independently hydrogen, $C_1$-$C_4$ alkyl, $C_6$-$C_{12}$ aryl or $C_6$-$C_9$ arylalkyl, and $C_6$-$C_{12}$ aryl and $C_6$-$C_9$ arylalkyl can be substituted with at least one selected from the group consisting hydrogen, halogen, $C_1$-$C_4$ alkyl, $C_1$-$C_4$ alkoxy, C1-C4 haloalkyl, C1-C4 haloalkoxy, and C3-C7 cycloalkyl.

In further aspect, the present invention provides additional various compounds as well as the compounds having Chemical Formula 1 and Chemical Formula 6, pharmaceutically acceptable salts, pharmaceutically acceptable solvates and prodrug derivatives.

As used herein, the term "alkyl" refers to a saturated hydrocarbon group which is straight-chained or branched. Example groups include methyl, ethyl, propyl (n-propyl, isopropyl) and the like. The alkyl can be substituted with at least a halogen, such as F, Cl, Br or I and the example groups include CF$_3$, CHF$_2$, CH$_2$F, CH$_2$Cl, and the like.

As used herein, the term "arylalkyl" refers to an alkyl group that is substituted with an aryl group. Examples of arylalkyl groups include, but are not limited to, benzyl, phenethyl, benzhydryl, diphenylmethyl, triphenylmethyl, diphenylethyl, naphthylmethyl, etc.

As used herein, the terms "halo" or "halogen" includes fluoro, chloro, bromo, and iodo. As used herein, the term "alkoxy" is meant to refer to a functional group containing an "alkyl" group bonded to an oxygen atom. An "alkyl" is defined above. As used herein, the term "haloalkoxy" is meant to refer to a functional group containing "haloalkyl" group bonded to an oxygen atom. An "alkyl" is defined above.

As used herein, the term "cycloalkyl" refers to non-aromatic carbocycles including cyclized alkyl, alkenyl, and alkynyl groups. Cycloalkyl groups can include mono- or polycyclic ring systems, including spirocycles, or bridged cycles. Example cycloalkyl groups include cyclopropyl, cyclobutyl, cyclopentyl, cyclohexyl and cycloheptyl. $C_3$-$C_{10}$ cycloalkyl refers to a cycloalkyl radical containing from 3 to 10 ring carbon atoms. Examples of cycloalkyl groups include such groups as cyclopropyl, cyclobutyl, cyclopentyl, cyclohexl, cycloheptyl, cyclooctyl, pinenyl, and adamantanyl.

The term, "benzocycloalkyl" refers to moieties that have one or more aromatic rings fused to the cycloalkyl ring, and for examples, include benzo derivatives of cyclopropane, cyclobutane, cyclopentane, cyclohexane, and the like. The examples include indane, indene, and hydronaphthalene.

As used herein, the term "heterocycloalkyl" refers to a non-aromatic heterocycle where one or more of the ringforming atoms are heteroatom such as O, N, or S. Examples of heterocycloalkyl groups include pyrrolidinyl, pyrrolinyl, imidazolidinyl, imidazolinyl, pirazolidinyl, pirazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

The term, "benzohetrocycloalkyl" refers to moieties that have one or more aromatic rings fused to the heterocyoalkyl ring.

As used herein, the term "aryl" refers to a substituted or unsubstituted, mono- or bicyclic hydrocarbon aromatic ring system having 6 to 12 ring carbon atoms. Examples include unsubstituted or substituted phenyl and naphthyl groups.

As used herein, the term "heteroaryl" refers to an aromatic group containing 5 to 10 ring carbon atoms in which one or more ring carbon atoms are replaced by at least one hetero atom such as O, N, or S. Examples of heteroaryl groups include pyrrolyl, furanyl, thienyl, pirazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl.

The examples of the compounds having Chemical Formula 1 can be represented by Chemical Formula 2, when A is —C(NH)—NH—, $R^5$ is —$(CH_2)_n$—, and $R^1$, $R^2$, $R^3$, $R^4$ and $R^6$ are the same as defined in Chemical formula 1.

[Chemical formula 2]

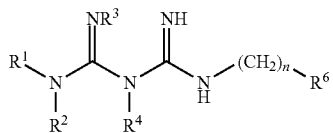

Where $R^1$ is H, $C_1$-$C_4$ alkyl or $C_1$-$C_4$ alkoxy, preferably H or $C_1$-$C_4$ alkyl $R^2$, $R^3$ and $R^4$ are independently H or $C_1$-$C_4$ alkyl, n is an integer of 1 to 6, preferably 1 to 3, and $R^6$ is at least one selected from the group consisting of $C_3$-$C_{10}$ cycloalkyl, 3 to 7-membered heterocycloalkyl, $C_6$-$C_{12}$ aryl group, 6 to 12-membered heteroaryl group, 7 to 11-membered benzocycloalkyl, and 7 to 11-membered benzoheterocycloalkyl, where cycloalkyl, heterocycloalkyl, aryl, heteroaryl, benzocycloalkyl, and benzoheterocycloalkyl can be substituted with at least one selected from the group consisting of hydrogen, hydroxyl group, halogen, $C_1$-$C_4$ alkyl, $C_1$-$C_4$ haloalkyl, $C_3$-$C_7$ cycloalkyl, $C_6$-$C_9$ arylalkyl, $SO_2NH_2$, $OR^8$ and $NR^{10}R^{11}$ where $R^8$, $R^{10}$ and $R^{11}$ are independently hydrogen, $C_1$-$C_4$ alkyl, $C_1$-$C_4$ haloalkyl, or $C_6$-$C_{12}$ aryl.

When $R^2$, $R^3$ and $R^4$ are hydrogen in Chemical formula 2, the compounds are represented by Chemical formula 2a:

[Chemical formula 2a]

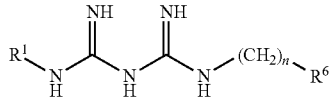

In the chemical formula 2a, $R^1$, n, and $R^6$ are the same as defined in Chemical formula 2.

In Chemical Formula 2, $R^6$ is at least one selected from the group consisting of $C_3$-$C_{10}$ cycloalkyl, 3 to 7-membered heterocycloalkyl, $C_6$-$C_{12}$ aryl group, 6 to 12-membered heteroaryl group, 7 to 11-membered benzocycloalkyl, and 7 to 11-membered benzoheterocycloalkyl. Thus, the examples of the compounds having Formula 2 can include (1) the compounds that $R^6$ is $C_6$-$C_{12}$ aryl group or 6 to 12-membered heteroaryl group; (2) the compounds that $R^6$ is $C_3$-$C_{10}$ cycloalkyl or 3 to 7-membered heterocycloalkyl; and (3) the compounds that $R^6$ is unsubstituted or substituted 7 to 11-membered benzocycloalkyl or 7 to 11-membered benzoheterocycloalkyl.

The examples of the compounds having Formula 2 can be represented by Formula 3:

[Chemical formula 3]

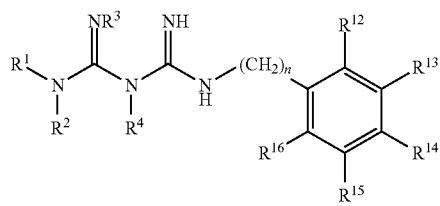

where $R^1$ is H, $C_1$-$C_4$ alkyl or $C_1$-$C_4$ alkoxy, preferably H or $C_1$-$C_4$ alkyl $R^2$, $R^3$ and $R^4$ are independently H or $C_1$-$C_4$ alkyl, n is an integer of 1 to 6, preferably 1 to 3, and $R^{12}$, $R^{13}$, $R^{14}$, $R^{15}$, and $R^{16}$ are independently at least one selected from the group consisting of hydrogen, hydroxyl group, halogen, $C_1$-$C_4$ alkyl, $C_1$-$C_4$ haloalkyl, $C_3$-$C_7$ cycloalkyl, $C_6$-$C_9$ arylalkyl, $SO_2NH_2$, $OR^8$ and $NR^{10}R^{11}$ where $R^8$, $R^{10}$ and $R^{11}$ are independently hydrogen, $C_1$-$C_4$ alkyl, $C_1$-$C_4$ haloalkyl, or $C_6$-$C_{12}$ aryl; or $R^{12}$, $R^{13}$, $R^{14}$, $R^{15}$, and $R^{16}$ are linked with an adjacent substituent to form 3 to 7-membered saturated or unsaturated cycloalkyl or heterocycloalkyl group.

When $R^2$, $R^3$ and $R^4$ are hydrogen in Chemical formula 3, the compounds are represented by Chemical formula 3a:

[Chemical formula 3a]

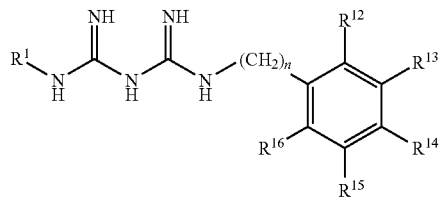

In the chemical formula 3a, $R^1$, $R^{12}$, $R^{13}$, $R^{14}$, $R^{15}$, $R^{16}$ and n are the same as defined in Chemical formula 3.

The examples of the compounds having Chemical Formula 1 can be represented by Chemical Formula 4, when A is a single bond and $R^5$ is —$(CH_2)_n$—.

[Chemical Formula 4]

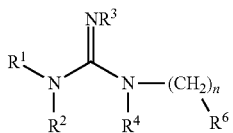

Where $R^1$ is H, $C_1$-$C_4$ alkyl or $C_1$-$C_4$ alkoxy, preferably H or $C_1$-$C_4$ alkyl $R^2$, $R^3$ and $R^4$ are independently H or $C_1$-$C_4$ alkyl, n is an integer of 1 to 6, preferably 1 to 3, and $R^6$ is at least one selected from the group consisting of $C_3$-$C_{10}$ cycloalkyl, 3 to 7-membered heterocycloalkyl, $C_6$-$C_{12}$ aryl group, 6 to 12-membered heteroaryl group, 7 to 11-membered benzocycloalkyl, and 7 to 11-membered benzoheterocycloalkyl, where cycloalkyl, heterocycloalkyl, aryl, heteroaryl, benzocycloalkyl, and benzoheterocycloalkyl can be substituted with at least one selected from the group consisting of hydrogen, hydroxyl group, halogen, $C_1$-$C_4$ alkyl, $C_1$-$C_4$ haloalkyl, $C_3$-$C_7$ cycloalkyl, $C_6$-$C_9$ arylalkyl, $SO_2NH_2$, $OR^8$ and $NR^{10}R^{11}$ where $R^8$, $R^{10}$ and $R^{11}$ are independently hydrogen, $C_1$-$C_4$ alkyl, $C_1$-$C_4$ haloalkyl, or $C_6$-$C_{12}$ aryl.

When $R^2$, $R^3$ and $R^4$ are hydrogen in Chemical formula 4, the compounds are represented by Chemical formula 4a:

[Chemical Formula 4a]

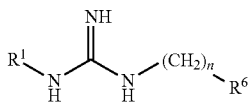

In the chemical formula 4a, $R^1$, $R^6$ and n are the same as defined in Chemical formula 4.

In Chemical Formula 4, $R^6$ is at least one selected from the group consisting of $C_3$-$C_{10}$ cycloalkyl, 3 to 7-membered heterocycloalkyl, $C_6$-$C_{12}$ aryl group, 6 to 12-membered heteroaryl group, 7 to 11-membered benzocycloalkyl, and 7 to 11-membered benzoheterocycloalkyl. Thus, the examples of the compounds having Formula 2 can include (1) the compounds that $R^6$ is $C_6$-$C_{12}$ aryl group or 6 to 12-membered heteroaryl group; (2) the compounds that $R^6$ is $C_3$-$C_{10}$ cycloalkyl or 3 to 7-membered heterocycloalkyl; and (3) the compounds that $R^6$ is unsubstituted or substituted 7 to 11-membered benzocycloalkyl or 7 to 11-membered benzoheterocycloalkyl.

The examples of the compounds having Formula 4 can be represented by Formula 5:

[Chemical Formula 5]

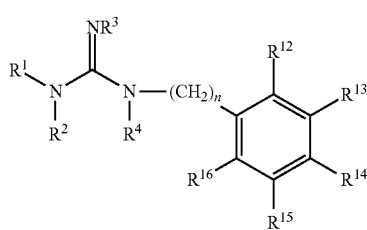

where $R^1$ is H, $C_1$-$C_4$ alkyl or $C_1$-$C_4$ alkoxy, preferably H or $C_1$-$C_4$ alkyl $R^2$, $R^3$ and $R^4$ are independently H or $C_1$-$C_4$ alkyl, n is an integer of 1 to 6, preferably 1 to 3, and $R^{12}$, $R^{13}$, $R^{14}$, $R^{15}$, and $R^{16}$ are independently at least one selected from the group consisting of hydrogen, hydroxyl group, halogen, $C_1$-$C_4$ alkyl, $C_1$-$C_4$ haloalkyl, $C_3$-$C_7$ cycloalkyl, $C_6$-$C_9$ arylalkyl, $SO_2NH_2$, and $OR^8$ where $R^8$ is hydrogen, $C_1$-$C_4$ alkyl, $C_1$-$C_4$ haloalkyl, or $C_6$-$C_{12}$ aryl; or $R^{12}$, $R^{13}$, $R^{14}$, $R^{15}$, and $R^{16}$ are linked with an adjacent substituent to form 3 to 7-membered saturated or unsaturated cycloalkyl or heterocycloalkyl group.

When $R^2$, $R^3$ and $R^4$ are hydrogen in Chemical formula 5, the compounds are represented by Chemical formula 5a:

[Chemical Formula 5a]

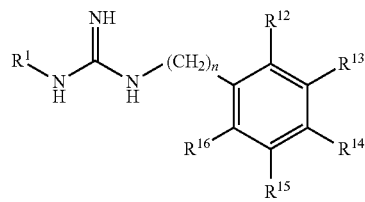

In the chemical formula 5a, $R^1$, $R^{12}$, $R^{13}$, $R^{14}$, $R^{15}$, $R^{16}$ and n are the same as defined in Chemical formula 5.

Another embodiment of the present invention includes the compounds having Chemical Formula 6:

[Chemical Formula 6]

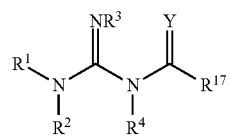

Where $R^1$ and $R^2$ are independently H, $C_1$-$C_4$ alkyl, $C_1$-$C_4$ alkoxy, or $C_6$-$C_{12}$ aryl; or are linked with an adjacent substituent to form 3 to 7-membered saturated or unsaturated cycloalkyl or heterocycloalkyl group, $R^3$ and $R^4$ are independently H or $C_1$-$C_4$ alkyl, Y is NH or O, and $R^{17}$ is —$OR^{18}$, —$SR^{19}$ or —$NR^{20}R^{21}$ where $R^{18}$, $R^{19}$, $R^{20}$ and $R^{21}$ are independently hydrogen, $C_1$-$C_4$ alkyl, $C_6$-$C_{12}$ aryl or $C_6$-$C_9$ arylalkyl, and $C_6$-$C_{12}$ aryl and $C_6$-$C_9$ arylalkyl can be substituted with at least one selected from the group consisting of hydrogen, halogen, $C_1$-$C_4$ alkyl, $C_1$-$C_4$ alkoxy, C1-C4 haloalkyl, C1-C4 haloalkoxy, and C3-C7 cycloalkyl.

When $R^3$ and $R^4$ are hydrogen in Chemical formula 6, the compounds are represented by Chemical formula 6a:

[Chemical Formula 6a]

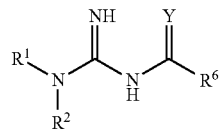

In the chemical formula 6a, $R^1$, $R^2$, Y and $R^6$ are the same as defined in Chemical formula 6.

In further aspect, the present invention provides additional various compounds as well as the compounds having Chemical Formula 1 and Chemical Formula 6, pharmaceutically acceptable salts, pharmaceutically acceptable solvates and prodrug derivatives. The examples of the present invention can include the following compounds:

N-1-(3,4-dichloro)phenethylbiguanide,

N-1-(2,5-dichloro)phenethylbiguanide,
N-1-(2-chloro)phenethylbiguanide,
N-1-(2,4-dichloro)phenethylbiguanide,
N-1-(3-fluoro)phenethylbiguanide,
N-1-(4-trifluoromethoxy)phenethylbiguanide,
N-1-(4-trifluoromethyl)phenethylbiguanide,
N-1-(3-methoxy)phenethylbiguanide,
N-1-(2-fluoro)phenethylbiguanide,
N-1-(4-methyl)phenethylbiguanide,
N-1-(4-methanesulphoneamine)phenethylbiguanide,
N-1-(4-(N,N-dimethyl)phenethylbiguanide,
N-1-(4-phenoxy)phenethylbiguanide,
N-1-(4-isopropyl)phenethylbiguanide,
N-1-(3,4-dimethyl)phenethylbiguanide,
N-1-(2,4-dimethyl)phenethylbiguanide,
N-1-(4-fluoro-2-methyl)phenethylbiguanide,
N-1-(2,4-dimethyl)benzylbiguanide,
N-1-(4-fluoro-3-methoxy)phenethylbiguanide,
N-1-(3,4-difluoro)phenethylbiguanide,
N-1-(2-morpholinoethyl)biguanide,
N-1-(2-methyl)phenethylbiguanide,
N-1-(3-bromo-4-fluoro)benzylbiguanide,
N-1-(2-fluoro-4-methyl)benzylbiguanide,
N-1-(2-(piperidin-1-yl)ethyl)biguanide,
N-1-(2-bromo)phenethylbiguanide,
N-1-(4-phenethyl)phenethylbiguanide,
N-1-(3,4-dimethyl)benzylbiguanide,
N-1-4-cyclopropylethylbiguanide,
N-1-(2-(5,6,7,8-tetrahydronaphthalen-1-yl)ethyl)biguanide,
N-1-(1-(2-naphthalene)methyl)biguanide,
N-1-2-cyclohexylethylbiguanide,
N-1-(2,4-dichloro)benzylbiguanide,
N-1-(2,3-dichloro)benzylbiguanide,
N-1-(benzo[d][1,3]dioxol-5-ylmethyl)biguanide
N-1-(2-chloro)benzylbiguanide,
N-1-(2,3-dichloro)benzylbiguanide,
N-1-(2-methyl)benzylbiguanide,
N-1-(2-bromo)benzylbiguanide,
N-1-(3-fluoro)benzylbiguanide,
N-1-(3-chloro)benzylbiguanide,
N-1-(2-fluoro)benzylbiguanide,
N-1-(2,6-difluoro)benzylbiguanide,
N-1-(2-(5,6,7,8-tetrahydronaphthalen-2-yl)ethyl)biguanide
N-1-(2-(naphthalen-1-yl)methyl)biguanide
N-1-(4-cyclopropyl-3-methyl)phenethylbiguanide,
N-1-(3-(4-cyclopropylphenyl)propyl)biguanide,
N-1-2-(5,6,7,8-tetrahydronaphthalen-2-yl)methanebiguanide,
N-1-(4-phenyl)benzylbiguanide,
N-1-(3-chloro-4-methyl)phenethylbiguanide,
N-1-(4-chloro-3-fluoro)phenethylbiguanide,
N-1-(3-chloro-4-fluoro)phenethylbiguanide,
N-1-tert-butyl-N-5-phenethylbiguanide,
N-1-tert-butyl-N-5-(3,4-dimethyl)benzylbiguanide,
N-1-(2-cyclopentyl)ethylbiguanide,
N-1-(4-phenoxy)benzylbiguanide,
N-1-isopropyl-N-5-(4-chloro)phenethylbiguanide,
N-1-isopropyl-N-5-phenethylbiguanide,
N-1-isopropyl-N-5-(4-chloro)benzylbiguanide,
N-1-isopropyl-N-5-(3,4-dimethyl)phenethylbiguanide,
N-1-(4-chloro-3-methyl)phenethylbiguanide,
N-1-(1-adamantyl)methylbiguanide,
N-1-tert-butyl-N-5-(3,4-dichloro)benzylbiguanide,
N-1-tert-butyl-N-5-(2-methyl)benzylbiguanide,
N-1-(1-cyclohexyl)methylbiguanide,
N-1-2-(2,3-dihydro-1H-inden-5-yl)ethylbiguanide,
N-1-tert-butyl-N-5-(2-(5,6,7,8-tetrahydronaphthalen-2-yl)methane)biguanide,
N-1-(4-bromo-3-methyl)benzylbiguanide,
N-1-(2-(2,3-dihydrobenzo[b][1,4]dioxin-6-yl)ethyl)biguanide,
N-1-(3,4-dibromo)phenethylbiguanide,
N-1-(4-iodo)phenethylbiguanide,
N-1-(4-iodo-3-bromo)phenethylbiguanide,
N-1-(4-bromo-3-chloro)phenethylbiguanide,
N-1-(3-iodo-4-chloro)phenethylbiguanide,
N-1-(3-iodo-4-bromo)phenethylbiguanide,
N-1-(3-bromo-4-chloro)phenethylbiguanide,
N-1-(4-iodo-3-methoxy)phenethylbiguanide,
N-1-(3-chloro-4-iodo)phenethylbiguanide,
N-1-(2-methoxy-4-iodo)phenethylbiguanide,
N-1-(2-methoxy-4-chloro)phenethylbiguanide,
N-1-(2-methoxy-4-bromo)phenethylbiguanide,
N-1-2-(thiophen-2-ylmethyl)biguanide,
N-1-(3,4-difluoro)benzylbiguanide,
N-1-(3-phenylpropyl)biguanide,
N-1-(4-fluoro-2-methyl)benzylbiguanide,
N-1-(3-fluoro-4-methyl)benzylbiguanide,
N-1-(2,4,6-trifluoro)benzylbiguanide,
N-1-(4-methyl)benzylbiguanide,
N-1-(4-hydroxy-2-fluoro)benzylbiguanide,
N-1-(4-fluoro)phenylpropylbiguanide,
N-1-(4-methoxy)phenylpropylbiguanide,
N-1-(2-iodo)benzylbiguanide,
N-1-(3-iodo)benzylbiguanide,
N-1-(4-fluoro)phenethyl-N-5-dimethylbiguanide,
N-1-(2-phenyl)propane-N-5-dimethylbiguanide,
N-1-phenethyl-N-5-dimethylbiguanide,
N-1-(2-phenylprophyl)biguanide,
N-1-phenethyl-1-methyl-N-5-dimethylbiguanide,
N-1-(4-fluoro)phenethyl-1-methyl-biguanide,
N-1-(4-fluoro)phenethyl-N-1-methyl-N-5-dimethylbiguanide,
N-1-methyl-N-1-(4-methoxy)phenethylbiguanide,
N-1-(4-methoxy)phenethyl-1-methyl-N-5-dimethylbiguanide,
N-1-(4-methoxy)phenethyl-N-5-dimethylbiguanide,
N-1-(4-fluoro)phenethylbiguanide,
N-1-methyl-N-1-phenethylbiguanide,
N-1-(4-methoxy)phenethylbiguanide,
N-1-phenethyl-N-2-methylbiguanide,
N-1-(2-(thiophen-2-yl)ethyl)-N-2-methylbiguanide,
N-1-(2-(benzo[d][1,3]dioxol-5-yl)ethyl)-N-2-methylbiguanide,
N-1-(2-(benzo[d][1,3]dioxol-5-yl)ethyl)-N-2-butylbiguanide,
N-1-(4-trifluoromethoxy)phenethyl-N-2-methylbiguanide,
N-1-(4-trifluoromethoxy)phenethyl-N-2-butylbiguanide,
N-1-(4-trifluoromethyl)phenethyl-N-2-methylbiguanide,
N-1-(4-trifluoromethyl)phenethyl-N-2-butylbiguanide,
N-1-phenethyl-N-1-methyl-N-2-methylbiguanide,
N-1-phenethyl-N-1-methyl-N-2-methyl-N-5-dimethylbiguanide,
N-1-phenethyl-N-2-methyl-N-5-dimethylbiguanide,
N2,N4-diphenethyl-1,3,5-triazine-2,4-diamine
N2-phenethyl-1,3,5-triazine-2,4-diamine
N3-phenethyl-4H-1,2,4-triazole-3,5-diamine
N3-(3,4-dichlorophenethyl)-4H-1,2,4-triazole-3,5-diamine
N-1-(3,4-dichloro)phenethyl-N5-methylbiguanide,
N-1-methyl-N-5-benzylbiguanide,
N-1-methyl-N-5-phenethylbiguanide,
N-1-cyclohexyl-N-5-benzylbiguanide, N-1-methyl-N-5-(2-(5,6,7,8-tetrahydronaphthalen-2-yl)ethyl)biguanide
N-1-propyl-N-5-(2-(5,6,7,8-tetrahydronaphthalen-2-yl)ethyl)biguanide
N-1-propyl-N-5-(3,4-dichloro)phenethylbiguanide,
N-1-methoxy-N-5-(3,4-dichloro)phenethylbiguanide,
N-1-methyl-N-5-(4-methyl)benzylbiguanide,
4-methylsulfonyl-N—(N-(4-(trifluoromethoxy)phenyl)carbamimidoyl)piperidine-1-carboximidamide,
N-1-methyl-N-2-methyl-N-5-(3,4-dichloro)phenethylbiguanide,
1-(3,4-dimethylphenethyl)guanide,
1-(phenethyl)guanide,
1-(4-trifluoromethoxyphenethyl)guanide,
isoindolin-2-carboimidamide,
1-(2,3-dihydro-1H-inden-2-yl)guanide,
1-(4-methylphenethyl)guanide,
1-(2-chlorophenethyl)guanide,
1-(3,4-dichlorophenethyl)guanide,
1-(4-fluorophenethyl)guanide,
1-(2-fluorophenethyl)guanide,
1-(thiopen-2-yl-ethyl)guanide
1-(thiopen-2-yl-methyl)guanide,
1-(1,3-benzodioxol-5-ylmethyl)guanide
1-(1,3-benzodioxol-5-ylethyl)guanide
1-(4-phenoxyphenethyl)guanide,
1-(4-isopropylphenethyl)guanide,
1-(benzyloxy)guanide
1-(3,4-dichlorobenzyl)guanide,
1-(4-methylbenzyl)guanide,
1-(4-methoxy-3-trifluoromethylbenzyl)guanide,
1-(2,4,6,-trifluorobenzyl)guanide,
1-(3,4-difluorobenzyl)guanide,
1-(2,4-dimethylphenethyl)guanide,
1-(thiophen-2-ylmethoxy)guanide
1-(benzo[d][1,3]dioxol-5-ylmethoxy)guanide
1-(2-(5-methyl-2-nitro-1H-imidazol-1-yl)ethyl)guanide,
1-(perfluorophenethyl)guanide,
1-(2-chlorobenzyl)guanide,
1-(2-methylphenethyl)guanide,
1-(2-(pyridin-2-yl)ethyl)guanide,
1-(2-(pyridin-3-yl)ethyl)guanide,
3-phenylpropanimidamide
1-(3-phenylpropyl)guanide,
1-(2-methylbenzyl)guanide,
1-(4-(aminomethyl)benzyl)guanide sulphate
1-(4-fluoro-2-methylbenzyl)guanide
1-(4-fluoro-2-methylphenethyl)guanide
1-(3-fluoro-4-methylbenzyl)guanide,
1-(2,4-dimethylbenzyl)guanide,
1-(3,4-difluorophenethyl)guanide,
1-(2-morpholinoethyl)guanide,
1-(4-fluorophenethyl)-1-methyl guanide,
(S)-1-(2-phenylpropyl)guanide,
1-(2-fluoro-4-hydroxybenzyl)guanide,
1-(2-bromobenzyl)guanide,
1-(3-fluorophenethyl)guanide,
1-(3-bromo-4-fluorobenzyl)guanide,
1-(2-fluoro-4-methylbenzyl)guanide,
1-(2-(piperidin-1-yl)ethyl)guanide,
1-(4-cyclopropylphenethyl)guanide,
1-(2-(5,6,7,8-tetrahydronaphthalen-2-yl)ethyl)guanide,
1-(4-bromobenzyl)guanide,
1-(3-(4-methoxyphenyl)propyl)guanide,
1-(4-fluoro-2-methylbenzyl)-1-methyl guanide,
1-(4-phenethylphenethyl)guanide,
1-methyl-1-(3-phenylpropyl)guanide,
5-phenylpyrimidine-2-amine,
1-(2-cyclopropylethyl)guanide,
1-(4-cyclopropyl-2-fluorophenethyl)guanide,
1-(1-(5,6,7,8-tetrahydronaphthalene-1-yl)ethyl)guanide,
1-methyl-1-((5,6,7,8-tetrahydronaphthalene-1-yl)methyl)guanide,
1-(2-cyclobutylethyl)guanide,
1-(4-phenylphenethyl)guanide,
1-(naphthalen-1-ylmethyl)guanide
1-(2-cyclohexylethyl)guanide,
1-(naphthalen-2-ylmethyl)guanide
1-((5,6,7,8-tetrahydronaphthalen-2-yl)methyl)guanide
N-(4-phenyl)benzyl guanide,
1-(2-(1,2,3,4-tetrahydronaphthalen-2-yl)ethyl) guanide,
1-(1-adamantylmethyl) guanide,
1-(4-phenoxybenzyl) guanide,
1-(2-cyclopentylethyl) guanide,
1-(1-cyclohexylmethyl) guanide,
1-(4-chloro-3-methyl)phenthyl guanide,
1-(4-chloro-3-methylphenthyl) guanide,
1-(4-bromo-3-methylbenzyl) guanide,
1-(4-bromo-3-chlorophenethyl) guanide,
phenethylamino(dimethyl-1-yl)methylcarbamidate,
3-(benzyl formimidate)-1,1-dimethyl guanide,
3-(phenethyl formimidate)-1,1-dimethyl guanide
3-(propyl formimidate)-1,1-dimethyl guanide,
butylimino(pyrrolidin-1-yl)methylcarbamimidate
phenethyl imino(pyrolidin-1-yl)methylcarbamidate,
benzylimino(pyrolidin-1-yl)methylcarbamidothioate,
4-fluorophenethyl imino(pyrolidin-1-yl)methylcarbamidate
1-(4-fluorophenethyl formimidate)guanide
1-(phenethyl formimidate)guanide 1-(butyl formimidate)guanide,
1-(benzyl formimidate)guanide,
1-(butyl formimidate)-3-(2-(benzo[d][1,3]dioxol-5-yl)ethyl) guanide
1-(phenethyl formimidate)-3-(2-(benzo[d][1,3]dioxol-5-yl)ethyl) guanide
N-1-(N-dimethylaminosulphonyl)-N3-phenethyl guanide,
N-1-(aminosulphonyl)-N-3-phenethyl guanide,
N-(5-methyl-1H-benzo[d]imidazol-2-yl)pyrrolidine-1-carboximidamide
N-(5-fluoro-1H-benzo[d]imidazol-2-yl)pyrrolidine-1-carboximidamide,
N-(5-(trifluoromethoxy)-1H-benzo[d]imidazol-2-yl)pyrrolidine-1-carboximidamide,
N-(5-methoxy-1H-benzo[d]imidazol-2-yl)pyrrolidine-1-carboximidamide,
N-(1H-benzo[d]imidazol-2-yl)pyrrolidine-1-carboximidamide,
1-phenethyl-3-(thiazol-2-yl)urea,
1-(oxazol-2-yl)-3-phenethyl urea,
1-benzyl-3-(oxazol-2-yl)urea,
1-(4-fluorobenzyl)-3-(thioazol-2-yl)urea,
1-(4-fluorobenzyl)-3-(oxazol-2-yl)urea,
1-ethyl-3-(oxazol-2-yl)urea,
1-ethyl-3-(thioazol-2-yl)urea,
1-(4-fluorophenethyl)-3-(thioazol-2-yl)urea,
1-benzyl-3-(thioazol-2-yl)urea,
1-phenyl-3-(thioazol-2-yl)urea
1-(oxazol-2-yl)-3-phenylurea
1,1-dimethyl-3-(thioazol-2-yl)urea,
1-(1H-imidazol-2-yl)-3-phenylurea
N-1-(N,N-dimethylaceteamide-N-5-(4-trifluoromethoxy)phenylbiguanide,
N-carbamoylpyrrolidine-1-carboxyimidamide,
N-1-carbamoyl-N-3-dimethyl guanide N-1-phenyl-N-3-carbamoyl guanide
N-1-buthyl-N-3-carbamoylguanide N-1-phenethyl-N-3-carbamoylguanide,
N-1-imidamidyl-N-3-phenyl urea
N-(imino(pyrolidin-1-yl)methyl)pyrolidine-1-carboxyamide
N-(phenylcarbamoyl)pyrolidine-1-carboxyimidamide
N-(imidamidyl)-N-(4-fluoro)phenethyl urea,
N-(4-fluorobenzyl)-4,5-dihydro-1H-imidazole-2-amine,
N-(4-fluorophenethyl)-4,5-dihydro-1H-imidazole-2-amine,
N-1-phenethyl-N-5-acetylbiguanide,
1-(2,3-dihydro-1H-inden-2-yl)biguanide, and
N-carbamimidoylisoindoline-2-carboximidamide The synthesis of certain compound represented by Chemical Formula 3 is illustrated in reaction scheme (1).

Reaction Scheme (1)

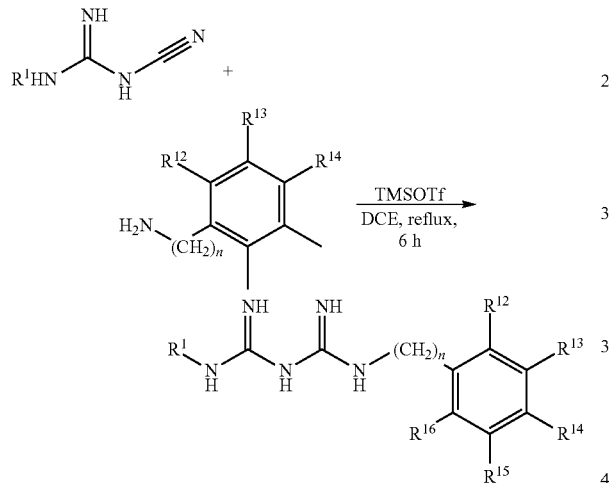

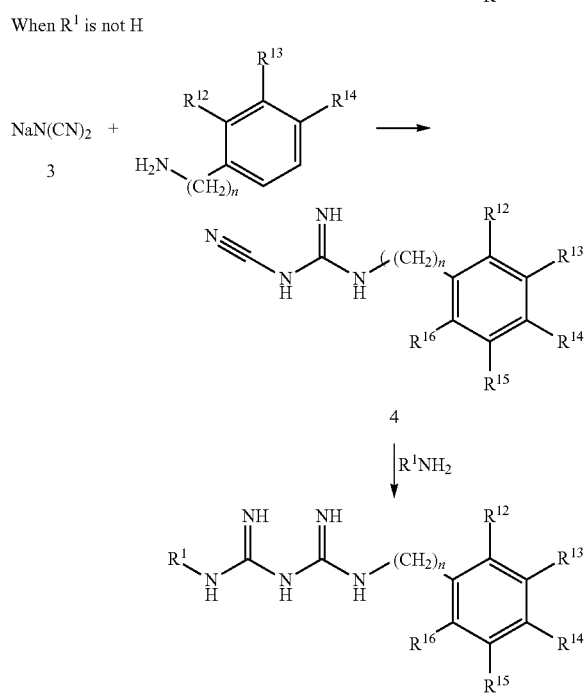

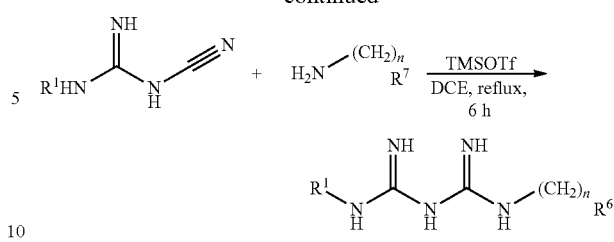

1 eq. of TMSOTf is added to an amine (2) in dichloroethane. The mixture is stirred at room temperature for 30 min. 1 eq. of dicyanamide (1) is added to the mixture, and then the reaction mixture is refluxed for 6 h. After the reaction is completed, the reaction mixture is cooled down to room temperature. To the mixture were added 12 N HCl solutions, stirred further for 1 h. The precipitates from the mixture is washed with dichloroethane and dissolved in minimum amount of methanol. To the solution is added excess of ethyl acetate, and stirred further for 1 h to produce crude residue. The residue is washed with ethyl acetate, and then dried under reduced pressure yielding the desired solid product.

The synthesis of certain compound represented by Chemical Formula 5 is illustrated in scheme (2).

Reaction Scheme (2)

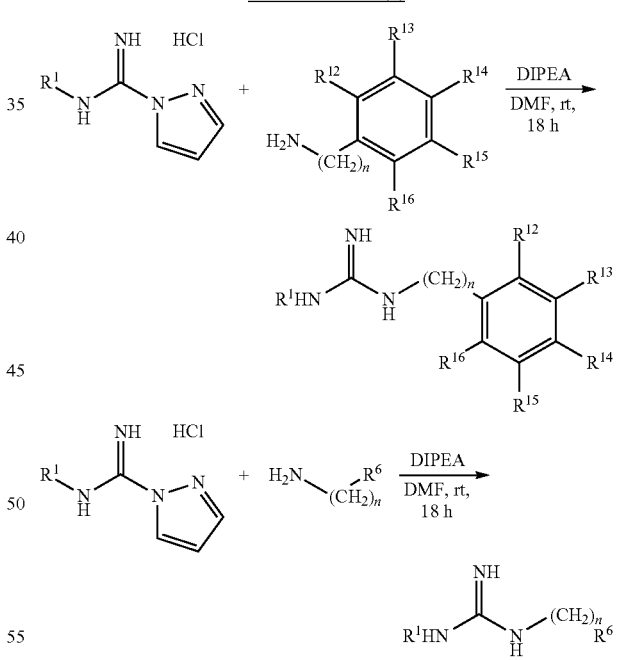

To an amine in DMF is added 1-amidino pyrazole HCl (1 eq.) and isopropylamine (3 eq.). The reaction mixture is stirred at room temperature for 18 h. After the reaction is completed, the solvent of the mixture is reduced under reduced pressure to produce the residue. The residue is treated with 12N HCl solutions with purification to produce desired products.

The synthesis of certain compound represented by Chemical Formula 6 is illustrated in scheme (3).

Reaction Scheme (3)

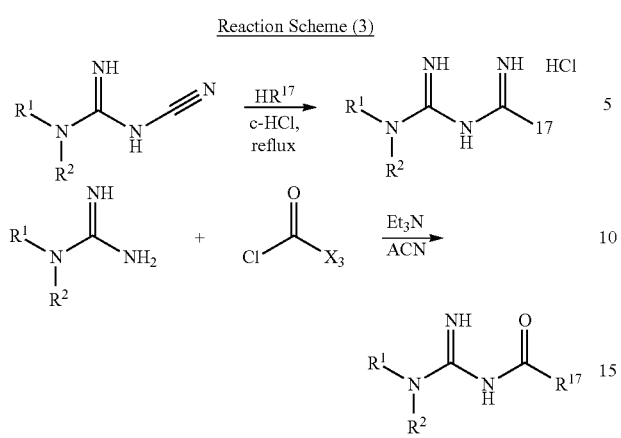

The cyanoguanidine is dissolved in alcohol or thiol and is added by 12N HCl solution. The reaction mixture is refluxed for 2 hour and is condensed under reduced pressure to produce the crude residue. The desired products are obtained by purifying the residue.

Triethylamine (2 eq) is added to a solution of the guanidine in acetonitrile and then is stirred at room temperature for 30 minutes. Acetyl chloride (1 eq) is added to the mixture dropwisely. After the addition is completed, the reaction mixture is stirred at the temperature for 2 hours. The solvent is removed under reduced pressure to produce the crude residue. The residue is purified using silica-gel chromatography to obtain the desired product.

The guanidine compounds of present invention can function as mitochondrial oxidative phosphorylation (OXPHOS) inhibitor. As used herein, the term "OXPHOS inhibitor" refers to an agent that inhibits oxidative phosphorylation, for example, oxidative phosphorylation in the mitochondria, either by direct inhibition of proteins involved in oxidative phosphorylation, or by inhibition of expression of the proteins involved in oxidative phosphorylation. The conventional OXPHOS inhibitors are metformin, phenformin and buformin. Metformin is a mitochondrial complex 1 inhibitor that can be used to target mitochondrial OXPHOS.

Thus, the present invention relates to a use of the guanidine compounds for inhibiting mitochondrial OXPHOS or reprogramming cellular metabolism. More specifically, the present invention relates to a pharmaceutical composition for preventing or treating a disease associated with mitochondrial OXPHOS.

The disease is at least one selected from the group consisting of diabetes mellitus, obesity, hyperlipemia, hypercholesterolemia, fatty liver, coronary artery disease, osteoporosis, polycystic ovary syndrome, metabolic syndrome, cancer, muscle pain, myocyte damage and rhabdomyolysis.

The diabetes mellitus is insulin-independent diabetes mellitus.

The cancer can be uterine cancer, breast cancer, gastric cancer, brain cancer, colorectal cancer, lung cancer, skin cancer, blood cancer and liver cancer, but not limited thereto.

The guanidine compounds of present invention have superior inhibitory effect on cancer cell growth, cancer metastasis and cancer reoccurrence to conventional drugs, even though smaller amount of the compounds are used.

The compounds of the present invention are improved guanide compounds with improved potency and anticancer activity in low glucose condition. The role of OXPHOS inhibitor of the present invention is not limited in growth inhibition of cancer, but also lower cancer stem cell like population, recurrence, and enhance efficacy of other anti-cancer drugs in the combination.

An aspect of the invention is to provide a method of preventing or treating a disease associated with OXPHOS, particularly cancer by inhibiting mitochondrial oxidative phosphorylation and reprogramming cellular metabolism, comprising administering the guanidine compound of present invention to a subject in need.

The compounds of invention can be used in combination with other pharmaceutical agents or treatment methods, for examples, chemotherapeutics, anti-cancer drugs, anti-cancer antibody drug, radiation, immunotherapy agents, and kinase inhibitors. The combination agent can be administered in a combined form or separate form.

Chemotherapeutic agents in combination with the compound of invention include (without limitation) alkylating agents, uracil mustards, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, temozolomide, methotrexate, 5-fluorouracil, floxuridine, cytarabine, 6-mercaptopurine, 6-thioguanide, gemcitabine, doxorubicin, epirubicin, idarubicin, ara-C, paclitaxel (Taxol™), navelbene, letrozole, anastrazole, capecitabine, cis-platin, carboplatin, and topoisomerase inhibitors. Anti-cancer antibodies include trastuzumab (Herceptin), and bevacizumab (Avastin). Immunotherapy agents include interferon, anti-PD1 antibody, anti-CTLA4 antibody, IDO1 inhibitors, and other immune cell therapies including adoptive T cell or NK cells. Kinase inhibitors include dasatinib, trametinib, palbociclib, or tyrosine kinase inhibitors such as erlotinib, gefatinib, but not limited thereto.

[Measurement of Mitochondrial Complex I Inhibition]

The electron transfer complex in mitochondria is composed of 5 complexes. The complex I accept electrons from NADH produced from glycolysis and TCA cycle and the electrons move to complex II, III and IV and the electron is finally transferred to $O_2$ and water molecule is generated. During the electron transfer, proton gradient is generated and the chemical gradient is a driving source to synthesize ATP at complex V. The mitochondrial inhibition of complex I indirectly assessed by measuring the oxygen consumption rate (OCR) at complex IV. When the mitochondrial ETC is inhibited, glycolysis is up-regulated and lactate production is increased. The solution outside of cells becomes acidic (lower pH) as lactate is transported to outside of cells. OCR and Extracellular acidification rate (ECAR) are determined by XF Analyzer (Seahorse Biosciences). The compounds of present invention caused lower OCR by inhibition of complex I and higher ECAR by redirecting cellular metabolism to glycolysis.

[Cytotoxicity Assay in Low Glucose Condition]

The inhibition of oxidative phosphorylation (OXPHOS) is not cytotoxic to cells in normal glucose condition, because it is postulated that normal cells have compensatory mechanism under energy stress conditions such as low glucose. However OXPHOS inhibitors show cytotoxic effect on cells in the glucose deprived condition (BirsoyK, 2014). The glucose deprived condition is observed in tumor microenvironment potentially due to poor angiogenesis. Therefore the OXPHOS inhibitors may show anti-cancer effect on cancer cells in low glucose condition that may depict tumor microenvironment.

The compounds of the present invention were evaluated their cytotoxicity in SK-MEL-28, melanoma with 0.75 mM glucose supplement. The cytotoxic effect is compared with the cytotoxicity caused by phenformin. The cytotoxicity in low glucose condition is correlated with inhibition of oxygen consumption in mitochondria.

[In Vivo Xenograft Study]

The compounds of the present invention were evaluated in vivo using xenograft human cancer model in mice. The compounds of invention were administrated orally or interperitoneal injection. Tumor cell lines were cultured in vitro as monolayer culture. Using female BALB/c nude mice with immune system compromised, each mouse was inoculated subcutaneously at the right flank with tumor cells for tumor development. The treatment was started when the tumor size reaches approximately 100 mm³

The pharmaceutically acceptable salt of the compound according to the present invention may be an acid addition salt formed using organic acid or inorganic acid. The organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, dichloroacetic acid, aminooxy acetic acid, benzenesulfonic acid, 4-toluenesulfonic acid and methanesulfonic acid salts. The inorganic acid may include, for examples, hydrochloric acid, hydrobromic acid, sulfuric acid, phosphoric acid, nitric acid, carbonic acid, and boric acid salts. The acid addition salt may be prepared by a common preparation method of salts, such as a) directly mixing the compound of the present invention and acid, b) dissolving the compound of the present invention or acid in a solvent or a an aqueous solvent and mixing them, or c) mixing the compound of the present invention and acid in a solvent or an aqueous solvent.

Thus, another embodiment of the present invention provides a pharmaceutical composition comprising the guanide compound or a pharmaceutical salt thereof as an active ingredient. The pharmaceutical composition according to the present invention has excellent cancer cell proliferation inhibition effect, and thus, it may be used as an anticancer agent for various cancers, and specific Examples of the cancer include breast, lung, melanoma, pancreas, brain, ovary, prostate, cervix, testes, renal, head and neck, liver, lymphoma, leukemia, endometrial cancer, cholangiocarcinoma, but not limited thereto.

The pharmaceutical composition of the present invention comprises at least one pharmaceutically acceptable carrier in addition to the active ingredient. As used herein, 'pharmaceutically acceptable carrier' means known pharmaceutical excipient that is useful for formulation of a pharmaceutically active compound for administration and is substantially non-toxic and non-sensitive under use conditions. The exact ratio of the excipient is determined by standard pharmaceutical practice, as well as by the solubility and the chemical properties of active compounds and the selected administration route.

The pharmaceutical composition of the present invention may be formulated into a form suitable for a desired administration method using adjuvant such as a physiologically acceptable excipient, a disintegrating agent, a sweetener, a binder, coating material, a blowing agent, a lubricant, a slip modifier, a flavoring agent and the like.

The pharmaceutical composition may be formulated in the form of tablets, capsules, pills, granule, powder, injections or liquid. The dosage form of the pharmaceutical composition and the pharmaceutically acceptable carrier may be appropriately selected according to technologies known in the art.

Meanwhile, as used herein, a 'subject' means a warm-blooded animal such as a mammal with a specific disease, disorder or condition, and for Example, it includes a human being, an orangutan, a chimpanzee, a mouse, a rat, a dog, a cow, a chicken, a pig, a goat, a sheep and the like, but is not limited thereto.

The term, 'treatment' or 'treating' includes relieving symptoms, temporarily or permanently removing the cause of symptoms, or preventing or slowing the appearance of symptoms and the progress of the disease, disorder or condition, but is not limited thereto.

The effective amount of the active ingredient of the pharmaceutical composition of the present invention means an amount required for achieving treatment of a disease. Thus, it may be controlled according to various factors including kind of disease, severity of disease, kind and content of active ingredients and other ingredients contained in the composition, kind of dosage form, and age, weight, general health state, gender and diet of a patient, administration time, administration route, secretion rate of the composition, treatment period, simultaneously used drugs, and the like. For example, in the case of an adult, the compound of the Chemical Formula 1 may be administered once or several times a day in the total amount of 50 to 3000 mg/kg.

The guanide derivatives according to the present invention may exhibit excellent cancer cell proliferation inhibition and cancer metastasis and recurrence inhibition effects even with a small amount compared to the existing drugs, and thus, may be usefully used for treatment of various cancers including breast, lung, melanoma, pancreas, brain, ovary, prostate, cervix, testes, renal, head and neck, liver, lymphoma, leukemia, endometrial cancer, cholangiocarcinoma and the like, inhibition of cancer cell proliferation, and inhibition of cancer metastasis.

EXAMPLE

Hereafter, the invention will be described in more detail through examples and comparative examples. However, the following examples are to merely illustrate the present invention, and the scope of the invention is not limited by them in any ways.

Example 1

N-1-(3,4-dichloro)phenethylbiguanide hydrochloride

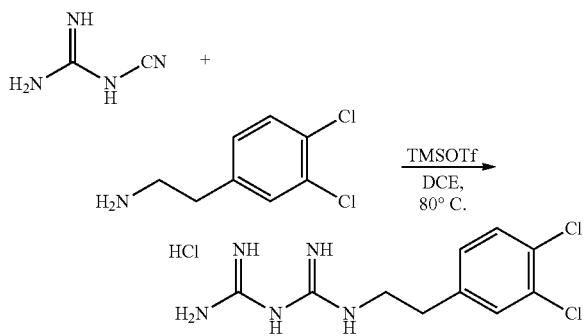

3,4-dichloro phenethylamine (1.1 g, 6.02 mmol) was dissolved in dichloromethane solution (20 mL) and was agitated with the addition of trimethylsilyl trifluoromethane sulphonate (1.1 ml, 6.02 mmol) at a room temperature for 30 minutes. The reaction solution was added by cyanoguanide (0.5 g, 6.02 mmol) and agitated by reflux with reflux at 80° C. for 6 hours. After the reaction completed, the reaction product was maintained at a room temperature, and agitated for 1 hour with the addition of 12N HCl (0.5 ml, 6.02 mmol). The produced solid was filtered, washed with dichloromethane 10 ml, dissolved in a small amount of methanol and then agitated with the addition of ethylacetate 20 ml at room temperature for 1 hour. The solid was filtered, washed with ethylacetate 10 ml and dried under vacuum to produce the title compound in white solid (1.1 g, 61%).

1H NMR (600 MHz, DMSO-d6) δ 9.32 (brs, 1H), 8.90 (brs, 0.2H), 8.22 (brs, 3H), 7.58 (m, 3H), 7.30 (m, 1H), 3.44 (m, 2H), 2.85 (m, 2H) LCMS: 274.1 (M+H+)

Example 2

N-1-(2,5-dichloro)phenethylbiguanide hydrochloride

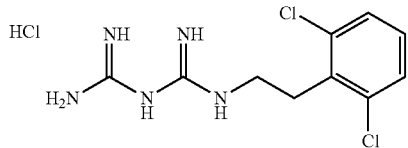 [SMILES: Cl ; N=C(N)NC(=N)NCCc1c(Cl)cccc1Cl]

The title compound (630 mg, 78%) in white solid was obtained according to the same method of Example 1, except that 2,5-dichlorophenethylamine was used instead of 3,4-dichloro phenethylamine.

1H NMR (600 MHz, CD3OD) δ 7.25 (m, 2H), 7.10 (m, 1H), 3.44 (m, 2H), 3.18 (m, 2H) LCMS: 274.1 (M+H+)

Example 3

N-1-(2-chloro)phenethylbiguanide hydrochloride

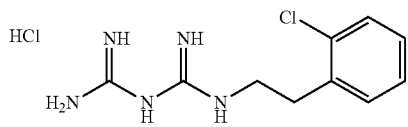 [SMILES: Cl ; N=C(N)NC(=N)NCCc1ccccc1Cl]

The title compound (1.73 g, 94.2%) in white solid was obtained according to the same method of Example 1, except that 2-chlorophenethylamine was used instead of 3,4-dichlorophenethylamine.

H NMR (600 MHz, DMSO-d6) δ 8.89 (s, 1H), 8.21 (s, 2H), 7.46 (m, 2H), 7.32 (m, 2H), 3.44 (s, 2H), 2.98 (s, 2H) LCMS: 240, 242 (M+H+)

Example 4

N-1-(2,4-dichloro)phenethylbiguanide hydrochloride

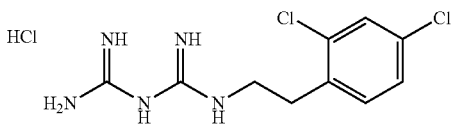 [SMILES: Cl ; N=C(N)NC(=N)NCCc1ccc(Cl)cc1Cl]

The title compound (1.59 g, 90.3%) in white solid was obtained according to the same method of Example 1, except that 2,4-dichlorophenethylamine was used instead of 3,4-dichloro phenethylamine.

1H NMR (600 MHz, DMSO-d6) δ 8.97 (br s, 1H), 8.97 (br s, 2H), 7.61 (d, J=1.8 Hz, 1H), 7.49 (s, 1H), 7.42 (m, 1H), 3.45 (s, 2H), 2.97 (s, 2H).

LCMS: 274, 276 (M+H+)

Example 5

N-1-(3-fluoro)phenethylbiguanide hydrochloride

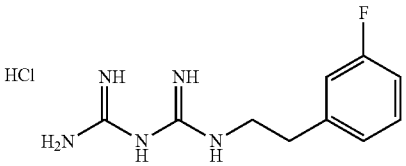 [SMILES: Cl ; N=C(N)NC(=N)NCCc1cccc(F)c1]

The title compound (800 mg, 61.8%) in white solid was obtained according to the same method of Example 1, except that 3-fluoro phenethylamine was used instead of 3,4-dichloro phenethylamine.

1H NMR (600 MHz, DMSO-d6) δ 9.15 (s, 1H), 8.52 (s, 2H), 7.35 (m, 1H), 7.2 (m, 2H), 7.05 (s, 1H), 3.51 (s, 2H), 2.89 (s, 2H) LCMS: 224 (M+H+)

Example 6

N-1-(4-trifluoromethoxy)phenethylbiguanide hydrochloride

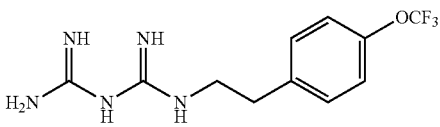

The title compound (154 mg, 32%) in white solid was obtained according to the same method of Example 1, except that 4-trifluoromethoxy phenethylamine was used instead of 3,4-dichloro phenethylamine.

1H NMR (600 MHz, DMSO) δ 9.2 (m, 1H), 8.43 (m, 2H), 8.19 (m, 2H), 7.66 (d, J=7.8 Hz, 2H), 7.50 (m, 2H), 3.43 (bs, 2H), 2.98 (bs, 2H) LCMS: 290.1 (M+H+)

Example 7

N-1-(4-trifluoromethyl)phenethylbiguanide hydrochloride

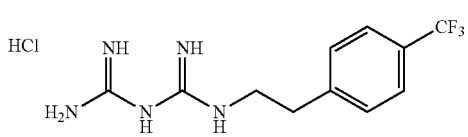 [SMILES: Cl ; N=C(N)NC(=N)NCCc1ccc(C(F)(F)F)cc1]

The title compound (203 mg, 45%) in white solid was obtained according to the same method of Example 1, except that 4-trifluoromethyl phenethylamine was used instead of 3,4-dichloro phenethylamine.

1H NMR (600 MHz, DMSO) δ 9.4 (m, 1H), 8.59 (m, 2H), 8.23 (m, 2H), 7.68 (d, J=7.8 Hz, 2H), 7.54 (m, 2H), 3.48 (bs, 2H), 2.94 (bs, 2H) LCMS: 274 (M+H+)

Example 8

N-1-(3-methoxy)phenethylbiguanide hydrochloride

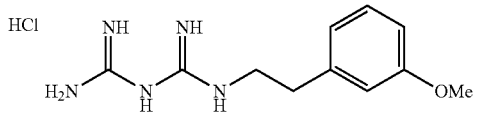 [SMILES: Cl ; COc1cccc(CCNC(=N)NC(=N)N)c1]

The title compound (980 mg, 98%) in white solid was obtained according to the same method of Example 1, except that 3-methoxy phenethylamine was used instead of 3,4-dichloro phenethylamine.

1H NMR (600 MHz, DMSO) δ 9.31 (brs, 1H), 8.79 (brs, 2H), 8.19 (brs, 3H), 7.23 (dd, J=7.8 Hz, 1H), 6.97 (d, J=7.8 Hz, 1H), 6.90 (d, J=7.2 Hz, 2H), 3.32 (m, 2H) 2.83 (m, 2H) LCMS: 236.1 (M+H+)

Example 9

N-1-(2-fluoro)phenethylbiguanide hydrochloride

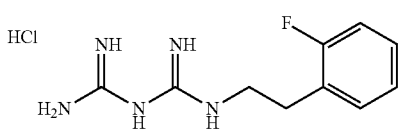 [SMILES: Cl ; N=C(N)NC(=N)NCCc1ccccc1F]

The title compound (800 mg, 45.8%) in white solid was obtained according to the same method of Example 1, except that 2-fluoro phenethylamine was used instead of 3,4-dichloro phenethylamine.

1H NMR (400 MHz, CD3OD) δ 7.31 (m, 2H), 7.14 (m, 2H), 3.61 (t, J=6.8H2z, 2H), 6.04 (t, J=7.2 Hz, 2H) LCMS: 224 (M+H+)

Example 10

N-1-(4-methyl)phenethylbiguanide hydrochloride

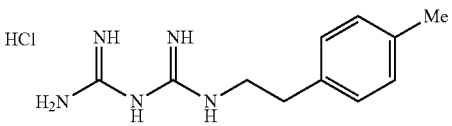 [SMILES: Cl ; Cc1ccc(CCNC(=N)NC(=N)N)cc1]

The title compound (161 mg, 43%) in white solid was obtained according to the same method of Example 1, except that 4-methyl phenethylamine was used instead of 3,4-dichloro phenethylamine.

1H NMR (400 MHz, CD3OD) δ 7.31 (m, 2H), 7.14 (m, 2H), 3.61 (t, J=6.8 Hz, 2H), 6.04 (t, J=7.2 Hz, 2H) LCMS: 224 (M+H+)

Example 11

N-1-(4-methanesulphoneamine)phenethylbiguanide hydrochloride

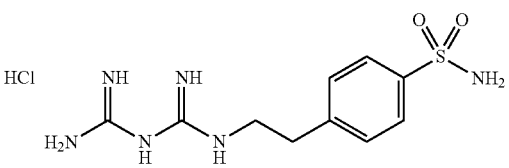 [SMILES: Cl ; N=C(N)NC(=N)NCCc1ccc(S(N)(=O)=O)cc1]

The title compound (172 mg, 36%) in white solid was obtained according to the same method of Example 1, except that (4-methanesulphoneamine) phenethylamine was used instead of 3,4-dichloro phenethylamine.

1H NMR (600 MHz, DMSO) δ 7.99 (bs, 2H), 7.78 (d, J=7.8 Hz, 2H), 7.46 (d, J=7.8 Hz, 2H), 7.36 (s, 2H), 3.07 (m, 2H), 2.96 (bs, 2H) LCMS: 285 (M+H+)

Example 12

N-1-(4-(N,N-dimethyl)phenethylbiguanide hydrochloride

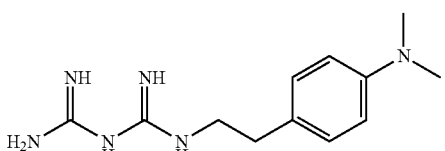

The title compound (300 mg, 49.2%) in white solid was obtained according to the same method of Example 1, except that 4-(N,N-dimethyl)-4-phenethylamine was used instead of 3,4-dichloro phenethylamine.

1H NMR (400 MHz, CD3OD) δ 7.21 (s, 4H), 3.58 (t, J=7.6 Hz, 2H), 2.94 (t, J=7.6 Hz, 2H), 2.87 (m, 1H), 1.23 (d, J=7.2 Hz, 6H) LCMS: 274 (M+H+)

Example 13

N-1-(4-phenoxy)phenethylbiguanide hydrochloride

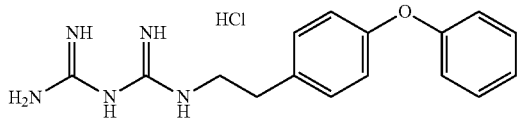 [SMILES: N=C(N)NC(=N)NCCc1ccc(Oc2ccccc2)cc1 ; Cl]

The title compound (280 mg, 46.7%) in white solid was obtained according to the same method of Example 1, except that 4-phenoxy phenethylamine was used instead of 3,4-dichloro phenethylamine.

1H NMR (400 MHz, CD3OD) δ 7.34 (m, 4H), 7.11 (m, 2H), 6.96 (d, J=8.4 Hz, 4H), 3.60 (t, J=7.8 Hz, 2H), 2.97 (t, J=7.2 Hz, 2H) LCMS: 298 (M+H+)

Example 14

N-1-(4-isopropyl)phenethylbiguanide hydrochloride

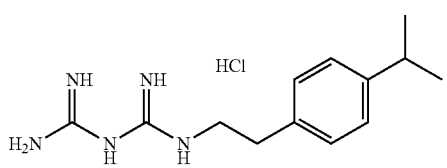 [SMILES: CC(C)c1ccc(CCNC(=N)NC(=N)N)cc1 ; Cl]

The title compound (280 mg, 62.7%) in white solid was obtained according to the same method of Example 1, except that 4-isopropyl phenethylamine was used instead of 3,4-dichloro phenethylamine.

1H NMR (400 MHz, CD3OD) δ 7.21 (s, 4H), 3.58 (t, J=7.6 Hz, 2H), 2.94 (t, J=7.6 Hz, 2H), 2.87 (m, 1H), 1.23 (d, J=7.2 Hz, 6H) LCMS: 274 (M+H+)

Example 15

N-1-(3,4-dimethyl)phenethylbiguanide hydrochloride

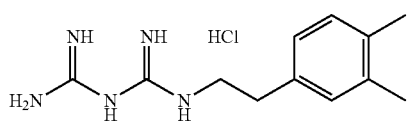 [SMILES: Cc1ccc(CCNC(=N)NC(=N)N)cc1C ; Cl]

The title compound (696 mg, 96.3%) in white solid was obtained according to the same method of Example 1, except that 3,4-dimethyl phenethylamine was used instead of 3,4-dichloro phenethylamine.

1H NMR (400 MHz, CD3OD) δ 7.11 (d, J=8.0 Hz, 1H), 7.01 (m, 2H), 3.54 (t, J=7.6 Hz, 2H), 2.96 (t, J=7.2 Hz, 2H), 2.32 (d, J=22.8 Hz, 6H) LCMS: 234 (M+H+)

Example 16

N-1-(2,4-dimethyl)phenethylbiguanide hydrochloride

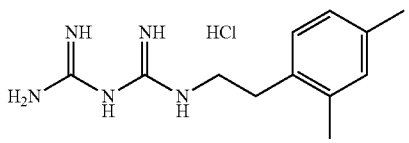 [SMILES: Cc1ccc(CCNC(=N)NC(=N)N)c(C)c1 ; Cl]

The title compound (626 mg, 86.6%) in white solid was obtained according to the same method of Example 1, except that 2,4-dimethyl phenethylamine was used instead of 3,4-dichloro phenethylamine.

1H NMR (400 MHz, CD3OD) δ 7.09 (m, 2H), 7.02 (m, 1H), 3.58 (t, J=7.6 Hz, 2H), 2.91 (t, J=7.2 Hz, 2H), 2.25 (d, J=11.2 Hz, 6H) LCMS: 234 (M+H+)

Example 17

N-1-(4-fluoro-2-methyl)phenethylbiguanide hydrochloride

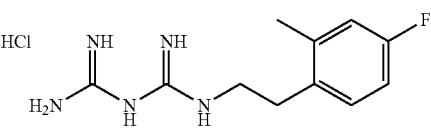 [SMILES: Cl ; Cc1cc(F)ccc1CCNC(=N)NC(=N)N]

The title compound (350 mg, 65.3%) in white solid was obtained according to the same method of Example 1, except that 4-fluoro-2-methyl phenethylamine was used instead of 3,4-dichloro phenethylamine.

1H NMR (600 MHz, DMSO) δ 9.48 (brs, 1H), 8.94 (brs, 2H), 8.32 (brs, 3H), 7.27 (m, 1H), 7.02 (m, 2H), 3.39 (m, 2H), 2.82 (m, 2H), 2.30 (s, 3H)

LCMS: 220 (M+H+)

Example 18

N-1-(2,4-dimethyl)benzylbiguanide hydrochloride

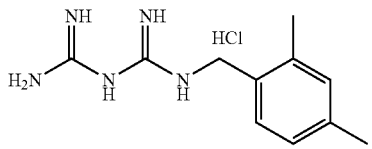 [SMILES: Cc1ccc(CNC(=N)NC(=N)N)c(C)c1 ; Cl]

The title compound (230 mg, 30.3%) in white solid was obtained according to the same method of Example 1, except that 2,4-dimethyl benzylamine was used instead of 3,4-dichloro phenethylamine.

1H NMR (400 MHz, CD3OD) δ 7.21 (d, J=7.6 Hz, 1H), 7.09 (s, 1H), 7.06 (d, J=7.6 Hz, 1H), 4.49 (s, 2H), 2.35 (s, 3H), 2.28 (s, 3H)

LCMS: 220 (M+H+)

Example 19

N-1-(4-fluoro-3-methoxy)phenethylbiguanide hydrochloride

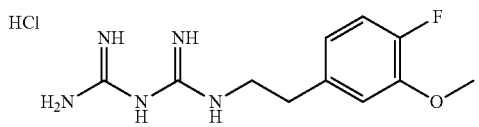 [SMILES: Cl ; COc1cc(CCNC(=N)NC(=N)N)ccc1F]

The title compound (12 mg, 3.8%) in white solid was obtained according to the same method of Example 1, except that 4-fluoro-3-methoxy phenethylamine was used instead of 3,4-dichloro phenethylamine.

1H NMR (600 MHz, CD3OD) δ 6.96 (m, 2H), 6.74 (m, 1H), 3.85 (s, 3H), 3.43 (m, 2H), 2.79 (m, 2H) LCMS: 254.1 (M+H+)

Example 20

N-1-(3,4-difluoro)phenethylbiguanide hydrochloride

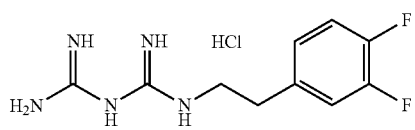 [SMILES: N=C(N)NC(=N)NCCc1ccc(F)c(F)c1 ; Cl]

The title compound (84 mg, 23%) in white solid was obtained according to the same method of Example 1, except that 3,4-difluoro phenethylamine was used instead of 3,4-dichloro phenethylamine.

1H NMR (600 MHz, DMSO) δ 7.38 (m, 2H), 7.11 (bs, 2H), 3.39 (bs, 2H), 2.81 (bs, 2H) LCMS: 242 (M+H+)

Example 21

N-1-(2-morpholinoethyl)biguanide hydrochloride

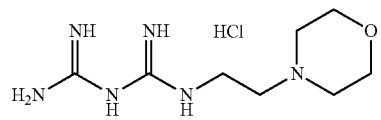

The title compound (423 mg, 73%) in white solid was obtained according to the same method of Example 1, except that 2-morpholinoethylamine was used instead of 3,4-dichloro phenethylamine.

1H NMR (600 MHz, DMSO) δ 7.4 (bs, 1H), 7.08 (bs, 5H), 3.87 (bs, 4H), 3.51 (bs, 2H), 3.34 (bs, 4H), 3.21 (bs, 2H) LCMS: 215 (M+H+)

Example 22

N-1-(2-methyl)phenethylbiguanide hydrochloride

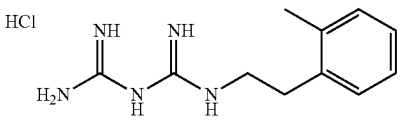 [SMILES: Cl ; Cc1ccccc1CCNC(=N)NC(=N)N]

The title compound (350 mg, 70%) in white solid was obtained according to the same method of Example 1, except that 2-methylphenethylamine was used instead of 3,4-dichloro phenethylamine.

1H NMR (600 MHz, DMSO) δ 9.47 (brs, 1H), 8.94 (brs, 2H), 8.35 (brs, 3H), 7.36 (m, 1H), 7.46 (m, 3H), 3.41 (m, 1H), 2.84 (m, 2H), 2.29 (s, 3H) LCMS: 242 (M+H+)

Example 23

N-1-(3-bromo-4-fluoro)benzylbiguanide hydrochloride

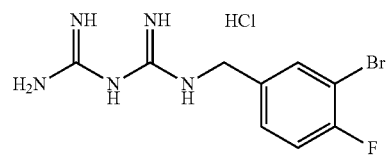 [SMILES: N=C(N)NC(=N)NCc1ccc(F)c(Br)c1 ; Cl]

The title compound (1.02 g, 75.6%) in white solid was obtained according to the same method of Example 1, except that 3-bromo-4-fluoro benzylamine was used instead of 3,4-dichloro phenethylamine.

1H NMR (600 MHz, CD3OD) δ 7.73 (d, J=4.8 Hz, 1H), 7.44 (s, 1H). 7.27 (t, J=8.42 Hz, 1H), 4.55 (s, 2H) LCMS: 220.1 (M+H+)

Example 24

N-1-(2-fluoro-4-methyl)benzylbiguanide hydrochloride

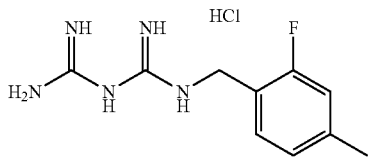 [SMILES: Cl ; Cc1ccc(CNC(=N)NC(=N)N)c(F)c1]

The title compound (400 mg, 54.1%) in white solid was obtained according to the same method of Example 1, except that 2-fluoro-4-methyl benzylamine was used instead of 3,4-dichloro phenethylamine.

1H NMR (600 MHz, CD3OD) δ 7.36 (t, J=7.8 Hz, 1H), 7.06 (m, 2H), 4.57 (s, 2H), 2.36 (s, 3H) LCMS: 224 (M+H+)

Example 25

N-1-(2-(piperidin-1-yl)ethyl)biguanide hydrochloride

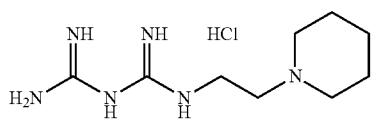 [SMILES: N=C(N)NC(=N)NCCN1CCCCC1 ; Cl]

The title compound (260 mg, 45%) in white solid was obtained according to the same method of Example 1, except that 2-(piperidin-1-yl)ethylamine was used instead of 3,4-dichloro phenethylamine.

1H NMR (600 MHz, DMSO) δ 3.54 (m, 2H), 3.45 (m, 2H), 3.16 (m, 2H), 2.90 (m, 2H), 1.80 (m, 4H), 1.69 (m, 1H), 1.38 (m, 1H) LCMS: 213.2 (M+H+)

Example 26

N-1-(2-bromo)phenethylbiguanide hydrochloride

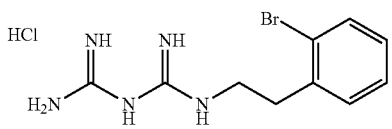 [SMILES: Cl ; N=C(N)NC(=N)NCCc1ccccc1Br]

The title compound (700 mg, 44%) in white solid was obtained according to the same method of Example 1, except that 2-bromo phenethylamine was used instead of 3,4-dichloro phenethylamine.

1H NMR (400 MHz, DMSO) δ 8.84 (brs, 1H), 8.19 (brs, 2H), 7.46 (m, 2H), 7.31 (brs, mH), 3.44 (m, 2H), 2.98 (m, 2H) LCMS: 240.1 (M+H+)

Example 27

N-1-(4-phenethyl)phenethylbiguanide hydrochloride

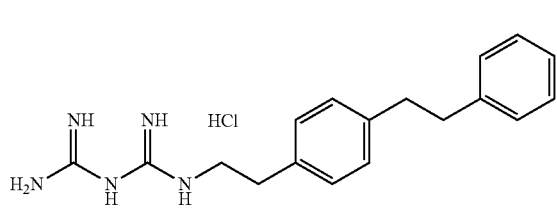 [SMILES: N=C(N)NC(=N)NCCc1ccc(CCc2ccccc2)cc1 ; Cl]

The title compound (30 mg, 9.7%) in white solid was obtained according to the same method of Example 1, except that N-(4-phenethyl)phenethyl amine was used instead of 3,4-dichloro phenethylamine.

1H NMR (400 MHz, CD3OD) δ 7.24-7.14 (m, 9H), 3.56 (s, 2H), 2.93 (s, 2H), 2.88 (s, 4H) LCMS: 310.2 (M+H+)

Example 28

N-1-(3,4-dimethyl)benzylbiguanide hydrochloride

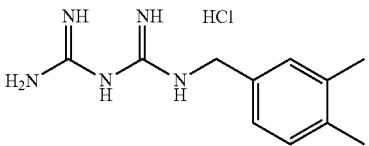 [SMILES: Cc1ccc(CNC(=N)NC(=N)N)cc1C ; Cl]

The title compound (20 mg, 84.7%) in white solid was obtained according to the same method of Example 1, except that 3,4-dimethyl benzylamine was used instead of 3,4-dichloro phenethylamine.

1H NMR (400 MHz, CD3OD) δ 7.21 (d, J=7.6 Hz, 1H), 7.09 (s, 1H), 7.06 (d, J=7.6 Hz, 2H), 4.49 (s, 2H), 2.35 (s, 3H), 2.28 (s, 3H) LCMS: 220.1 (M+H+)

Example 29

N-1-4-cyclopropylethylbiguanide hydrochloride

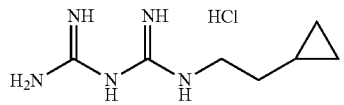 [SMILES: N=C(N)NC(=N)NCCC1CC1 ; Cl]

The title compound (20 mg, 4.1%) in white solid was obtained according to the same method of Example 1, except that cyclopropylethylamin was used instead of 3,4-dichloro phenethylamine.

1H NMR (600 MHz, CD3OD) δ 3.42 (m, 2H), 1.69 (m, 2H), 0.79 (m, 1H), 0.53 (m, 2H), 0.16 (m, 2H) LCMS: 170.1 (M+H+)

Example 30

N-1-(2-(5,6,7,8-tetrahydronaphthalen-2-yl)ethyl)biguanide hydrochloride

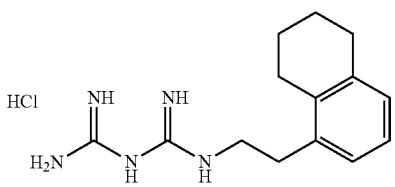 [SMILES: Cl ; N=C(N)NC(=N)NCCc1cccc2c1CCCC2]

The title compound (280 mg, 33%) in white solid was obtained according to the same method of Example 1, except that 2-(5,6,7,8-tetrahydronaphthalen-2-yl)ethyl amine was used instead of 3,4-dichloro phenethylamine.

1H NMR (400 MHz, DMSO) 7.94 (brs, 2H), 7.04 (m, 2H), 6.93 (m, 1H), 3.16 (m, 2H), 2.77 (m, 2H), 2.77 (m, 2H), 2.71 (m, 2H). 2.67 (m, 2H), 1.76 (m, 2H), 1.69 (m, 2H) LCMS: 240.1 (M+H+)

Example 31

N-(1-(2-naphthalene)methyl)biguanide hydrochloride

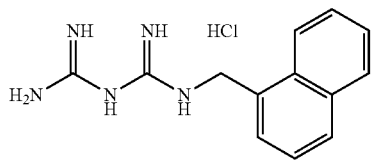 [SMILES: N=C(N)NC(=N)NCc1cccc2ccccc12 ; Cl]

The title compound (1.65 g, 93.2%) in white solid was obtained according to the same method of Example 1, except that 1-Naphthylmethylamine was used instead of 3,4-dichloro phenethylamine.

1H NMR (600 MHz, CD3OD) δ 8.04 (d, J=8.4 Hz, 1H), 7.96 (m, 2H), 7.64 (t, J=7.8 Hz, 1H), 7.59 (m, 2H), 7.53 (t, J=7.8 Hz, 1H), 4.90 (s, 2H)

LCMS: 242.1 (M+H+)

Example 32

N-1-2-cyclohexylethylbiguanide hydrochloride

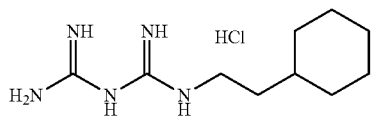

The title compound (650 mg, 83.3%) in white solid was obtained according to the same method of Example 1, except that 2-cyclohexylethylamine was used instead of 3,4-dichloro phenethylamine.

1H NMR (600 MHz, CD3OD) δ 3.37 (t, J=7.8 Hz, 2H), 1.76 (m, 4H), 1.70 (m, 1H), 1.58 (m, 2H), 1.40 (m, 1H), 1.31 (m, 2H), 1.22 (m, 1H), 1.00 (m, 2H)

LCMS: 212.3 (M+H+)

Example 33

N-1-(2,4-dichloro)benzylbiguanide hydrochloride

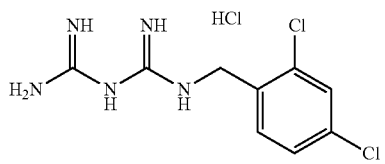 [SMILES: Cl ; N=C(N)NC(=N)NCc1ccc(Cl)cc1Cl]

The title compound (740 mg, 88.1%) in white solid was obtained according to the same method of Example 1, except that 2,4-dichloro benzylamine was used instead of 3,4-dichloro phenethylamine.

1H NMR (600 MHz, CD3OD) δ 7.59 (s, 1H), 7.52 (d, J=8.4 Hz, 1H), 7.44 (d, J=7.8 Hz, 1H), 4.65 (s, 2H) LCMS: 260.0, 262.0 (M+H+)

Example 34

N-1-(2,3-dichloro)benzylbiguanide hydrochloride

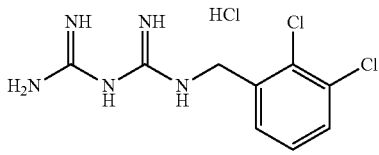 [SMILES: Cl ; N=C(N)NC(=N)NCc1cccc(Cl)c1Cl]

The title compound (720 mg, 85.7%) in white solid was obtained according to the same method of Example 1, except that 2,3-dichloro benzylamine was used instead of 3,4-dichloro phenethylamine.

1H NMR (600 MHz, CD3OD) δ 7.61 (d, J=7.2 Hz, 1H), 7.47 (d, J=7.8 Hz, 1H), 7.39 (t, J=7.8 Hz, 1H), 4.70 (s, 2H) LCMS: 260.0, 262.0 (M+H+)

Example 35

N-1-(benzo[d][1,3]dioxol-5-ylmethyl)biguanide hydrochloride

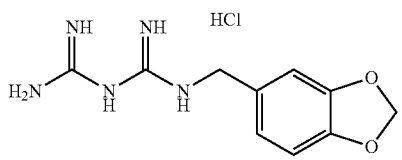 [SMILES: Cl ; N=C(N)NC(=N)NCc1ccc2c(c1)OCO2]

The title compound (480 mg, 76.2%) in white solid was obtained according to the same method of Example 1, except that piperonyl amine was used instead of 3,4-dichloro phenethylamine.

1H NMR (600 MHz, CD3OD) δ 6.90 (m, 2H), 6.85 (d, J=8.4 Hz, 1H), 5.97 (s, 2H), 4.45 (s, 2H) LCMS: 236.1 (M+H+)

Example 36

N-1-(2-chloro)benzylbiguanide hydrochloride

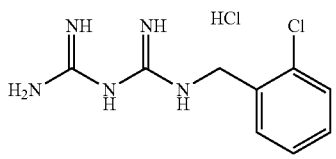 [SMILES: Cl ; N=C(N)NC(=N)NCc1ccccc1Cl]

The title compound (680 mg, 73.9%) in white solid was obtained according to the same method of Example 1, except that 2-chlorobenzylamine was used instead of 3,4-dichloro phenethylamine.

1H NMR (400 MHz, DMSO) δ 7.47 (m, 2H), 7.37 (m, 2H), 4.98 (s, 2H) LCMS: 226.1 (M+H+)

Example 37

N-1-(2,3-dichloro)benzylbiguanide hydrochloride

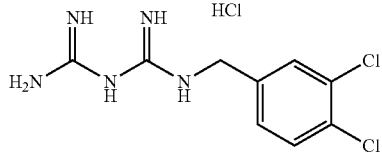 [SMILES: Cl ; N=C(N)NC(=N)NCc1ccc(Cl)c(Cl)c1]

The title compound (870 mg, 83.7%) in white solid was obtained according to the same method of Example 1, except that 2,3-dichlorobenzylamine was used instead of 3,4-dichloro phenethylamine.

1H NMR (600 MHz, CD3OD) δ 7.63 (s, 1H), 7.59 (d, J=7.8 Hz, 1H), 7.38 (d, J=7.2 Hz, 1H), 4.56 (s, 2H), LCMS: 260.0, 262.0 (M+H+)

Example 38

N-1-(2-methyl)benzylbiguanide hydrochloride

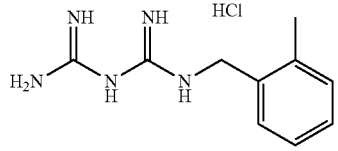

The title compound (890 mg, 76.4%) in white solid was obtained according to the same method of Example 1, except that 2-methylbenzylamine was used instead of 3,4-dichloro phenethylamine.

1H NMR (400 MHz, DMSO) δ 9.17 (brs, 1), 8.45 (brs, 3H), 7.31 (m, 1H), 7.22 (m, 4H), 4.45 (s, 2H), 2.29 (s, 3H) LCMS: 206.1 (M+H+)

Example 39

N-1-(2-bromo)benzylbiguanide hydrochloride

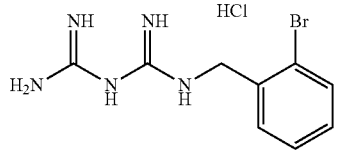 [SMILES: Cl ; N=C(N)NC(=N)NCc1ccccc1Br]

The title compound (780 mg, 76.4%) in white solid was obtained according to the same method of Example 1, except that 2-bromobenzylamine was used instead of 3,4-dichloro phenethylamine.

1H NMR (600 MHz, DMSO) δ 9.13 (brs, 1H), 8.40 (brs, 2H), 7.66 (m, 1H), 7.43 (m, 2H), 7.28 (m, 2H), 4.03 (s, 2H) LCMS: 270 (M+H+)

Example 40

N-1-(3-fluoro)benzylbiguanide hydrochloride

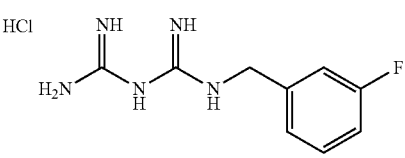 [SMILES: Cl ; N=C(N)NC(=N)NCc1cccc(F)c1]

The title compound (400 mg, 37%) in white solid was obtained according to the same method of Example 1, except that 3-fluorobenzylamine was used instead of 3,4-dichloro phenethylamine.

1H NMR (600 MHz, CD3OD) 7.44 (m, 1H), 7.22 (m, 2H), 7.12 (m, 1H), 4.56 (s, 2H) LCMS: 210.1 (M+H+)

Example 41

N-1-(3-chloro)benzylbiguanide hydrochloride

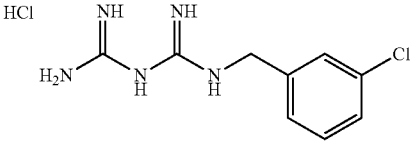 [SMILES: Cl ; N=C(N)NC(=N)NCc1cccc(Cl)c1]

The title compound (780 mg, 85%) in white solid was obtained according to the same method of Example 1, except that 3-chlorobenzylamine was used instead of 3,4-dichloro phenethylamine.

1H NMR (600 MHz, CD3OD) 7.47 (m, 1H), 7.41 (m, 2H), 7.35 (m, 1H), 4.56 (s, 2H) LCMS: 226.1 (M+H+)

Example 42

N-1-(2-fluoro)benzylbiguanide hydrochloride

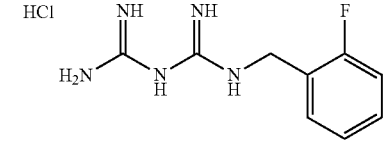 [SMILES: Cl ; N=C(N)NC(=N)NCc1ccccc1F]

The title compound (730 mg, 76%) in white solid was obtained according to the same method of Example 1, except that 2-fluorobenzylamine was used instead of 3,4-dichloro phenethylamine.

1H NMR (600 MHz, CD3OD) 7.47 (m, 2H), 7.20 (m, 2H), 4.61 (s, 2H)

LCMS: 210.1 (M+H+)

Example 43

N-1-(2,6-difluoro)benzylbiguanide hydrochloride

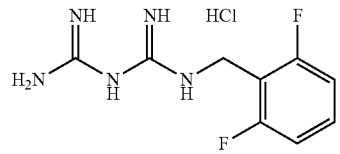 [SMILES: N=C(N)NC(=N)NCc1c(F)cccc1F ; Cl]

The title compound (274 mg, 40.8%) in white solid was obtained according to the same method of Example 1, except that 2,6-difluorobenzylamine was used instead of 3,4-dichloro phenethylamine 1H NMR (600 MHz, DMSO) 7.49 (m, 1H), 7.17 (m, 2H), 4.52 (s, 2H)

LCMS: 228.1 (M+H+)

Example 44

N-1-2-(5,6,7,8-tetrahydronaphthalen-2-yl)ethyl-biguanide hydrochloride

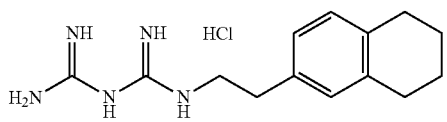 [SMILES: N=C(N)NC(=N)NCCc1ccc2c(c1)CCCC2 ; Cl]

The title compound (66 mg, 35.6%) in white solid was obtained according to the same method of Example 1, except that (5,6,7,8-tetrahydronaphthalen-2-yl)ethylamine was used instead of 3,4-dichloro phenethylamine.

1H NMR (600 MHz, DMSO) 6.97 (m, 3H), 3.38 (s, 2H), 2.74 (s, 2H), 2.67 (m, 4H), 1.71 (m, 4H) LCMS: 260.2 (M+H+)

Example 45

N-1-(2-(naphthalen-1-yl)methyl)biguanide hydrochloride

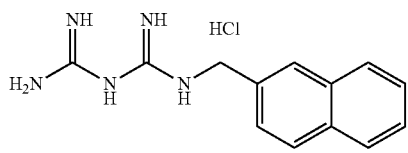 [SMILES: N=C(N)NC(=N)NCc1ccc2ccccc2c1 ; Cl]

The title compound (610 mg, 100%) in white solid was obtained according to the same method of Example 1, except that 2-naphthylmethylamine was used instead of 3,4-dichloro phenethylamine.

1H NMR (600 MHz, CD3OD) δ 7.94 (m, 4H), 7.53 (m, 3H), 4.74 (s, 2H)

LCMS: 242.1 (M+H+)

Example 46

N-1-(4-cyclopropyl-3-methyl)phenethylbiguanide hydrochloride

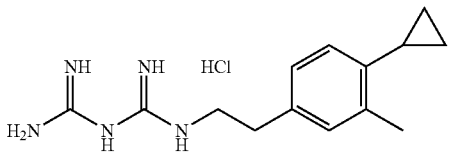 [SMILES: Cc1cc(CCNC(=N)NC(=N)N)ccc1C1CC1 ; Cl]

The title compound (60 mg, 7.1%) in white solid was obtained according to the same method of Example 1, except that (4-cyclopropyl-3-methyl)phenethylamine was used instead of 3,4-dichloro phenethylamine.

1H NMR (600 MHz, CD3OD) δ 7.05 (s, 1H), 7.02 (d, J=7.6 Hz, 1H), 6.93 (d, J=8.0 Hz, 1H), 3.55 (t, J=7.6 Hz, 2H), 2.89 (t, 2H), 2.40 (s, 3H), 1.88 (m, 1H), 0.93 (m, 2H), 0.55 (m, 2H) LCMS: 212.3 (M+H+)

Example 47

N-1-1-(3-(4-cyclopropylphenyl)propyl)biguanide hydrochloride

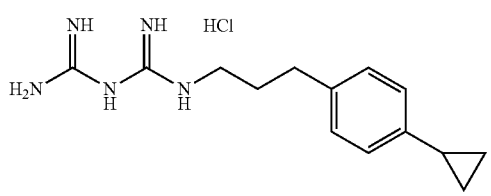 [SMILES: N=C(N)NC(=N)NCCCc1ccc(C2CC2)cc1 ; Cl]

The title compound (177 mg, 21.1%) in white solid was obtained according to the same method of Example 1, except that 3-(4-cyclopropylphenyl)propylamine was used instead of 3,4-dichloro phenethylamine.

1H NMR (600 MHz, CD3OD) δ 7.11 (d, J=6.0 Hz, 2H), 7.00 (d, J=7.8 Hz, 2H), 3.31 (m, 2H), 2.68 (t, J=7.8 Hz, 2H), 1.96 (m, 2H), 1.87 (m, 1H), 0.92 (m, 2H), 0.61 (m, 2H) LCMS: 260.2 (M+H+)

Example 48

N-1-2-(5,6,7,8-tetrahydronaphthalen-2-yl)meth-anebiguanide hydrochloride

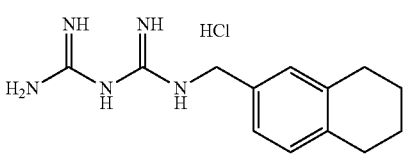 [SMILES: N=C(N)NC(=N)NCc1ccc2c(c1)CCCC2 ; Cl]

The title compound (151 mg, 36%) in white solid was obtained according to the same method of Example 1, except that (5,6,7,8-tetrahydronaphthalen-2-yl)methylamine was used instead of 3,4-dichloro phenethylamine.

1H NMR (600 MHz, DMSO) 7.04 (m, 3H), 4.33 (s, 2H), 2.69 (m, 4H), 1.72 (m, 4H) LCMS: 246.1 (M+H+)

Example 49

N-1-(4-phenyl)benzylbiguanide hydrochloride

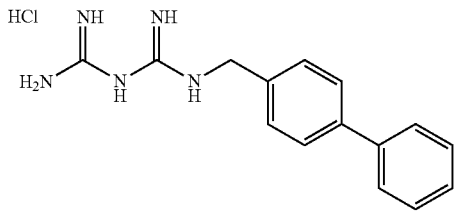 [SMILES: Cl ; N=C(N)NC(=N)NCc1ccc(-c2ccccc2)cc1]

The title compound (170 mg, 21.1%) in white solid was obtained according to the same method of Example 1, except that 4-phenyl benzylamine was used instead of 3,4-dichloro phenethylamine.

1H NMR (600 MHz, CD3OD) δ 7.68 (d, J=8.4 Hz, 2H), 7.62 (m, 2H), 7.51 (d, J=8.4 Hz, 2H), 7.44 (m, 2H), 7.34 (m, 1H), 4.62 (s, 2H) LCMS: 268.2 (M+H+)

Example 50

N-1-(3-chloro-4-methyl)phenethylbiguanide hydrochloride

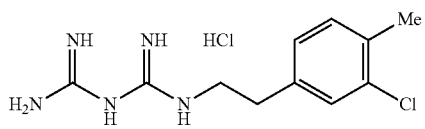 [SMILES: Cc1ccc(CCNC(=N)NC(=N)N)cc1Cl ; Cl]

The title compound (140 mg, 35%) in white solid was obtained according to the same method of Example 1, except that (3-chloro-4-methyl)phenethyl amine was used instead of 3,4-dichloro phenethylamine.

1H NMR (600 MHz, CD3OD) δ 7.33 (s, 1H), 7.26 (d, J=7.6 Hz, 1H), 7.15 (d, J=7.6 Hz, 1H), 3.59 (t, J=7.2 Hz, 2H), 2.94 (t, J=7.2 Hz, 2H), 2.33 (s, 3H)
LCMS: 254.1 (M+H+)

Example 51

N-1-(4-chloro-3-fluoro)phenethylbiguanide hydrochloride

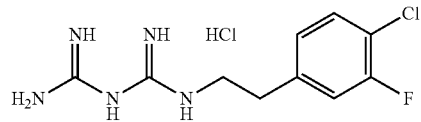 [SMILES: N=C(N)NC(=N)NCCc1ccc(Cl)c(F)c1 ; Cl]

The title compound (315 mg, 35%) in white solid was obtained according to the same method of Example 1, except that (4-chloro-3-fluoro)phenethyl amine was used instead of 3,4-dichloro phenethylamine.

1H NMR (600 MHz, DMSO-D6) δ 7.53 (t, J=7.2 Hz, 1H), 7.42 (s, 1H), 7.19 (d, J=7.2 Hz, 1H), 3.47 (bs, 2H), 2.87 (bs, 2H) LCMS: 258.1 (M+H+)

Example 52

N-1-(3-chloro-4-fluoro)phenethylbiguanide hydrochloride

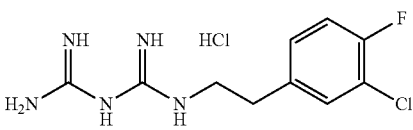

The title compound (188 mg, 21%) in white solid was obtained according to the same method of Example 1, except that (3-chloro-4-fluoro)phenethyl amine was used instead of 3,4-dichloro phenethylamine.

1H NMR (600 MHz, DMSO-D6) δ 7.57 (s, 1H), 7.35 (m, 2H), 3.44 (s, 2H), 2.84 (s, 2H) LCMS: 258.1 (M+H+)

Example 53

N-1-tert-butyl-N-5-phenethylbiguanide hydrochloride

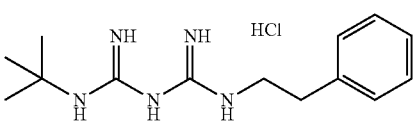 [SMILES: CC(C)(C)NC(=N)NC(=N)NCCc1ccccc1 ; Cl]

The title compound (200 mg, 94.9%) in white solid was obtained according to the same method of Example 1, except that phenethylamine was used instead of 3,4-dichloro phenethylamine and N-tert-butylcyanoguanide was used instead of cyanoguanide 1H NMR (600 MHz, CD3OD) δ 7.32 (m, 4H), 7.24 (m, 1H), 3.57 (s, 2H), 2.97 (s, 3H), 1.45 (s, 9H) LCMS: 262.2 [M+H]+

Example 54

N-1-tert-butyl-N-5-(3,4-dimethyl)benzylbiguanide hydrochloride

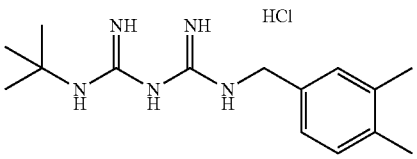 [SMILES: Cl ; Cc1ccc(CNC(=N)NC(=N)NC(C)(C)C)cc1C]

The title compound (660 mg, 96.6%) in white solid was obtained according to the same method of Example 1, except that 3,4-dimethyl benzylamine was used instead of 3,4-dichloro phenethylamine and N-tert-butylcyanoguanide was used instead of cyanoguanide.

1H NMR (600 MHz, CD3OD) δ 7.16 (s, 2H), 7.11 (s, 1H), 4.44 (s, 2H), 2.27 (s, 3H), 2.25 (s, 3H), 1.48 (s, 3H) LCMS: 276.2 [M+H]+

Example 55

N-1-(2-cyclopentyl)ethylbiguanide hydrochloride

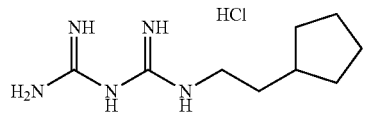 [SMILES: N=C(N)NC(=N)NCCC1CCCC1 ; Cl]

The title compound (320 mg, 97.3%) in white solid was obtained according to the same method of Example 1, except that (2-cyclopentyl)ethyl amine was used instead of 3,4-dichloro phenethylamine.

1H NMR (600 MHz, CD3OD) δ 3.35 (t, J=7.8 Hz, 2H), 1.89 (m, 1H), 1.87 (m, 2H), 1.72 (m, 2H), 1.59 (m, 2H), 1.18 (2H) LCMS: 198.2 [M+H]+

Example 56

N-1-(4-phenoxy)benzylbiguanide hydrochloride

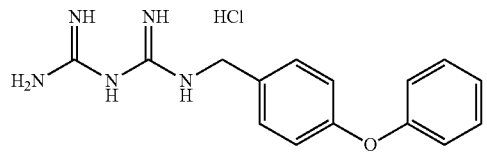 [SMILES: Cl ; N=C(N)NC(=N)NCc1ccc(Oc2ccccc2)cc1]

The title compound (420 mg, 97.4%) in white solid was obtained according to the same method of Example 1, except that (4-phenoxy)benzyl amine was used instead of 3,4-dichloro phenethylamine.

1H NMR (600 MHz, CD3OD) δ 8.21 (m, 1H), 7.39 (m, 2H), 7.34 (m, 2H), 7.14 (m, 1H), 7.01 (m, 3H), 4.36 (d, 2H) LCMS: 284.2 [M+H]+

Example 57

N-1-isopropyl-N-5-(4-chloro)phenethylbiguanide hydrochloride

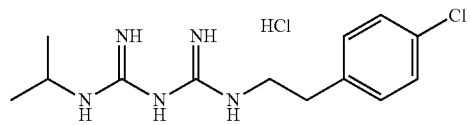 [SMILES: CC(C)NC(=N)NC(=N)NCCc1ccc(Cl)cc1 ; Cl]

The title compound (870 mg, 98.5%) in white solid was obtained according to the same method of Example 1, except that 4-chloro phenethylamine was used instead of 3,4-dichloro phenethylamine and N-tert-butylcyanoguanide was used instead of cyanoguanide.

1H NMR (600 MHz, CD3OD) δ 7.32 (s, 4H), 3.84 (m, 1H), 3.59 (t, J=7.8 HZ, 2H), 2.97 (t, J=7.2 Hz, 2H), 1.30 (d, J=6.6 Hz, 6H) LCMS: 282.2 [M+H]+

Example 58

N-1-isopropyl-N-5-phenethylbiguanide hydrochloride

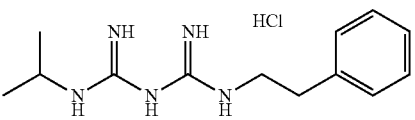 [SMILES: CC(C)NC(=N)NC(=N)NCCc1ccccc1 ; Cl]

The title compound (820 mg, 98.6%) in white solid was obtained according to the same method of Example 1, except that phenethylamine was used instead of 3,4-dichloro phenethylamine and N-tert-butylcyanoguanide was used instead of cyanoguanide.

1H NMR (600 MHz, CD3OD) δ 7.61 (d, J=7.2 Hz, 1H), 7.47 (d, J=7.8 Hz, 1H), 7.39 (t, J=7.8 Hz, 1H), 4.70 (s, 2H) LCMS: 260.0, 262.0 (M+H+)

Example 59

N-1-isopropyl-N-5-(4-chloro)benzylbiguanide hydrochloride

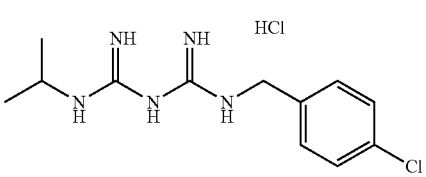 [SMILES: Cl ; CC(C)NC(=N)NC(=N)NCc1ccc(Cl)cc1]

The title compound (700 mg, 99.6%) in white solid was obtained according to the same method of Example 1, except that 4-chloro benzylamine was used instead of 3,4-dichloro phenethylamine and N-tert-butylcyanoguanide was used instead of cyanoguanide.

1H NMR (600 MHz, CD3OD) δ 6.90 (m, 2H), 6.85 (d, J=8.4 Hz, 1H), 5.97 (s, 2H), 4.45 (s, 2H) LCMS: 236.1 (M+H+)

Example 60

N-1-isopropyl-N-5-(3,4-dimethyl)phenethylbiguanide hydrochloride

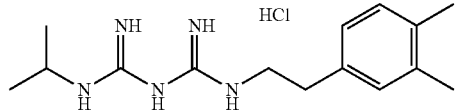 [SMILES: Cc1ccc(CCNC(=N)NC(=N)NC(C)C)cc1C ; Cl]

The title compound (460 mg, 99.2%) in white solid was obtained according to the same method of Example 1, except that 3,4-dimethyl phenethylamine was used instead of 3,4-dichloro phenethylamine and N-tert-butylcyanoguanide was used instead of cyanoguanide.

1H NMR (600 MHz, CD3OD) δ 7.07 (m, 2H), 7.00 (m, 1H), 3.83 (m, 1H), 3.54 (m, 2H), 2.89 (m, 2H), 2.25 (s, 3H), 2.22 (s, 3H), 1.29 (d, J=6.6 Hz, 6H)
LCMS: 276.2 [M+H]+

Example 61

N-1-(4-chloro-3-methyl)phenethylbiguanide hydrochloride

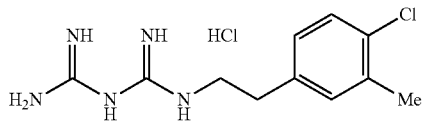 [SMILES: Cc1cc(CCNC(=N)NC(=N)N)ccc1Cl ; Cl]

The title compound (180 mg, 39%) in white solid was obtained according to the same method of Example 1, except that 4-chloro-3-methyl)phenethylamine was used instead of 3,4-dichloro phenethylamine.

1H NMR (400 MHz, DMSO-D6) δ 7.35 (d, J=8 Hz, 1H), 7.29 (s, 1H), 7.15 (d, J=8 Hz, 1H), 3.43 (bs, 2H), 2.80 (bs, 2H), 2.31 (s, 3H) LCMS: 254.1 (M+H+)

Example 62

N-1-(1-adamantyl)methylbiguanide hydrochloride

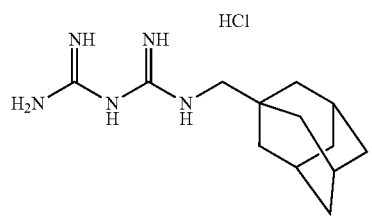 [SMILES: Cl ; N=C(N)NC(=N)NCC12CC3CC(CC(C3)C1)C2]

The title compound (560 mg, 97.6%) in white solid was obtained according to the same method of Example 1, except that (1-adamantyl)methylamine was used instead of 3,4-dichloro phenethylamine.

1H NMR (600 MHz, DMSO-D6) δ 9.21 (s, 0.5H), 9.05 (s, 1.5H), 8.52 (s, 3H), 7.55 (s, 1H), 2.99 (s, 2H), 1.94 (m, 3H), 1.60 (m, 6H), 1.52 (m, 5H)

LCMS: 250.2 [M+H]+

Example 63

N-1-tert-butyl-N-5-(3,4-dichloro)benzylbiguanide hydrochloride

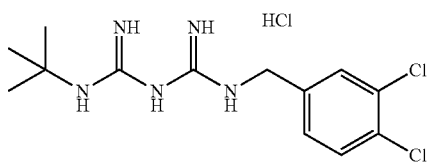 [SMILES: Cl ; CC(C)(C)NC(=N)NC(=N)NCc1ccc(Cl)c(Cl)c1]

The title compound (910 mg, 94.1%) in white solid was obtained according to the same method of Example 1, except that 3,4-dichloro benzylamine was used instead of 3,4-dichloro phenethylamine and N-tert-butylcyanoguanide was used instead of cyanoguanide.

1H NMR (400 MHz, DMSO-D6) δ 7.70 (m, 2H), 7.57 (s, 1H), 4.39 (s, 2H), 1.38 (s, 9H) LCMS: 316.2, 318.2 [M+H]+

Example 64

N-1-tert-butyl-N-5-(2-methyl)benzylbiguanide hydrochloride

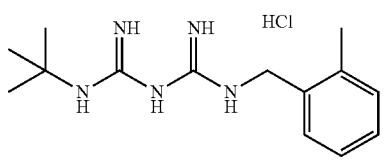 [SMILES: Cl ; Cc1ccccc1CNC(=N)NC(=N)NC(C)(C)C]

The title compound (320 mg, 96.5%) in white solid was obtained according to the same method of Example 1, except that 2-methylbenzylamine was used instead of 3,4-dichloro phenethylamine and N-tert-butylcyanoguanide was used instead of cyanoguanide.

1H NMR (600 MHz, CD3OD) δ 7.07.24 (s, 1H), 7.19 (s, 3H), 4.36 (s, 2H), 2.27 (s, 3H), 1.26 (s, 9H) LCMS: 262.2 [M+H]+

Example 65

N-1-(1-cyclohexyl)methylbiguanide hydrochloride

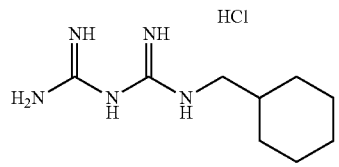 [SMILES: Cl ; N=C(N)NC(=N)NCC1CCCCC1]

The title compound (420 mg, 40.8%) in white solid was obtained according to the same method of Example 1, except that 1-cyclohexyl methylamine was used instead of 3,4-dichloro phenethylamine.

1H NMR (600 MHz, DMSO-D6) δ 9.43 (s, 0.5H), 9.04 (s, 1.5H), 8.50 (s, 3H), 7.69 (s, 1H), 3.08 (t, J=6.0 Hz, 2H), 1.70 (m, 6H), 1.17 (m, 3H), 0.95 (m, 2H)

LCMS: 198.2 [M+H]+

Example 66

N-1-2-(2,3-dihydro-1H-inden-5-yl)ethylbiguanide hydrochloride

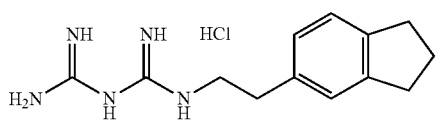 [SMILES: N=C(N)NC(=N)NCCc1ccc2c(c1)CCC2 ; Cl]

The title compound (150 mg, 48%) in white solid was obtained according to the same method of Example 1, except that (2,3-dihydro-1H-inden-5-yl)ethylamine was used instead of 3,4-dichloro phenethylamine.

1H NMR (400 MHz, DMSO-D6) 7.16 (m, 2H), 7.02 (d, J=7.2 Hz, 1H), 2.84 (m, 6H), 2.01 (m, 2H) LCMS: 246.2 (M+H+)

Example 67

N-1-tert-butyl-N-5-(2-(5,6,7,8-tetrahydronaphthalen-2-yl)methane)biguanide hydrochloride

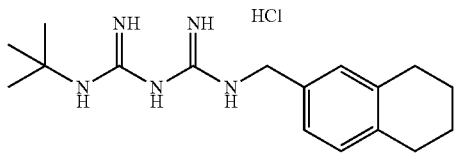 [SMILES: Cl ; CC(C)(C)NC(=N)NC(=N)NCc1ccc2c(c1)CCCC2]

The title compound (14 mg, 97.9%) in white solid was obtained according to the same method of Example 1, except that (5,6,7,8-tetrahydronaphthalen-2-yl)methylamine was used instead of 3,4-dichloro phenethylamine and N-tert-butylcyanoguanide was used instead of cyanoguanide.

1H NMR (400 MHz, DMSO-D6) δ 7.17 (m, 3H), 3.93 (s, 2H), 2.72 (s, 9H), 1.74 (s, 9H) LCMS: 302.2 [M+H]+

Example 68

N-1-(4-bromo-3-methyl)benzylbiguanide hydrochloride

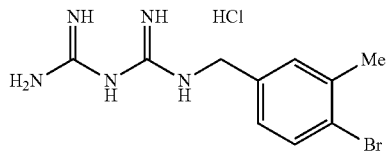 [SMILES: Cc1cc(CNC(=N)NC(=N)N)ccc1Br ; Cl]

The title compound (129 mg, 32%) in white solid was obtained according to the same method of Example 1, except that (4-bromo-3-methyl)benzylamine was used instead of 3,4-dichloro phenethylamine.

1H NMR (400 MHz, DMSO-D6) 7.59 (s, 1H), 7.37 (s, 1H), 7.15 (s, 1H), 4.40 (s, 2H), 2.34 (s, 3H) LCMS: 284.1 286.1 (M, M+2H+)

Example 69

N-1-(2,3-dihydrobenzo[b][1,4]dioxin-6-yl)phenethylbiguanide hydrochloride

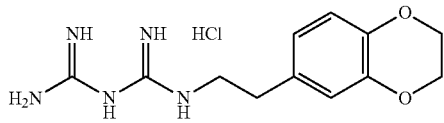 [SMILES: N=C(N)NC(=N)NCCc1ccc2c(c1)OCCO2 ; Cl]

The title compound (30 mg, 92%) in white solid was obtained according to the same method of Example 1, except that 2-(2,3-dihydrobenzo[b][1,4]dioxin-6-yl)ethanamine was used instead of 3,4-dichloro phenethylamine.

1H NMR (600 MHz, DMSO-D6) 6.78 (m, 2H), 6.73 (m, 1H), 4.24 (s, 4H), 3.37 (s, 2H), 2.50 (s, 2H); LCMS 264.2 [M+1]

Example 70

N-1-(3,4-dibromo)phenethylbiguanide hydrochloride

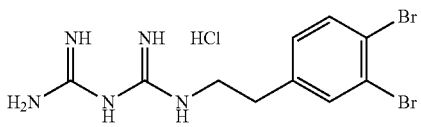 [SMILES: N=C(N)NC(=N)NCCc1ccc(Br)c(Br)c1 ; Cl]

The title compound (15 mg, 23%) in white solid was obtained according to the same method of Example 1, except that (3,4-dibromo)phenethyl amine was used instead of 3,4-dichloro phenethylamine.

1H NMR (600 MHz, DMSO-D6) 8.09 (s, 1H), 7.70 (d, J=7.8 Hz, 1H), 7.26 (d, J=7.8 Hz, 1H), 3.42 (s, 2H), 2.82 (s, 2H) LCMS 362.0 365.0

Example 71

N-1-(4-iodo)phenethylbiguanide hydrochloride

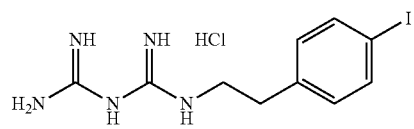 [SMILES: N=C(N)NC(=N)NCCc1ccc(I)cc1 ; Cl]

The title compound (45 mg, 23%) in white solid was obtained according to the same method of Example 1, except that (4-iodo)phenethyl amine was used instead of 3,4-dichloro phenethylamine.

1H NMR (600 MHz, DMSO-D6) 7.67 (d, J=8.4 Hz, 2H), 7.12 (d, J=8.4 Hz, 2H), 3.40 (s, 2H), 2.79 (s, 2H); LCMS 332.0 [M+1]

Example 72

N-1-(4-iodo-3-bromo)phenethylbiguanide hydrochloride

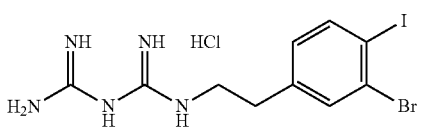 [SMILES: N=C(N)NC(=N)NCCc1ccc(I)c(Br)c1 ; Cl]

The title compound (66 mg, 60%) in white solid was obtained according to the same method of Example 1, except that (4-iodo-3-bromo)phenethyl amine was used instead of 3,4-dichloro phenethylamine.

1H NMR (600 MHz, DMSO-D6) 7.87 (d, J=7.8 Hz, 1H), 7.68 (s, 1H), 7.06 (s, 1H), 3.39 (s, 2H), 2.78 (s, 2H); LCMS 409.9 410.9 [M, M+2]

Example 73

N-1-(4-bromo-3-chloro)phenethylbiguanide hydrochloride

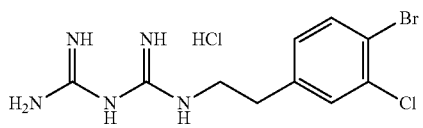 [SMILES: N=C(N)NC(=N)NCCc1ccc(Br)c(Cl)c1 ; Cl]

The title compound (140 mg, 53.8%) in white solid was obtained according to the same method of Example 1, except that (4-bromo-3-chloro)phenethyl amine was used instead of 3,4-dichloro phenethylamine.

1H NMR (600 MHz, DMSO-D6) 7.71 (d, J=12.6 Hz, 1H), 7.60 (s, 1H), 7.23 (d, J=12.6 Hz, 1H), 3.50 (s, 2H), 2.84 (s, 2H); LCMS 318.0 3208.0 [M, M+2]

Example 74

N-1-(3-iodo-4-chloro)phenethylbiguanide hydrochloride

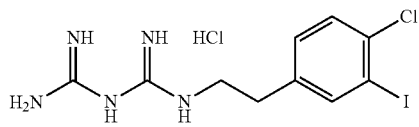 [SMILES: N=C(N)NC(=N)NCCc1ccc(Br)c(I)c1 ; Cl]

The title compound (77 mg, 62%) in white solid was obtained according to the same method of Example 1, except that (3-iodo-4-chloro)phenethyl amine was used instead of 3,4-dichloro phenethylamine.

1H NMR (600 MHz, DMSO-D6) 7.85 (s, 1H), 7.52 (d, J=8.4 Hz, 1H), 7.36 (s, 1H), 3.41 (s, 2H), 2.81 (s, 2H); LCMS 366.0 368.0 [M, M+2]

Example 75

N-1-(3-iodo-4-bromo)phenethylbiguanide hydrochloride

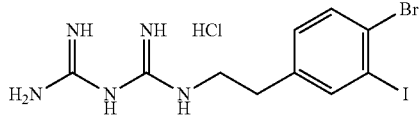

The title compound (60 mg, 16.3.%) in white solid was obtained according to the same method of Example 1, except that (3-iodo-4-bromo)phenethyl amine was used instead of 3,4-dichloro phenethylamine.

1H NMR (600 MHz, DMSO-D6) 7.91 (s, 1H), 7.64 (d, J=8.4 Hz, 1H), 7.28 (s, 1H), 3.44 (s, 2H), 2.80 (s, 2H); LCMS 409.9, 411.0 [M, M+2]

Example 76

N-1-(3-bromo-4-chloro)phenethylbiguanide hydrochloride

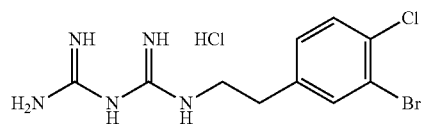

The title compound (72 mg, 56%) in white solid was obtained according to the same method of Example 1, except that (3-bromo-4-chloro)phenethyl amine was used instead of 3,4-dichloro phenethylamine.

1H NMR (600 MHz, DMSO-D6) 7.75 (s, 1H), 7.57 (d, J=7.8 Hz, 1H), 7.35 (s, 1H), 3.45 (s, 2H), 2.85 (s, 2H) LCMS 318.0 320

Example 77

N-1-(4-iodo-3-methoxy)phenethylbiguanide hydrochloride

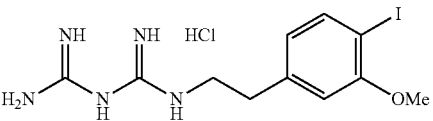 [SMILES: COc1cc(CCNC(=N)NC(=N)N)ccc1I ; Cl]

The title compound (168 mg, 69%) in white solid was obtained according to the same method of Example 1, except that (4-iodo-3-methoxy)phenethyl amine was used instead of 3,4-dichloro phenethylamine.

600 MHz DMSO 7.68 (d, J=7.8 Hz, 1H), 6.98 (S, 1H), 6.69 (s, 1H), 3.84 (s, 3H), 3.46 (s, 2H), 2.82 (s, 2H); LCMS 362.0 [M+1]

Example 78

N-1-(3-chloro-4-iodo)phenethylbiguanide hydrochloride

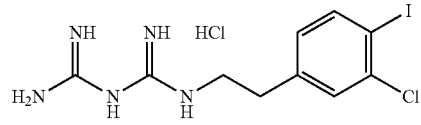 [SMILES: N=C(N)NC(=N)NCCc1ccc(I)c(Cl)c1 ; Cl]

The title compound (126 mg, 98%) in white solid was obtained according to the same method of Example 1, except that (3-chloro-4-iodo)phenethyl amine was used instead of 3,4-dichloro phenethylamine.

1H NMR (600 MHz, DMSO-D6) 7.87 (d, J=8.4 Hz, 1H), 7.55 (S, 1H), 7.03 (s, 1H), 3.42 (s, 2H), 2.81 (s, 2H) LCMS 366.0, 368.0 [M, M+2]

Example 79

N-1-(2-methoxy-4-iodo)phenethylbiguanide hydrochloride

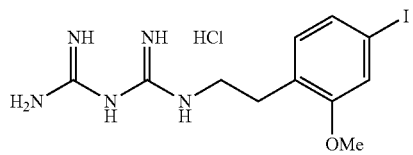 [SMILES: COc1cc(I)ccc1CCNC(=N)NC(=N)N ; Cl]

The title compound (70 mg, 57%) in white solid was obtained according to the same method of Example 1, except that (2-methoxy,4-iodo)phenethyl amine was used instead of 3,4-dichloro phenethylamine.

1H NMR (600 MHz, DMSO-D6) 7.27 (m, 2H), 7.00 (S, 1H), 3.80 (s, 3H), 3.32 (s, 2H), 2.75 (s, 2H); LCMS 362.0 [M+1]

Example 80

N-1-(2-methoxy-4-chloro)phenethylbiguanide hydrochloride

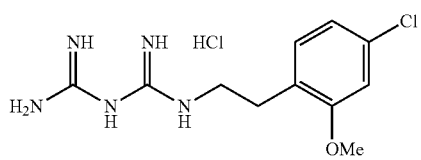 [SMILES: COc1cc(Cl)ccc1CCNC(=N)NC(=N)N ; Cl]

The title compound (25 mg, 18%) in white solid was obtained according to the same method of Example 1, except that (2-methoxy,4-chloro)phenethyl amine was used instead of 3,4-dichloro phenethylamine.

1H NMR (600 MHz, DMSO-D6) 7.22 (s, 1H), 7.05 (S, 1H), 6.96 (d, J=8.4 Hz, 1H), 3.82 (s, 3H), 3.3 (s, 2H), 2.76 (s, 2H); LCMS 270.1, 272.1 [M, M+2]

Example 81

N1-(2-methoxy-4-bromo)phenethylbiguanide hydrochloride

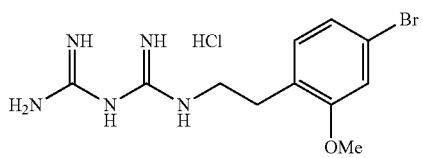 [SMILES: COc1cc(Br)ccc1CCNC(=N)NC(=N)N ; Cl]

The title compound (38 mg, 28%) in white solid was obtained according to the same method of Example 1, except that (2-methoxy,4-bromo)phenethyl amine was used instead of 3,4-dichloro phenethylamine.

1H NMR (600 MHz, DMSO-D6) 7.21 (s, 1H), 7.05 (S, 1H), 6.96 (d, J=7.8 Hz, 1H), 3.82 (s, 3H), 3.32 (s, 2H), 2.76 (s, 2H); LCMS 315.1, 317.1[M, M+2]

Example 82

N-1-2-(thiophen-2-ylmethyl) biguanide hydrochloride

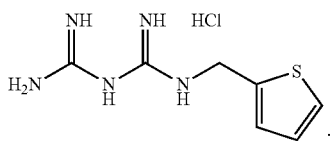 [SMILES: Cl ; N=C(N)NC(=N)NCc1cccs1]

The title compound (147 mg, 31%) in white solid was obtained according to the same method of Example 1, except that 2-thiophenemethylamine was used instead of 3,4-dichloro phenethylamine.

1H NMR (400 MHz, DMSO) δ 7.51 (m, 1H), 7.08 (m, 1H), 7.03 (m, 1H), 4.4 (s, 2H) LCMS: 198.1 (M+H+)

Example 83

N-1-(3,4-difluoro)benzylbiguanide hydrochloride

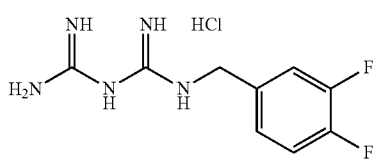 [SMILES: Cl ; N=C(N)NC(=N)NCc1ccc(F)c(F)c1]

The title compound (75 mg, 34%) in white solid was obtained according to the same method of Example 1, except that 3,4-difluorobenzyl amine was used instead of 3,4-dichloro phenethylamine.

1H NMR (400 MHz, DMSO) δ 7.47 (m, 2H), 7.37 (m, 2H), 4.98 (s, 2H) LCMS: 226.1 (M+H+)

Example 84

N-1-(3-phenylpropyl)biguanide hydrochloride

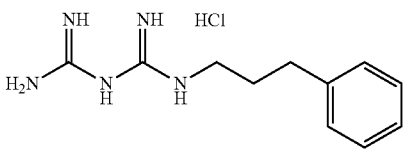 [SMILES: N=C(N)NC(=N)NCCCc1ccccc1 ; Cl]

The title compound (45 mg, 30%) in white solid was obtained according to the same method of Example 1, except that phenylpropylamine was used instead of 3,4-dichloro phenethylamine.

1H NMR (600 MHz, DMSO) δ 7.3 (t, J=7.8 Hz, 2H), 7.23 (d, J=7.8 Hz, 2H), 7.20 (t, J=7.8 Hz, 1H), 3.19 (bs, 2H), 2.64 (t, J=7.8 Hz, 2H) LCMS: 220 (M+H+)

Example 85

N-1-(4-fluoro-2-methyl)benzylbiguanide hydrochloride

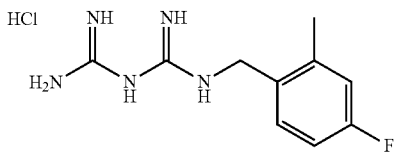 [SMILES: Cl ; Cc1cc(F)ccc1CNC(=N)NC(=N)N]

The title compound (390 mg, 42%) in white solid was obtained according to the same method of Example 1, except that (4-fluoro-2-methyl)benzyl amine was used instead of 3,4-dichloro phenethylamine.

1H NMR (600 MHz, DMSO) δ 7.27 (t, J=7.2 Hz, 1H), 7.14 (m, 1H), 7.08 (m, 1H), 4.39 (bs, 2H) LCMS: 224 (M+H+)

Example 86

N-1-(3-fluoro-4-methyl)benzylbiguanide hydrochloride

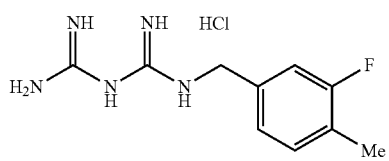 [SMILES: Cc1ccc(CNC(=N)NC(=N)N)cc1F ; Cl]

The title compound (59 mg, 32%) in white solid was obtained according to the same method of Example 1, except that (3-fluoro-4-methyl)benzyl amine was used instead of 3,4-dichloro phenethylamine.

1H NMR (600 MHz, DMSO) δ 7.27 (t, J=7.2 Hz, 1H), 7.14 (m, 1H), 7.08 (m, 1H), 4.39 (bs, 2H) LCMS: 224 (M+H+)

Example 87

N-1-(2,4,6-trifluoro)benzylbiguanide hydrochloride

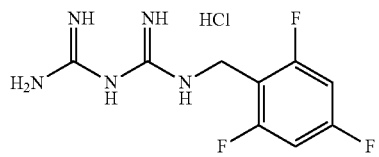 [SMILES: N=C(N)NC(=N)NCc1c(F)cc(F)cc1F ; Cl]

The title compound (68 mg, 12%) in white solid was obtained according to the same method of Example 1, except that (2,4,6-trifluoro)benzyl amine was used instead of 3,4-dichloro phenethylamine.

1H NMR (600 MHz, CD3OD) δ 7.24 (m, 2H), 4.36 (d, J=4.8 Hz, 2H)

LCMS: 246 (M+H+)

Example 88

N-1-(4-methyl)benzylbiguanide hydrochloride

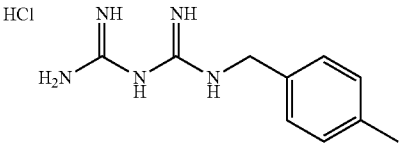

The title compound (530 mg, 53%) in white solid was obtained according to the same method of Example 1, except that 4-methylbenzylamine was used instead of 3,4-dichloro phenethylamine.

1H NMR (600 MHz, DMSO) δ 9.13 (brs, 1H), 8.40 (brs, 2H), 7.66 (m, 1H), 7.43 (m, 2H), 7.28 (m, 2H), 4.03 (s, 2H) LCMS: 270 (M+H+)

Example 89

N-1-(4-hydroxy-2-fluoro)benzylbiguanide hydrochloride

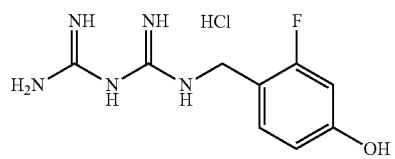 [SMILES: N=C(N)NC(=N)NCc1ccc(O)cc1F ; Cl]

The title compound (18.4 mg, 12.5%) in white solid was obtained according to the same method of Example 1, except that (4-hydroxy-2-fluoro)benzyl amine was used instead of 3,4-dichloro phenethylamine.

1H NMR (600 MHz, DMSO-d6) δ 9.73 (s, 1H), 9.28 (s, 2H), 8.62 (s, 3H), 7.34 (m, 1H), 6.94 (m, 1H), 6.92 (m, 1H), 3.52 (s, 2H), 3.08 (s, 2H)

LCMS: 212.0 [M+H]+

Example 90

N-1-(4-fluoro)phenylpropylbiguanide hydrochloride

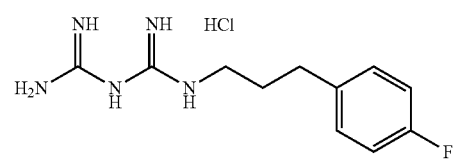 [SMILES: N=C(N)NC(=N)NCCCc1ccc(F)cc1 ; Cl]

The title compound (19.3 mg, 5.4%) in white solid was obtained according to the same method of Example 1, except that 3-(4-fluorophenyl)propane-1-amine was used instead of 3,4-dichloro phenethylamine.

1H NMR (600 MHz, CD3OD) δ 7.23 (m, 2H), 7.01 (m, 2H), 3.18 (t, 2H), 2.68 (t, 2H), 1.88 (q, 2H) LCMS: 238.2 [M+H]+

Example 91

N-1-(4-methoxy)phenylpropylbiguanide hydrochloride

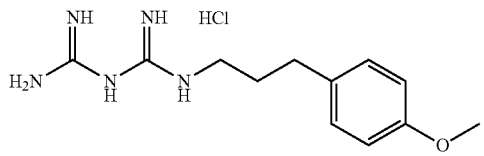 [SMILES: COc1ccc(CCCNC(=N)NC(=N)N)cc1 ; Cl]

The title compound (92 mg, 27%) in white solid was obtained according to the same method of Example 1, except that 3-(4-methoxyphenyl)propane-1-amine was used instead of 3,4-dichloro phenethylamine.

1H NMR (600 MHz, CD3OD) δ 7.14 (d, 2H), 6.85 (d, 2H), 3.18 (s, 2H), 2.57 (s, 2H), 2.50 (s, 3H), 1.98 (s, 2H) LCMS: 250.1 [M+H]+

Example 92

N-1-(2-iodo)benzylbiguanide hydrochloride

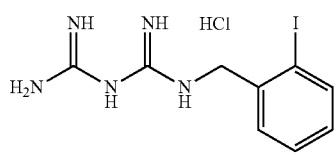 [SMILES: N=C(N)NC(=N)NCc1ccccc1I ; Cl]

The title compound (105 mg, 9%) in white solid was obtained according to the same method of Example 1, except that 2-iodobenzylamine was used instead of 3,4-dichloro phenethylamine.

1H NMR (600 MHz, CD3OD) δ 7.88 (m, 1H), 7.43 (s, 1H), 7.40 (s, 1H) 7.06 (s, 1H), 4.33 (s, 2H) LCMS: 318.0 [M+H]+

Example 93

N-1-(3-iodo)benzylbiguanide hydrochloride

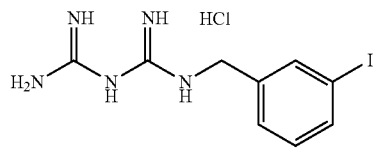 [SMILES: N=C(N)NC(=N)NCc1cccc(I)c1 ; Cl]

The title compound (116 mg, 29%) in white solid was obtained according to the same method of Example 1, except that 3-iodobenzylamine was used instead of 3,4-dichloro phenethylamine.

1H NMR (600 MHz, CD3OD) δ 7.88 (m, 1H), 7.43 (s, 1H), 7.40 (s, 1H) 7.06 (s, 1H), 4.33 (s, 2H) LCMS: 318.0 [M+H]+

Example 94

N-1-(4-fluoro)phenethyl-N-5-dimethylbiguanide hydrochloride

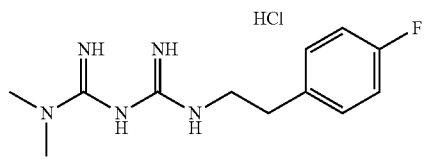 [SMILES: Cl ; CN(C)C(=N)NC(=N)NCCc1ccc(F)cc1]

The title compound (160 mg, 12.5%) in white solid was obtained according to the same method of Example 1, except that (4-fluoro)phenethylamine was used instead of 3,4-dichloro phenethylamine and N,N-dimethylcyanoguanide was used instead of cyanoguanide.

1H NMR (600 MHz, CD3OD) δ 7.28 (m, 2H), 7.11 (m, 2H), 3.34 (m, 2H), 2.94 (s, 6H), 2.77 (m, 2H) LCMS: 252.4 [M+H]+

Example 95

N-1-(2-phenyl)propane-N-5-dimethylbiguanide hydrochloride

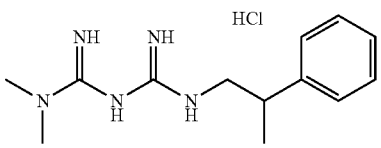 [SMILES: CC(CNC(=N)NC(=N)N(C)C)c1ccccc1 ; Cl]

2-phenyl-1-propanamine (3.0 g, 22.19 mmol) was dissolved in n-butanol (60 ml) at a room temperature. The solution was added by N,N-dimethylcyanoguanide (1.86 g, 22.19 mmol) and hydrochloride (1.93 ml, 22.19 mmol) and was agitated with reflux for 1 hour. The reaction product was distilled under vacuum and separated with a chromatograph using MC:MeOH=9:1. The product was dissolved in a small amount of methanol, agitated with addition of 12N hydrochloride (3.86 ml, 44.38 mmol), and was distilled under vacuum to the title compound in a white solid (2.2 g, 38.8%).

1H NMR (600 MHz, CD3OD) δ 7.29 (m, 5H), 3.65 (t, 2H), 3.00 (s, 6H), 2.89 (t, 2H), 2.71 (S, 3H) LCMS: 248.4 [M+H]+

Example 96

N-1-phenethyl-N-5-dimethylbiguanide hydrochloride

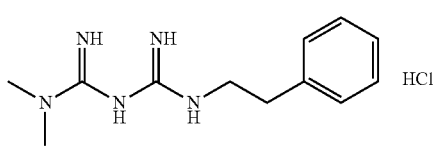 [SMILES: CN(C)C(=N)NC(=N)NCCc1ccccc1 ; Cl]

The title compound in white solid (1.1 g, yield: 66%) was obtained according to the same method of Example 95, except that phenethyl amine was used instead of 1-methyl-phenethyl amine.

1H NMR (600 MHz, DMSO-D6) δ 7.32 (m, 5H), 3.34 (s, 2H), 3.09 (s, 3H), 2.94 (s, 6H), 2.77 (s, 2H) LCMS: 234.2 [M+H]+

Example 97

N-1-(2-phenylprophyl)biguanide hydrochloride

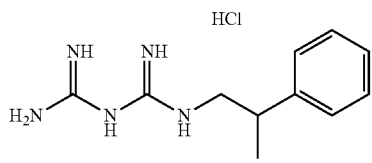 [SMILES: Cl ; CC(CNC(=N)NC(=N)N)c1ccccc1]

The title compound in white solid (220 mg, 15%) was obtained according to the same method of Example 95, except that cyanoguanid was used instead of N,N-dimethylcyanoguanide used in Example 95.

1H NMR (600 MHz, CD3OD) δ 7.31 (m, 4H), 7.23 (m, 1H), 3.58 (t, 2H), 3.11 (s, 3H), 3.04 (s, 6H), 2.97 (t, 2H) LCMS: 248.2 [M+H]+

Example 98

N-1-phenethyl-1-methyl-N-5-dimethylbiguanide hydrochloride

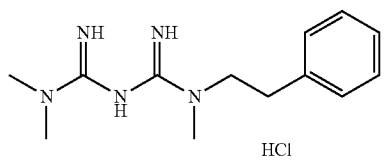 [SMILES: CN(C)C(=N)NC(=N)N(C)CCc1ccccc1 ; Cl]

The title compound in white solid (2.2 g, 38.8%) was obtained according to the same method of Example 95, except that 1-methyl-phenethyl amine was used instead of 2-phenyl-1-propanamine used in Example 95.

1H NMR (600 MHz, CD3OD) δ 7.29 (m, 5H), 3.65 (t, 2H), 3.00 (s, 6H), 2.89 (t, 2H), 2.71 (S, 3H) LCMS: 248.4 [M+H]+

Example 99

N-1-(4-fluoro)phenethyl-1-methylbiguanide hydrochloride

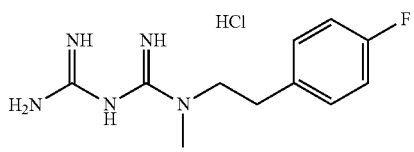 [SMILES: CN(CCc1ccc(F)cc1)C(=N)NC(=N)N ; Cl]

The title compound in white solid (170 mg, 30%) was obtained according to the same method of Example 95, except that cyanoguanide was used instead of N,N-dimethylcyanoguanidine, and 1-(4-fluoro)phenethyl-1-methyl amine was used instead of 2-phenyl-1-propanamine.

1H NMR (600 MHz, CD3OD) δ 7.29 (m, 5H), 3.65 (t, 2H), 3.00 (s, 6H), 2.89 (t, 2H), 2.71 (S, 3H) LCMS: 248.4 [M+H]+

Example 100

N-1-(4-fluoro)phenethyl-N-1-methyl-N-5-dimethyl-biguanide hydrochloride

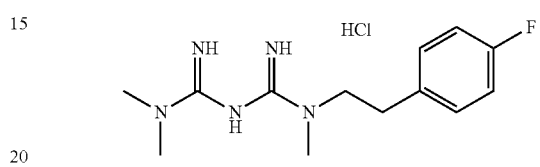

The title compound in white solid (380 mg, 49%) was obtained according to the same method of Example 1, except that 1-(4-fluoro)phenethyl-1-methyl amine was used instead of 2-phenyl-1-propanamine used in Example 95.

1H NMR (600 MHz, CD3OD) δ 7.29 (m, 4H), 3.40 (m, 2H), 3.31 (m, 2H), 3.0 (s, 6H), 1.27 (s, 3H) LCMS: 266.1 (M+H+)

Example 101

N-1-methyl-N-1-(4-methoxy)phenethylbiguanide hydrochloride

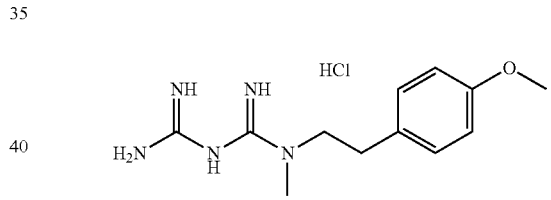

The title compound in white solid (50 mg, 5.8%) was obtained according to the same method of Example 95, except that cyanoguanide was used instead of N,N-dimethylcyanoguanidine, and 1-methyl-1-(4-methoxy)phenethyl-amine was used instead of 2-phenyl-1-propanamine used in Example 95.

1H NMR (600 MHz, CD3OD) δ 7.20 (m, 2H), 6.91 (m, 2H), 3.71 (s, 3H), 3.21 (d, J=7.8 Hz, 2H), 2.92 (d, J=7.8 Hz, 2H), 2.70 (s, 3H) LCMS: 220.1 (M+H+)

Example 102

N-1-(4-methoxy)phenethyl-1-methyl-N-5-dimethyl-biguanide hydrochloride

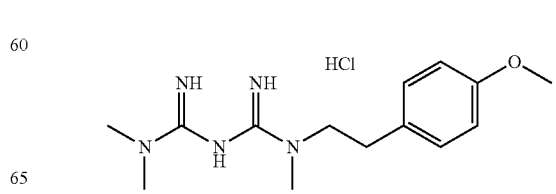

The title compound in white solid (410 mg, 49%) was obtained according to the same method of Example 95, except that 1-methyl-1-(4-methoxy)phenethylamine was used instead of 2-phenyl-1-propanamine.

1H NMR (600 MHz, CD3OD) δ 7.19 (d, 2H), 6.88 (d, 2H), 3.76 (s, 3H), 3.69 (t, 2H), 3.12 (s, 3H), 3.09 (s, 6H), 2.92 (t, 2H) LCMS: 278.4 [M+H]+

Example 103

N-1-(4-methoxy)phenethyl-N-5-dimethylbiguanide hydrochloride

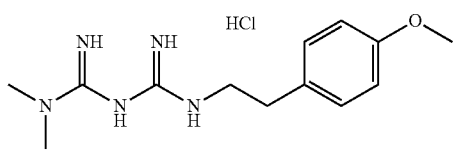

The title compound in white solid ((340 mg, 25%) was obtained according to the same method of Example 95, except that (4-methoxy)phenethylamine was used instead of 2-phenyl-1-propanamine.

1H NMR (600 MHz, CD3OD) δ 7.21 (m, 2H), 6.88 (m, 2H), 3.77 (s, 3H), 3.54 (m, 2H), 3.14 (s, 6H), 2.90 (s, 2H) LCMS: 264.5 [M+H]+

Example 104

N-1-(4-fluoro)phenethylbiguanide hydrochloride

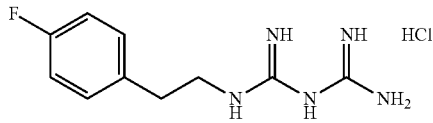 [SMILES: N=C(N)NC(=N)NCCc1ccc(F)cc1 ; Cl]

The title compound in white solid 238 mg, 64%) was obtained according to the same method of Example 95, except that cyanoguanide was used instead of N,N-dimethylcyanoguanidine and (4-fluoro)phenethylamine was used instead of 2-phenyl-1-propanamine.

1H NMR (600 MHz, CD3OD) δ 7.33 (t, 2H), 7.06 (t, 2H), 3.58 (t, 2H), 2.97 (t, 2H) LCMS: 224.1 [M+H]+

Example 105

N-1-methyl-N-1-phenethylbiguanide hydrochloride

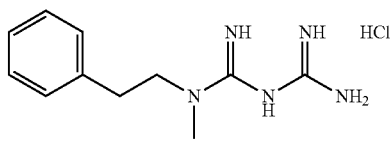 [SMILES: CN(CCc1ccccc1)C(=N)NC(=N)N ; Cl]

The title compound in white solid (0.12 g, 3.9%) was obtained according to the same method of Example 95, except that cyanoguanide was used instead of N,N-dimethylcyanoguanidine and 1-methyl-1-phenethylamine was used instead of 2-phenyl-1-propanamine.

1H NMR (600 MHz, DMSO-D6) δ 7.38 (m, 5H), 3.55 (m, 2H), 3.09 (s, 3H), 2.85 (m, 2H) LCMS: 220.2 [M+H]+

Example 106

N-1-(4-methoxy)phenethylbiguanide hydrochloride

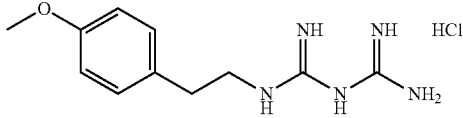 [SMILES: COc1ccc(CCNC(=N)NC(=N)N)cc1 ; Cl]

The title compound in white solid (635 mg, 83%) was obtained according to the same method of Example 95, except that cyanoguanide was used instead of N,N-dimethylcyanoguanidine and (4-methoxy)phenethylamine was used instead of 2-phenyl-1-propanamine.

1H NMR (600 MHz, DMSO-D6) δ 7.21 (m, 2H) 6.86 (m, 2H), 3.83 (s, 3H), 3.40 (s, 2H), 2.77 (s, 2H) LCMS: 236.2 [M+H]+

Example 107

N-1-phenethyl-N-2-methylbiguanide hydrochloride

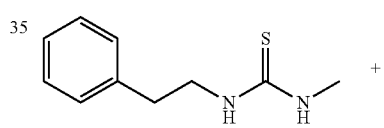

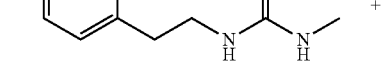

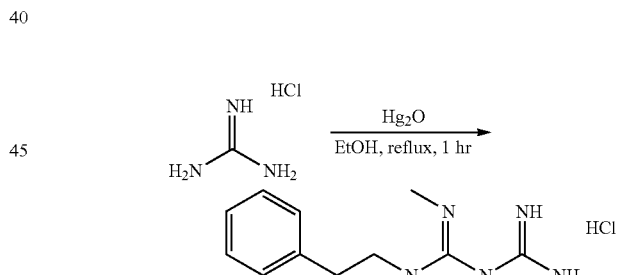

1-methyl-3-phenethylthiourea (1.6 g, 8.23 mmol) was dissolved in ethylalcohol (50 ml) at a room temperature. The solution was added by guanide hydrochloride (2.36 g, 24.70 mmol) and mercury oxide (3.57 g, 16.57 mmol) and was agitated with reflux for 1 hour. The reaction product was distilled under vacuum and separated with a chromatograph using MC:MeOH=9:1. The product was dissolved in a small amount of methanol, agitated with addition of 12N hydrochloride (1.5 ml, 16.46 mmol) and was distilled under vacuum to the title compound in a white solid (340 mg, 16.5%).

1H NMR (600 MHz, CD3OD) δ 7.37 (m, 4H), 7.24 (m, 1H), 3.60 (m, 2H), 3.01 (m, 5H) LCMS: 220.1 [M+H]+

Example 108

N-1-(2-(thiophen-2-yl)ethyl)-N-2-methylbiguanide hydrochloride

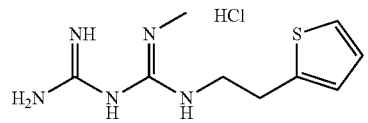

The title compound in white solid (100 mg, 28.3%) was obtained according to the same method of Example 107, except that 1-methyl-3-thiophenethylthiourea was used instead of 1-methyl-3-phenethylthiourea.

1H NMR (600 MHz, CD3OD) δ 7.27 (m, 3H), 3.68 (s, 2H), 3.31 (s, 3H), 3.04, s 2H) LCMS: 226.1 [M+H]+

Example 109

N-1-(2-(benzo[d][1,3]dioxol-5-yl)ethyl)-N-2-methylbiguanide hydrochloride

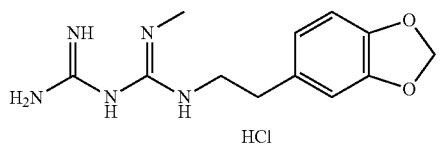 [SMILES: C/N=C(\NCCc1ccc2c(c1)OCO2)NC(=N)N ; Cl]

The title compound in white solid (200 mg, 53%) was obtained according to the same method of Example 107, except that 1-(2-(benzo[d][1,3]dioxol-4-yl)ethyl)-3-methylthiourea was used instead of 1-methyl-3-phenethylthiourea.

1H NMR (600 MHz, CD3OD) δ 6.74 (m, 2H), 6.68 (m, 1H), 5.90 (s, 2H), 3.40 (t, 2H), 2.79 (s, 3H), 2.77 (m, 2H) LCMS: 264.1 [M+H]+

Example 110

N-1-(2-(benzo[d][1,3]dioxol-5-yl)ethyl)-N-2-butylbiguanide hydrochloride

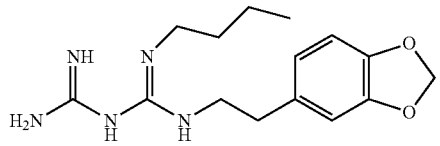

The title compound in white solid (180 mg, 47%) was obtained according to the same method of Example 107, except that 1-(2-(benzo[d][1,3]dioxol-4-yl)ethyl)-3-butylthiourea was used instead of 1-methyl-3-phenethylthiourea.

1H NMR (600 MHz, CD3OD) δ 6.74 (d, 2H), 6.69 (d, 1H), 5.90 (s, 2H), 3.39 (t, 2H), 3.15 (t, 2H), 2.77 (t, 2H), 1.51 (q, 2H), 1.35 (q, 2H), 0.94 (t, 3H)

LCMS: 306.2 [M+H]+

Example 111

N-1-(4-trifluoromethoxy)phenethyl-N-2-methylbiguanide hydrochloride

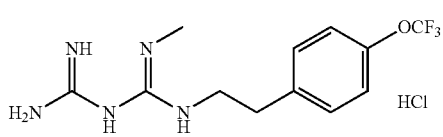 [SMILES: C/N=C(\NCCc1ccc(OC(F)(F)F)cc1)NC(=N)N ; Cl]

The title compound in white solid (247 mg, 29%) was obtained according to the same method of Example 107, except that 1-methyl-3-(4-trifluoromethoxy)phenethylthiourea was used instead of 1-methyl-3-phenethylthiourea.

1H NMR (600 MHz, CD3OD) δ 7.42 (d, 2H), 7.41 (d, 2H), 3.62 (s, 2H), 3.01 (m, 5H) LCMS: 304.1 [M+H]+

Example 112

N-1-(4-trifluoromethoxy)phenethyl-N-2-butylbiguanide hydrochloride

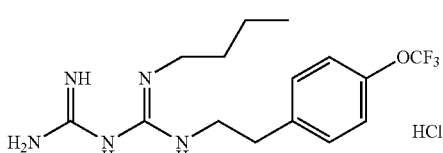

The title compound in white solid (348 mg, 36%) was obtained according to the same method of Example 107, except that 1-butyl-3-(4-trifluoromethoxy)phenethylthiourea was used instead of 1-methyl-3-phenethylthiourea.

1H NMR (600 MHz, CD3OD) δ 7.42 (d, 2H), 7.25 (d, 2H), 3.63 (t, 2H), 3.31 (m, 2H), 3.04 (t, 2H), 1.65 (q, 2H), 1.39 (q, 2H), 0.98 (t, 3H)

LCMS: 346.1 [M+H]+

Example 113

N-1-(4-trifluoromethyl)phenethyl-N-2-methylbiguanide hydrochloride

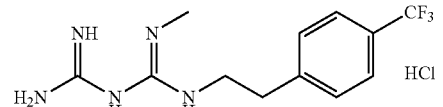

The title compound in white solid (122 mg, 37%) was obtained according to the same method of Example 107, except that 1-methyl-3-(4-trifluoro)phenethylthiourea was used instead of 1-methyl-3-phenethylthiourea.

1H NMR (600 MHz, CD3OD) δ 7.65 (d, 2H), 7.53 (d, 2H), 3.66 (s, 2H), 3.10 (t, 2H), 3.00 (s, 3H) LCMS: 288.1 [M+H]+

Example 114

N-1-(4-trifluoromethyl)phenethyl-N-2-butylbiguanide hydrochloride

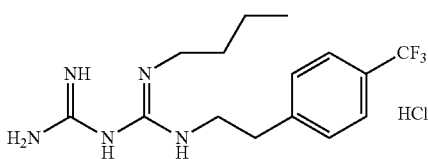 [SMILES: CCCC/N=C(\NCCc1ccc(C(F)(F)F)cc1)NC(=N)N ; Cl]

The title compound in white solid (155 mg, 40%) was obtained according to the same method of Example 107, except that 1-butyl-3-(4-trifluoro)phenethylthiourea was used instead of 1-methyl-3-phenethylthiourea.

1H NMR (600 MHz, CD3OD) δ 7.65 (d, 2H), 7.51 (d, 2H), 3.64 (t, 2H), 3.31 (m, 2H), 3.06 (t, 2H), 1.61 (q, 2H), 1.38 (q, 2H), 0.97 (t, 3H) LCMS: 330.2 [M+H]+

Example 115

N-1-phenethyl-N-1-methyl-N-2-methylbiguanide hydrochloride

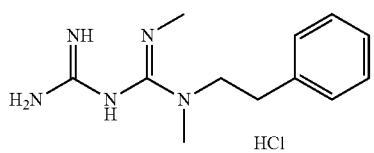 [SMILES: C/N=C(/NC(=N)N)N(C)CCc1ccccc1 ; Cl]

The title compound in white solid (105 mg, 25%) was obtained according to the same method of Example 107, except that 1-methyl-3-methyl-3-phenethylthiourea was used instead of 1-methyl-3-phenethylthiourea.

1H NMR (600 MHz, CD3OD) δ 7.29 (m, 2H), 7.23 (m, 3H), 3.60 (t, 2H), 2.89 (t, 2H), 2.96 (s, 3H), 2.82 (s, 3H) LCMS: 234.4 [M+H]+

Example 116

N-1-phenethyl-N-1-methyl-N-2-methyl-N-5-dimethylbiguanide hydrochloride

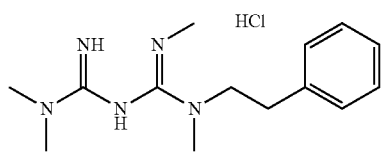 [SMILES: Cl ; C/N=C(/NC(=N)N(C)C)N(C)CCc1ccccc1]

The title compound in white solid (75 mg, 38.7%) was obtained according to the same method of Example 107, except that N,N-dimethyl guanide hydrochloride was used instead of guanide hydrochloride, and 1-methyl-3-methyl-3-phenethylthiourea was used instead of 1-methyl-3-phenethylthiourea 1H NMR (600 MHz, CD3OD) δ 7.33 (m, 2H), 7.25 (m, 3H), 3.62 (t, 2H), 3.11 (s, 6H), 3.09 (s, 3H), 2.94 (t, 2H), 2.81 (s, 3H) LCMS: 262.4 [M+H]+

Example 117

N-1-phenethyl-N-2-methyl-N-5-dimethylbiguanide hydrochloride

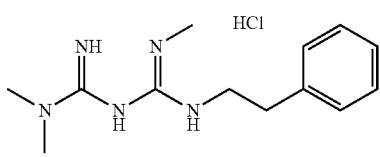 [SMILES: Cl ; C/N=C(\NCCc1ccccc1)NC(=N)N(C)C]

The title compound in white solid (200 mg, 37.7%) was obtained according to the same method of Example 107, except that N,N-dimethyl guanide hydrochloride was used instead of guanide hydrochloride, and 1-methyl-3-methyl-3-phenethylthiourea was used instead of 1-methyl-3-phenethylthiourea.

1H NMR (600 MHz, CD3OD) δ 7.31 (m, 4H), 7.23 (m, 1H), 3.58 (t, 2H), 3.11 (s, 3H), 3.04 (s, 6H), 2.97 (t, 2H) LCMS: 248.2 [M+H]+

Example 118

N2,N4-diphenethyl-1,3,5-triazine-2,4-diamine hydrochloride

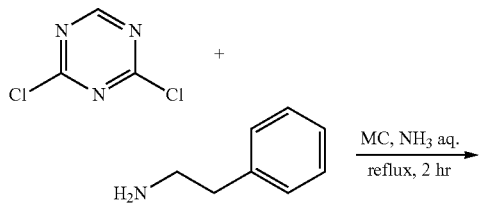

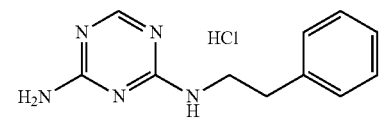

2,4-dichloro-1,3,5-triazine was dissolved in dichloromethane and was agitated at −10° C. for 10 minutes with addition of 1 equivalent of phenethylamine. 10° C. After the completion of reaction, the solvent was removed under vacuum and agitated with reflux in ammonium solution for 2 hours. After the completion of reaction, the solvent was removed under vacuum to obtain the title compound (94 mg, 33.5%).

1H NMR (600 MHz, DMSO-D6) 7.31 (t, J=7.3 Hz, 2H), 7.26 (t, J=7.3 Hz, 2H), 7.21 (t, J=7.3 Hz, 1H), 3.26 (t, J=7.3 Hz, 2H), 2.84 (t, J=7.3 Hz, 2H) LCMS: 204.1 (M+H+)

Example 119

N-2-phenethyl-1,3,5-triazine-2,4-diamine hydrochloride

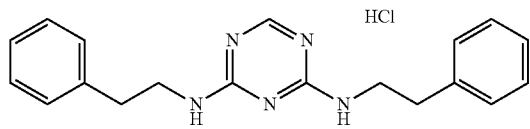 [SMILES: Cl ; c1ccc(CCNc2ncnc(NCCc3ccccc3)n2)cc1]

2,4-dichloro-1,3,5-triazine (0.5 g, 3.33 mmol) was dissolved in dichloromethane (10 ml)-10'C and agitated at −10'C for 10 minutes. Then, the reaction product was separated with chromatography using MC:MeOH=9:1 to produce the title compound in white sold (20 mg, 4.2%).

1H NMR (600 MHz, CD3OD) δ 7.35 (m, 4H), 7.27 (m, 6H), 3.16 (m, 4H), 2.94 (m, 4H) LCMS: 320.1 [M+H]+

Example 120

N-3-phenethyl-4H-1,2,4-triazole-3,5-diamine hydrochloride

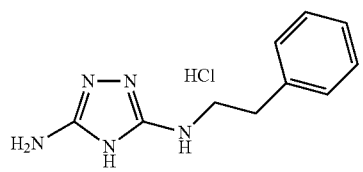 [SMILES: Nc1nnc(NCCc2ccccc2)[nH]1 ; Cl]

The title compound in white solid (42 mg, 15%) was obtained according to the same method of Example 118, except that 2,4-dichloro-1,2,4-triazole was used instead of 2,4-dichloro-1,3,5-triazine 1H NMR (600 MHz, DMSO-D6) 7.31 (t, J=7.3 Hz, 2H), 7.26 (t, J=7.3 Hz, 2H), 7.21 (t, J=7.3 Hz, 1H), 3.26 (t, J=7.3 Hz, 2H), 2.84 (t, J=7.3 Hz, 2H) LCMS: 204.1 (M+H+)

Example 121

N-3-(3,4-dichloro)phenethyl-4H-1,2,4-triazole-3,5-diamine hydrochloride

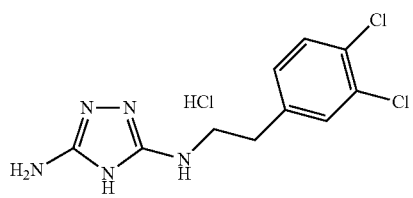 [SMILES: Nc1nnc(NCCc2ccc(Cl)c(Cl)c2)[nH]1 ; Cl]

The title compound in white solid (38 mg, 18%) was obtained according to the same method of Example 118, except that 2,4-dichloro-1,2,4-triazole was used instead of 2,4-dichloro-1,3,5-triazine and 3,4-dichloro phenethylamine was used instead of phenethylamine.

1H NMR (600 MHz, CD3OD) δ 7.05 (s, 1H), 7.02 (d, J=7.6 Hz, 1H), 6.93 (d, J=8.0 Hz, 1H), 3.55 (t, J=7.6 Hz, 2H), 2.89 (t, 2H), 2.40 (s, 3H), 1.88 (m, 1H), 0.93 (m, 2H), 0.55 (m, 2H) LCMS: 212.3 (M+H+)

Example 122

N-1-(3,4-dichloro)phenethyl-N5-methylbiguanide hydrochloride

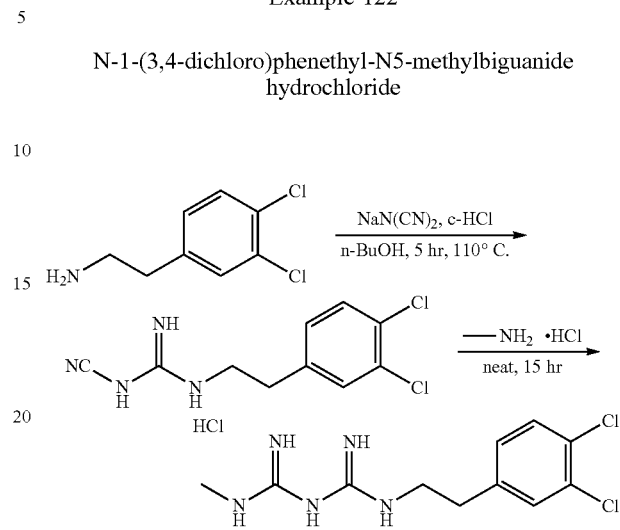

3,4-dichlorophenethyl amine (5.0 g, 26.31 mmol) was dissolved in n-butanol (100 ml), and agitated by reflux at 80° C. for 15 hours, with the addition of sodium dicyanamide (2.19 g, 26.31 mmol) and concentrate hydrochloride (2.29 ml, 26.31 mmol). After the reaction completed, the reaction was maintained at a room temperature and separated with water and ethylacetate. The organic layer was distilled under vacuum and then purified with chromatograph using MC:MeOH=9:1 to produce 3,4-dichlorophenethylcyanamide in white solid (2.2 g, 32.5%).

3,4-dichlorophenethylcyanamide (2.0 g, 7.78 mmol) and methylaminehydrochloride (0.58 g, 8.56 mmol) were added to flask at a room temperature and then were heated to 110~130° C. for 15 hour with agitation. The product was purified with chromatograph using MC:MeOH=9:1 to produce the title compound in white solid (0.53 g, 20.9%).

1H NMR (600 MHz, DMSO-D6) 7.64 (s, 1H), 7.58 (d, J=8.4 Hz, 1H), 7.34 (s, 1H), 3.47 (s, 2H), 2.81 (s, 2H), 2.61 (s, 3H); LCMS 288.1, 290.1 [M, M+2]

Example 123

N-1-methyl-N-5-benzylbiguanide hydrochloride

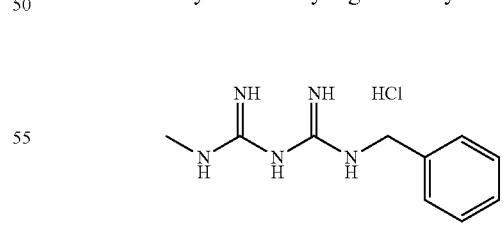

The title compound in white solid (60 mg, 18.8%) was obtained according to the same method of Example 122, except that benzylamine was used instead of 3,4-dichlorophenethyl amine.

1H NMR (600 MHz, DMSO-D6) δ 7.38 (m, 5H), 4.50 (s, 2H), 2.92 (s, 3H)

LCMS: 206.1 [M+H]+

Example 124

N-1-methyl-N-5-phenethylbiguanide hydrochloride

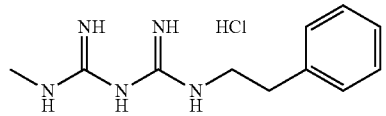 [SMILES: CNC(=N)NC(=N)NCCc1ccccc1 ; Cl]

The title compound in white solid (140 mg, 96.2%) was obtained according to the same method of Example 122, except that phenethylamine used instead of 3,4-dichlorophenethyl amine.

1H NMR (600 MHz, DMSO-D6) δ 7.31 (s, 4H), 7.22 (s, 1H), 3.46 (s, 2H), 2.82 (s, 5H) LCMS: 220.1 [M+H]+

Example 125

N-1-cyclohexyl-N-5-benzylbiguanide hydrochloride

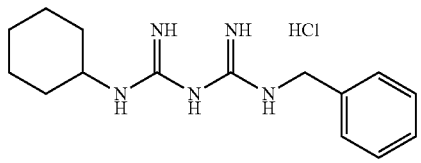 [SMILES: N=C(NCc1ccccc1)NC(=N)NC1CCCCC1 ; Cl]

The title compound in white solid (180 mg, 95.3%) was obtained according to the same method of Example 122, except that benzylamine was used instead of 3,4-dichlorophenethyl amine and cyclohexylamine was used instead of methylamine.

1H NMR (600 MHz, DMSO-D6) δ 7.37 (m, 5H), 4.48 (s, 2H), 3.48 (s, 1H), 1.84 (m, 4H), 1.24 (m, 4H) LCMS: 274.2 [M+H]+

Example 126

N-1-methyl-N-5-(2-(5,6,7,8-tetrahydronaphthalen-2-yl)ethyl) biguanide hydrochloride

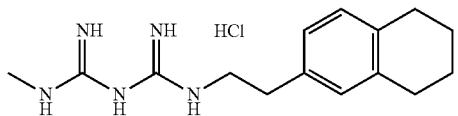 [SMILES: CNC(=N)NC(=N)NCCc1ccc2c(c1)CCCC2 ; Cl]

The title compound in white solid (160 mg, 97%) was obtained according to the same method of Example 122, except that (5,6,7,8-tetrahydronaphthalen-2-yl)methylamine was used instead of 3,4-dichlorophenethyl amine.

1H NMR (600 MHz, DMSO-D6) 9.25 (s, 1H), 9.84 (s, 2H), 6.98 (s, 3H), 3.40 (s, 2H), 2.80 (s, 2H), 2.76 (s, 2H), 2.68 (m, 5H), 1.72 (s, 4H); LCMS 274.2 [M+1]

Example 127

N-1-propyl-N-5-(2-(5,6,7,8-tetrahydronaphthalen-2-yl)ethyl) biguanide hydrochloride

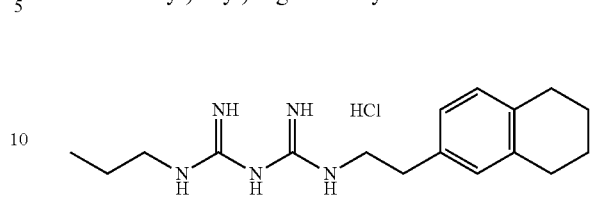

The title compound in white solid (30 mg, 99.6%) was obtained according to the same method of Example 122, except that (5,6,7,8-tetrahydronaphthalen-2-yl)methylamine was used instead of 3,4-dichlorophenethyl amine and propylamine was used instead of methylamine.

1H NMR (600 MHz, DMSO-D6) 6.97 (s, 3H), 3.36 (s, 2H), 3.12 (s, 2H), 2.73 (s, 2H), 2.67 (m, 4H), 1.71 (s, 4H), 1.51 (s, 2H), 0.89 (s, 3H); LCMS 302.1 [M+1]

Example 128

N-1-propyl-N-5-(3,4-dichloro)phenethylbiguanide hydrochloride

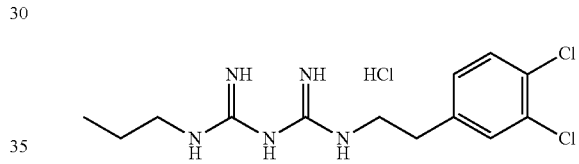

The title compound in white solid (30 mg, 99.6%) was obtained according to the same method of Example 122, except that propylamine was used instead of methylamine.

1H NMR (600 MHz, DMSO-D6) 9.33 (s, 1H), 9.01 (d, 2H), 7.65 (s, 1H), 7.57 (d, J=7.8 Hz, 1H), 7.35 (s, 1H), 3.49 (s, 2H), 3.18 (s, 2H), 2.88 (s, 2H), 1.54 (s, 2H), 0.90 (s, 3H); LCMS 316.1, 318.1 [M, M+2]

Example 129

N-1-methoxy-N-5-(3,4-dichloro)phenethylbiguanide hydrochloride

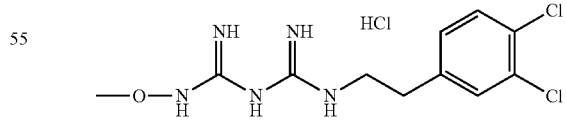

The title compound in white solid (190 mg, 47.5%) was obtained according to the same method of Example 122, except that methoxyamine was used instead of methylamine.

1H NMR (600 MHz, DMSO-D6) 8.31 (s, 1H), 7.62 (s, 1H), 7.58 (d, J=8.4 Hz, 1H), 7.31 (d, J=7.2 Hz, 1H), 6.21 (s, 1H), 3.57 (s, 2H), 3.33 (s, 3H), 2.84 (s, 2H)

LCMS 304.1, 306.1 [M, M+2]

Example 130

N-1-methyl-N-5-(4-ethyl)benzylbiguanide hydrochloride

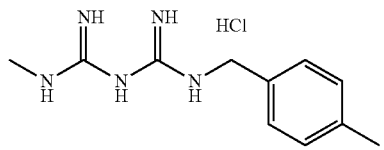

The title compound in white solid (32 mg, 3%) was obtained according to the same method of Example 122, except that 4-methylbenzylamine was used instead of 3,4-dichlorophenethyl amine.

1H NMR (600 MHz, DMSO-D6) 7.22 (m, 2H), 7.17 (d, J=7.8 Hz, 1H), 4.35 (s, 2H), 2.73 (s, 3H), 2.29 (s, 3H); LCMS 220.1 [M+1]

Example 131

4-methylsulfonyl-N—(N-(4-(trifluoromethoxy)phenyl)carbamimidoyl)piperidine-1-carboximidamide hydrochloride

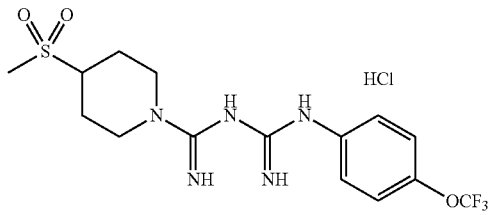 [SMILES: CS(=O)(=O)C1CCN(C(=N)NC(=N)Nc2ccc(OC(F)(F)F)cc2)CC1 ; Cl]

The title compound in white solid (150 mg, 53.3%) was obtained according to the same method of Example 122, except that 4-trifluoromethoxy aniline was used instead of methylamine and (4-methylsulphonyl)piperidine was used instead of 3,4-dichlorophenethyl amine.

1H NMR (600 MHz, CD3OD) δ 7.45 (d, 2H), 7.24 (d, 2H), 4.27 (d, 2H), 3.42 (m, 2H), 3.09 (m, 2H), 2.98 (s, 3H), 1.82 (m, 2H), 1.78 (m, 3H) LCMS: 408.1 [M+H]+

Example 132

N-1-methyl-N-2-methyl-N-5-(3,4-dichloro)phenethylbiguanide hydrochloride

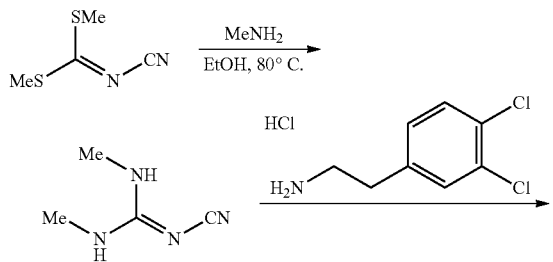

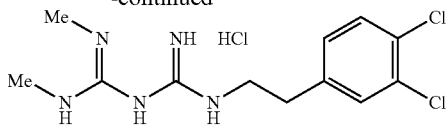

S,S'-Dimethyl N-Cyanodithioiminocarbonate (0.5 g, 3.42 mmol) was poured into seal tube and dissolved in ethanol (10 mL). 10 ml of 40% aqueous methylamine solution was added into the sea tube and agitated with reflux at 90° C. for 18 hours. After the reaction completed, the reaction product was concentrated under vacuum and solidified in 10 ml of dichloromethane to obtain the solid product. After filtering, the product was washed with 10 ml of dichloromethane and dried under vacuum to produce the title compound in white solid (255 mg, 66.5%).

2-cyano-1,3-dimethylguanidine (155 mg, 1.38 mmol), and 2-(3,4-dichlorophenyl)ethanamine hydrochloride (250 mg, 1.1 mmol) were added to flask and agitated for 2 hours at 160° C. After the reaction completed, the flask was cooled to room temperature and added by 20 ml of methanol. The reaction product was filtrated with glass filter and was washed with methanol 10 ml. The filtered solution was added by 40 ml of ethylacetate and 1 equivalent HCl to produce the solid product. The solid product was filtered, washed with ethylacetate and dried under vacuum to obtain the title compound in white solid (356 mg, 95.6%).

1H NMR (600 MHz, DMSO-D6) 7.57 (m, 2H), 7.28 (m, 1H), 3.40 (s, 2H), 2.8 (s, 2H), 2.72 (s, 6H); LCMS 302.1 304.1 [M, M+2]

Example 133

1-(3,4-dimethylphenethyl)guanide hydrochloride

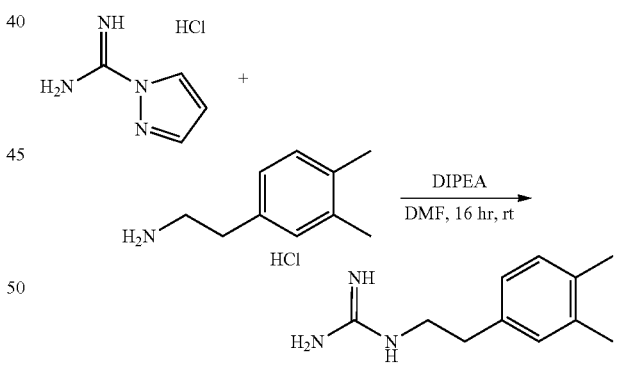

1-amindinoparazole hydrochloride (2.0 g, 13.4 mmol) and 3,4-Dimethylphenethylamine (1.96 g, 13.4 mmol) were dissolved in DMF 4 ml and were agitated with the addition of diisopropylethylamine (7 ml g, 4.02 mmol) at room temperature for 16 hours. After the reaction completed, the solvent was removed by vacuum distillation and extracted with water and methylene chloride. The water layer was distilled under vacuum and purified with chromatograph using MC:MeOH=9:1. The purified product was dissolved in a small amount of methanol and agitated with the addition of 12N HCl (0.9 ml, 10.46 mmol) at room temperature for 1 hour. Then, the product was added by ethylacetate 30 ml and agitated for 30 minutes. The produced solid was filtered, washed with ethylacetate and dried under vacuum to produce the title compound in white solid (0.85 g, 27.9%).

1H NMR (400 MHz, CD3OD) δ 7.06 (d, J=7.2 Hz, 1H), 6.99 (m, 2H), 3.39 (t, J=7.6 Hz, 2H), 2.85 (t, J=7.6 Hz, 2H), 2.29 (d, J=16 Hz, 6H) LCMS: 192 (M+H+)

Example 134

1-(phenethyl)guanide hydrochloride

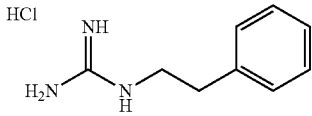 [SMILES: Cl ; N=C(N)NCCc1ccccc1]

The title compound in white solid (11 mg, 4%) was obtained according to the same method of Example 133, except that phenethylamine was used instead of Dimethylphenethylamine.

1H NMR (600 MHz, DMSO) δ 7.29 (t, J=7.8 Hz, 2H), 7.22 (d, J=7.8 Hz, 2H), 7.19 (t, J=7.8 Hz, 1H), 3.39 (t, J=7.2 Hz, 2H), 2.93 (d, J=7.2 Hz, 2H)

LCMS: 164.1 (M+H+)

Example 135

1-(4-trifluoromethoxyphenethyl)guanide hydrochloride

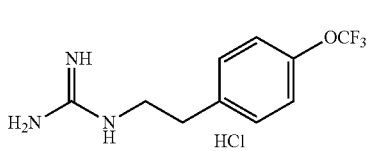 [SMILES: N=C(N)NCCc1ccc(OC(F)(F)F)cc1 ; Cl]

The title compound in white solid (259 mg, 78.7%) was obtained according to the same method of Example 133, except that 4-trifluoromethoxyphenethylamine was used instead of Dimethylphenethylamine.

1H NMR (600 MHz, DMSO) δ 7.62 (s, 1H), 7.41 (d, J=7.2 Hz, 2H), 7.32 (d, J=7.2 Hz, 2H), 3.38 (q, J=7.2 Hz, 2H), 2.82 (t, J=7.2 Hz, 2H) LCMS: 248 (M+H+)

Example 136 isoindolin-2-carboimidamide hydrochloride

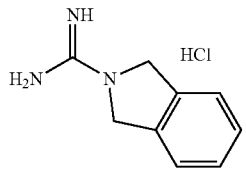 [SMILES: N=C(N)N1Cc2ccccc2C1 ; Cl]

The title compound in white solid (400 mg, 60.6%) was obtained according to the same method of Example 133, except that isoindole was used instead of Dimethylphenethylamine.

1H NMR (600 MHz, CD3OD) δ 7.41 (s, 4H), 5.12 (s, 1H), 4.96 (s, 1H)

LCMS: 204 (M+H+)

Example 137

1-(2,3-dihydro-1H-inden-2-yl)guanide hydrochloride

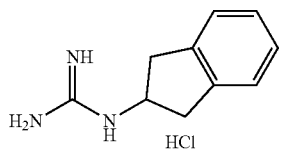 [SMILES: N=C(N)NC1Cc2ccccc2C1 ; Cl]

The title compound in white solid (276 mg, 64%) was obtained according to the same method of Example 133, except that 2-aminoindan was used instead of Dimethylphenethylamine.

1H NMR (400 MHz, DMSO) δ 8.16 (s, 1H), 7.26 (m, 2H), 7.17 (m, 2H), 4.33 (m, 1H), 3.28 (m, 2H), 2.82 (m, 2H) LCMS: 176 (M+H+)

Example 138

1-(4-methylphenethyl)guanide hydrochloride

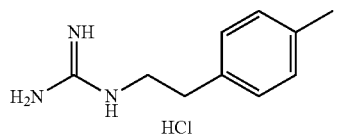

The title compound in white solid (307 mg, 70.5%) was obtained according to the same method of Example 133, except that 4-methylphenethylamine was used instead of Dimethylphenethylamine.

1H NMR (400 MHz, DMSO) δ 7.16 (q, J=8 Hz, 4H), 3.33 (t, J=7.2 Hz, 2H), 2.74 (t, J=7.2 Hz, 2H), 2.26 (s, 3H) LCMS: 178 (M+H+)

Example 139

1-(2-chlorophenethyl)guanide hydrochloride

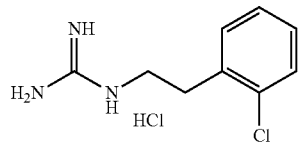 [SMILES: N=C(N)NCCc1ccccc1Cl ; Cl]

The title compound in white solid (400 mg, 83.8%) was obtained according to the same method of Example 133, except that 2-chlorophenethylamine was used instead of Dimethylphenethylamine.

1H NMR (400 MHz, DMSO) δ 7.81 (m, 1H), 7.49 (m, 2H), 7.28 (m, 2H), 3.39 (t, J=7.2 Hz, 2H), 2.93 (d, J=7.2 Hz, 2H) LCMS: 198 (M+H+)

Example 140

1-(3,4-dichlorophenethyl)guanide hydrochloride

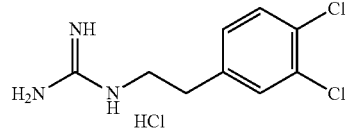 [SMILES: N=C(N)NCCc1ccc(Cl)c(Cl)c1 ; Cl]

The title compound in white solid (300 mg, 54.9%) was obtained according to the same method of Example 133, except that 3,4-dichlorophenethylamine was used instead of Dimethylphenethylamine.

1H NMR (400 MHz, DMSO) δ 7.69 (m, 1H), 7.60 (d, J=2 Hz, 1H), 7.59 (d, J=8.4 Hz, 1H), 7.30 (d, J=8.4 Hz, 1H), 3.38 (t, J=7.2 Hz, 2H), 2.80 (t, J=7.2 Hz, 2H LCMS: 232 (M+H+)

Example 141

1-(4-fluorophenethyl)guanide hydrochloride

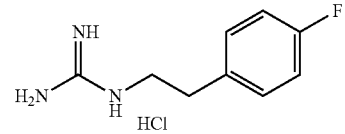 [SMILES: N=C(N)NCCc1ccc(F)cc1 ; Cl]

The title compound in white solid (324 mg, 73%) was obtained according to the same method of Example 133, except that 4-fluorophenethylamine was used instead of Dimethylphenethylamine.

1H NMR (400 MHz, DMSO) δ 7.77 (m, 1H), 7.34 (m, 2H), 7.15 (m, 1H), 3.35 (t, J=7.6 Hz, 2H), 2.78 (t, J=7.6 Hz, 2H) LCMS: 182 (M+H+)

Example 142

1-(2-fluorophenethyl)guanide hydrochloride

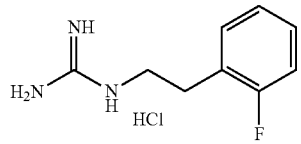 [SMILES: N=C(N)NCCc1ccccc1F ; Cl]

The title compound in white solid (356 mg, 80%) was obtained according to the same method of Example 133, except that 2-fluorophenethylamine was used instead of Dimethylphenethylamine.

1H NMR (400 MHz, DMSO) δ 7.80 (m, 1H), 7.41 (m, 1H), 7.32 (m, 1H), 7.19 (m, 2H), 3.37 (t, J=7.2 Hz, 2H), 2.83 (t, J=7.2 Hz, 2H) LCMS: 182 (M+H+)

Example 143

1-(thiopen-2-yl-ethyl)guanide hydrochloride

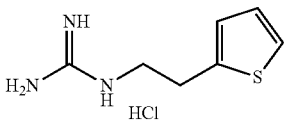 [SMILES: N=C(N)NCCc1cccs1 ; Cl]

The title compound in white solid (321 mg, 76.7%) was obtained according to the same method of Example 133, except that 2-thiophenethylamine was used instead of Dimethylphenethylamine.

1H NMR (400 MHz, DMSO) δ 7.81 (m, 1H), 7.38 (d, J=4.4 Hz, 1H), 6.98 (m, 2H), 3.41 (q, J=7.2 Hz, 2H), 3.01 (t, J=7.2 Hz, 2H) LCMS: 170 (M+H+)

Example 144

1-(thiopen-2-yl-methyl)guanide hydrochloride

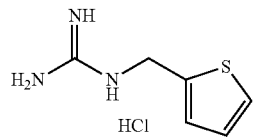

The title compound in white solid (323 mg, 83%) was obtained according to the same method of Example 133, except that (thiopen-2-yl-methyl)amine was used instead of Dimethylphenethylamine.

1H NMR (400 MHz, DMSO) δ 749 (m, 1H), 7.09 (m, 1H), 7.02 (m, 1H), 4.57 (s, 2H) LCMS: 156 (M+H+)

Example 145

1-(1,3-benzodioxol-5-ylmethyl)guanide hydrochloride

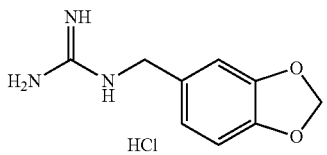 [SMILES: N=C(N)NCc1ccc2c(c1)OCO2 ; Cl]

The title compound in white solid (319 mg, 49%) was obtained according to the same method of Example 133, except that piperonylamine was used instead of Dimethylphenethylamine.

1H NMR (400 MHz, DMSO) δ 6.91 (m, 2H), 6.81 (d, J=6.8 Hz, 1H), 6.00 (s, 2H), 4.27 (s, 2H) LCMS: 194 (M+H+)

Example 146

1-(1,3-benzodioxol-5-ylethyl)guanide hydrochloride

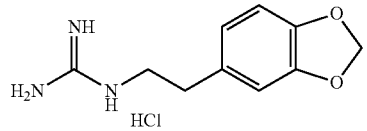 [SMILES: N=C(N)NCCc1ccc2c(c1)OCO2 ; Cl]

The title compound in white solid (409 mg, 49%) was obtained according to the same method of Example 133, except that homopiperonylamine was used instead of Dimethylphenethylamine.

1H NMR (400 MHz, DMSO) δ 6.89 (s, 1H), 6.85 (d, J=8 Hz, 1H), 6.73 (d, J=8 Hz, 1H), 5.97 (s, 2H), 3.30 (t, J=7.6 Hz, 2H), 2.70 (t, J=7.6 Hz, 2H)

LCMS: 208 (M+H+)

Example 147

1-(4-phenoxyphenethyl)guanide hydrochloride

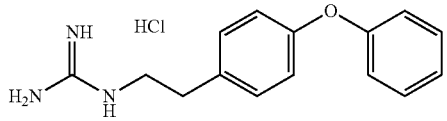 [SMILES: N=C(N)NCCc1ccc(Oc2ccccc2)cc1 ; Cl]

The title compound in white (350 mg, 73%) was obtained according to the same method of Example 133, except that 4-phenoxyphenethyl amine was used instead of Dimethylphenethylamine.

H NMR (400 MHz, CD3OD) δ 7.35 (m, 2H), 7.26 (m, 2H), 7.11 (m, 1H), 6.96 (m, 3H), 3.45 (t, J=6.8 Hz, 2H), 7.2 Hz, 2H) LCMS: 256 (M+H+)

Example 148

1-(4-isopropylphenethyl)guanide hydrochloride

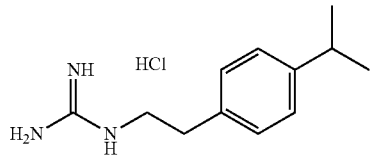

The title compound in white (220 mg, 61%) was obtained according to the same method of Example 133, except that 4-isopropylphenethyl amine was used instead of Dimethylphenethylamine.

1H NMR (400 MHz, CD3OD) δ 7.20 (s, 4H), 3.43 (t, 2H), 2.86 (m, 3H), 1.23 (d, J=6.8 Hz, 6H) LCMS: 206 (M+H+)

Example 149

1-(benzyloxy)guanide hydrochloride

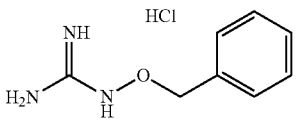

The title compound in white (12 mg, 9.1%) was obtained according to the same method of Example 133, except that O-benzylhydroxylamine was used instead of Dimethylphenethylamine.

1H NMR (600 MHz, CD3OD) δ 7.44 (m, 2H), 7.38 (m, 3H), 1.38 (m, 2H)

LCMS: 166.2 [M+H]+

Example 150

1-(3,4-dichlorobenzyl)guanide hydrochloride

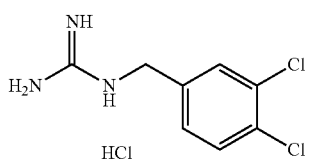 [SMILES: N=C(N)NCc1ccc(Cl)c(Cl)c1 ; Cl]

The title compound in white (270 mg, 52%) was obtained according to the same method of Example 133, except that 3,4-dichlorobenzylamine was used instead of Dimethylphenethylamine.

1H NMR (600 MHz, DMSO) δ 8.27 (m, 1H), 7.66 (d, J=8.4 Hz, 1H), 7.58 (s, 1H), 7.31 (d, J=8.4 Hz, 1H), 4.41 (s, 2H) LCMS: 218 (M+H+)

Example 151

1-(4-methylbenzyl)guanide hydrochloride

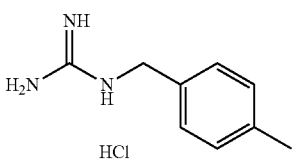

The title compound in white (190 mg, 38%) was obtained according to the same method of Example 133, except that 4-methylbenzylamine was used instead of Dimethylphenethylamine.

1H NMR (600 MHz, DMSO) δ 8.16 (m, 1H), 7.37 (t, J=8.4 Hz, 4H), 4.33 (s, 2H), 2.29 (s, 3H) LCMS: 164 (M+H+)

Example 152

1-(4-methoxy-3-trifluoromethylbenzyl)guanide hydrochloride

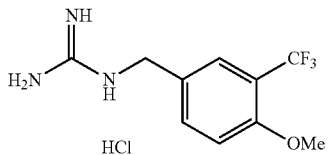 [SMILES: COc1ccc(CNC(=N)N)cc1C(F)(F)F ; Cl]

The title compound in white (280 mg, 49%) was obtained according to the same method of Example 133, except that 4-methoxy-3-trifluoromethylbenzyl amine was used instead of Dimethylphenethylamine.

1H NMR (600 MHz, DMSO) δ 8.23 (m, 1H), 7.59 (m, 2H), 7.29 (m, 1H), 4.38 (d, J=6 Hz, 2H), 3.88 (s, 3H) LCMS: 248 (M+H+)

Example 153

1-(2,4,6-trifluorobenzyl)guanide hydrochloride

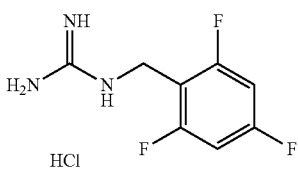 [SMILES: N=C(N)NCc1c(F)cc(F)cc1F ; Cl]

The title compound in white (130 mg, 26%) was obtained according to the same method of Example 133, except that 2,4,6-trifluorobenzyl amine was used instead of Dimethylphenethylamine.

1H NMR (600 MHz, DMSO) δ 8.11 (m, 1H), 7.28 (t, J=8.4 Hz, 2H), 4.39 (d, J=5.4 Hz, 2H) LCMS: 204 (M+H+)

Example 154

1-(3,4-difluorobenzyl)guanide hydrochloride

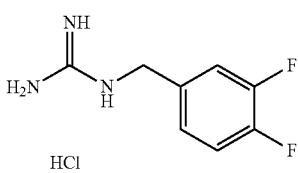 [SMILES: N=C(N)NCc1ccc(F)c(F)c1 ; Cl]

The title compound in white (40 mg, 9%) was obtained according to the same method of Example 133, except that 3,4-difluorobenzyl amine was used instead of Dimethylphenethylamine.

1H NMR (600 MHz, DMSO) δ 8.18 (s, 1H), 7.48 (m, 1H), 7.40 (m, 1H), 7.18 (m, 1H), 4.37 (s, 2H) LCMS: 186 (M+H+)

Example 155

1-(2,4-dimethylphenethyl)guanide hydrochloride

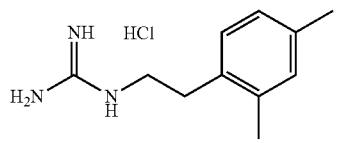

The title compound in white (380 mg, 62.3%) was obtained according to the same method of Example 133, except that 2,4-dimethylphenethyl amine was used instead of Dimethylphenethylamine.

1H NMR (400 MHz, CD3OD) δ 7.05 (m, 2H), 6.97 (m, 2H), 6.41 (t, J=6.8 Hz, 2H), 2.80 (t, J=6.8 Hz, 2H), 2.24 (d, J=9.2 Hz, 6H) LCMS: 192 (M+H+)

Example 156

1-(thiophen-2-ylmethoxy)guanide hydrochloride

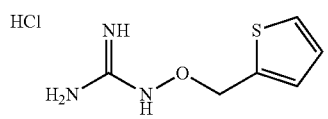 [SMILES: Cl ; N=C(N)NOCc1cccs1]

The title compound in white (380 mg, 62.3%) was obtained according to the same method of Example 133, except that O-(thiophen-2-ylmethyl)hydroxylamine was used instead of Dimethylphenethylamine.

1H NMR (600 MHz, DMSO-d6) δ 6.52 (d, 2H), 6.44 (m, 2H), 3.63 (s, 2H)

LCMS: 172.1 [M+H]+

Example 157

1-(benzo[d][1,3]dioxol-5-ylmethoxy)guanide hydrochloride

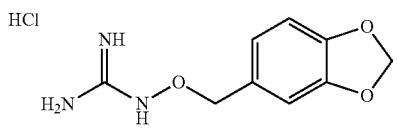 [SMILES: Cl ; N=C(N)NOCc1ccc2c(c1)OCO2]

The title compound in white (12 mg, 1%) was obtained according to the same method of Example 133, except that O-(benzo[d][1,3]dioxol-5-ylmethyl)hydroxylamine was used instead of Dimethylphenethylamine.

1H NMR (400 MHz, DMSO-d6) δ 6.85 (m, 2H), 6.77 (m, 2H), 5.96 (m, 2H), 4.45 (m, 2H) LCMS: 210.1 [M+H]+

Example 158

1-(2-(5-methyl-2-nitro-1H-imidazol-1-yl)ethyl)guanide hydrochloride

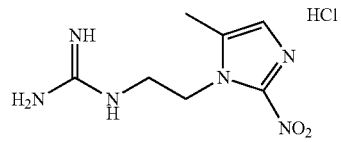

The title compound in white (4.09 mg, 5.6%) was obtained according to the same method of Example 133, except that 2-(4-methyl-2-nitro-1H-imidazol-1-yl)ethanamine was used instead of Dimethylphenethylamine.

1H NMR (600 MHz, CD3OD) δ 7.95 (s, 1H), 7.49 (m, 1H), 7.36 (m, 3H), 4.45 (d, J=6.0 Hz, 2H) LCMS: 184.1 (M+H+)

Example 159

1-(perfluorophenethyl)guanide hydrochloride

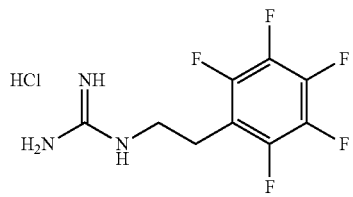 [SMILES: Cl ; N=C(N)NCCc1c(F)c(F)c(F)c(F)c1F]

The title compound in white (14.5 mg, 13%) was obtained according to the same method of Example 133, except that 2-(perfluorophenyl)ethanamine was used instead of Dimethylphenethylamine.

1H NMR (600 MHz, CD3OD) δ 3.50 (t, J=6 Hz, 2H), 3.03 (t, J=6 Hz, 2H)
LCMS: 254 (M+H+)

Example 160

1-(2-chlorobenzyl)guanide hydrochloride

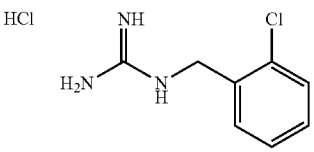 [SMILES: Cl ; N=C(N)NCc1ccccc1Cl]

The title compound in white (8 mg, 13%) was obtained according to the same method of Example 133, except that 2-chlorobenzyl amine was used instead of Dimethylphenethylamine.

1H NMR (600 MHz, DMSO) δ 8.08 (m, 1H), 7.49 (m, 1H), 7.36 (m, 3H), 4.45 (d, J=6.0 Hz, 2H) LCMS: 184.1 (M+H+)

Example 161

1-(2-methylphenethyl)guanide hydrochloride

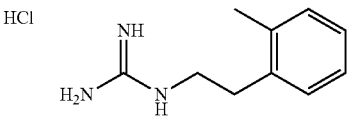

The title compound in white (340 mg, 4%) was obtained according to the same method of Example 133, except that 2-methylphenethyl amine was used instead of Dimethylphenethylamine.

1H NMR (400 MHz, DMSO) δ 7.73 (m, 1H), 7.17 (m, 5H), 7.31 (m, 2H), 2.72 (dd, J=7.8 Hz, 2H), 2.26 (s, 3H) LCMS: 178.2 (M+H+)

Example 162

1-(2-(pyridin-2-yl)ethyl)guanide hydrochloride

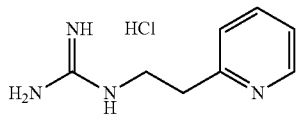 [SMILES: N=C(N)NCCc1ccccn1 ; Cl]

The title compound in white (316 mg, 96%) was obtained according to the same method of Example 133, except that 2-(pyridin-2-yl)ethyl amine was used instead of Dimethylphenethylamine.

1H NMR (600 MHz, DMSO) δ 8.52 (m, 1H), 7.75 (m, 1H), 7.68 (m, 1H), 7.34 (d, J=7.8 Hz, 1H), 7.26 (d, J=7.8 Hz, 1H), 3.54 (q, J=7.2 Hz, 2H), 2.97 (t, J=7.2 Hz, 2H) LCMS: 165 (M+H+)

Example 163

1-(2-(pyridin-3-yl)ethyl)guanide hydrochloride

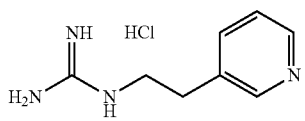 [SMILES: N=C(N)NCCc1cccnc1 ; Cl]

The title compound in white (246 mg, 75%) was obtained according to the same method of Example 133, except that 2-(pyridin-3-yl)ethyl amine was used instead of Dimethylphenethylamine.

1H NMR (600 MHz, DMSO) δ 8.63 (s, 1H), 8.49 (m, 1H), 7.77 (m, 1H), 7.75 (m, 1H), 7.12 (m, 1H), 3.40 (q, J=7.2 Hz, 2H), 2.81 (t, J=7.2 Hz, 2H) LCMS: 165 (M+H+)

Example 164

3-phenethylpropanimidamide hydrochloride

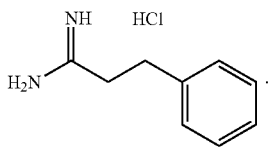

500 mg (3.8 mmol) of 3-phenylpropanenitrile as a starting material was dissolved in 10 ml of methanol and cooled to −10° C. The reaction solution was bubbled and saturated by HCl gas for 20 minutes, and then agitated at room temperature for 1 hour. The reaction solution was concentrated under vacuum, poured to seal tube and reacted with the addition of 5 ml of ammonium solution (2M ethanol) at 80° C. for 18 hours. The concentrated product was dissolved in a small amount of methanol, agitated with the addition of 12N HCl (0.28 ml, 3.41 mmol) at room temperature for 1 hour, and agitated with the addition of ethylacetate 10 ml for 30 minutes. The produced solid was filtered, washed with ethylacetate and dried under vacuum to produce the title compound in white solid (81 mg, 11%).

1H NMR (600 MHz, DMSO-D6) δ 8.14 (t, J=7.8 Hz, 2H), 8.07 (d, J=7.8 Hz, 2H), 7.98 (t, J=7.8 Hz, 1H), 3.77 (t, J=7.8 Hz, 2H), 3.52 (t, J=7.8 Hz, 2H)
LCMS: 149.2 [M+H]+

Example 165

1-(3-phenylpropyl)guanide hydrochloride

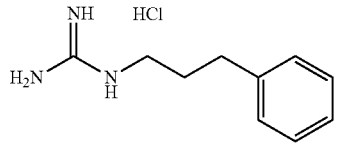 [SMILES: N=C(N)NCCCc1ccccc1 ; Cl]

The title compound in white (59 mg, 47%) was obtained according to the same method of Example 133, except that 3-phenylpropyl amine was used instead of Dimethylphenethylamine.

1H NMR (600 MHz, CD3OD) δ 7.29 (t, J=7.8 Hz, 2H), 7.22 (d, J=7.8 Hz, 2H), 7.19 (t, J=7.8 Hz, 1H), 3.19 (t, J=6.6 Hz, 2H), 2.70 (t, J=6.6 Hz, 2H), 1.92 (m, 2H) LCMS: 178 (M+H+)

Example 166

1-(2-methylbenzyl)guanide hydrochloride

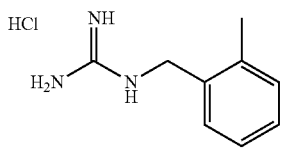

The title compound in white (420 mg, 62.8%) was obtained according to the same method of Example 133, except that 2-methylbenzyl amine was used instead of Dimethylphenethylamine.

1H NMR (600 MHz, DMSO) δ 8.05 (s, 1H), 7.21 (m, 4H), 4.34 (m, 2H), 2.27 (s, 3H) LCMS: 164.2 (M+H+)

Example 167

1-(4-(aminomethyl)benzyl)guanide sulphate

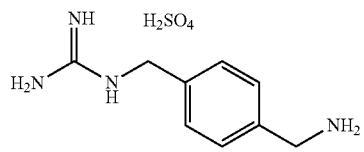

The title compound in white (96 mg, 32%) was obtained according to the same method of Example 133, except that 4-(aminomethyl)benzyl amine was used instead of Dimethylphenethylamine.

1H NMR (600 MHz, D2O) δ 7.50 (m, 4H), 4.49 (d, J=16.2 Hz, 2H), 4.24 (d, J=15 Hz, 2H) LCMS: 179 (M+H+)

Example 168

1-(4-fluoro-2-methylbenzyl)guanide hydrochloride

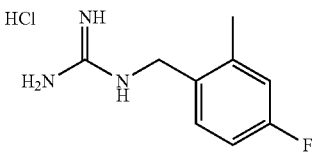

The title compound in white (460 mg, 74%) was obtained according to the same method of Example 133, except that (4-fluoro-2-methylbenzyl)amine was used instead of Dimethylphenethylamine.

1H NMR (600 MHz, D2O) δ 8.02 (m, 1H), 7.25 (m, 1H), 7.07 (m, 1H), 7.02 (d, J=8.4 Hz, 1H), 4.31 (m, 2H), 2.28 (s, 3H) LCMS: 182.1 (M+H+)

Example 169

1-(4-fluoro-2-methylphenethyl)guanide hydrochloride

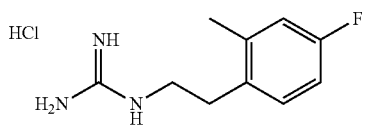

The title compound in white (320 mg, 42.4%) was obtained according to the same method of Example 133, except that (4-fluoro-2-methylphenethyl)amine was used instead of Dimethylphenethylamine.

1H NMR (600 MHz, D2O) δ 7.96 (m, 1H), 7.445 (m, 1H), 7.237 (m, 1H), 7.15 (m, 1H), 3.51 (s, 3H), 2.94 (m, 2H), 7.028 (m, 2H) LCMS: 196.1 (M+H+)

Example 170

1-(3-fluoro-4-methylbenzyl)guanide hydrochloride

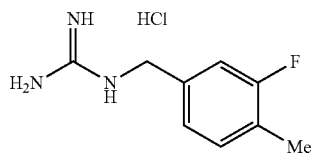 [SMILES: Cl ; Cc1ccc(CNC(=N)N)cc1F]

The title compound in white (62 mg, 40%) was obtained according to the same method of Example 133, except that (3-fluoro-4-methylbenzyl)amine was used instead of Dimethylphenethylamine.

1H NMR (600 MHz, CD3OD) δ 7.26 (t, J=8.4 Hz, 1H), 7.04 (m, 2H), 4.37 (s, 2H), 2.25 (s, 3H) LCMS: 182 (M+H+)

Example 171

1-(2,4-dimethylbenzyl)guanide hydrochloride

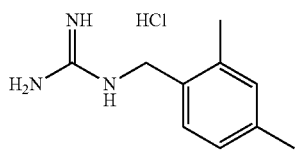

The title compound in white (380 mg, 62.3%) was obtained according to the same method of Example 133, except that (2,4-dimethylbenzyl)amine was used instead of Dimethylphenethylamine.

1H NMR (400 MHz, CD3OD) δ 7.14 (d, J=7.6 Hz, 1H), 7.06 (s, 1H), 7.03 (d, J=7.6 Hz, 1H), 4.33 (s, 2H), 2.30 (s, 3H), 2.29 (s, 3H) LCMS: 178 (M+H+)

Example 172

1-(3,4-difluorophenethyl)guanide hydrochloride

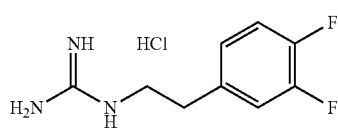 [SMILES: N=C(N)NCCc1ccc(F)c(F)c1 ; Cl]

The title compound in white (171 mg, 54%) was obtained according to the same method of Example 133, except that (3,4-difluorophenethyl)amine was used instead of Dimethylphenethylamine.

1H NMR (600 MHz, DMSO) δ 7.76 (m, 1H), 7.39 (m, 2H), 7.13 (m, 1H), 3.37 (q, J=7.2 Hz, 2H), 2.78 (t, J=7.2 Hz, 2H) LCMS: 200 (M+H+)

Example 173

1-(2-morpholinoethyl)guanide hydrochloride

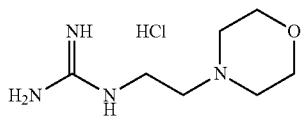 [SMILES: N=C(N)NCCN1CCOCC1 ; Cl]

The title compound in white solid (487 mg, 98%) was obtained according to the same method of Example 133, except that (2-morpholinoethyl)amine was used instead of Dimethylphenethylamine.

1H NMR (600 MHz, DMSO) δ 3.58 (s, 4H), 3.23 (s, 2H), 2.42 (m, 4H)

LCMS: 173 (M+H+)

Example 174

1-(4-fluorophenethyl)-1-methyl guanide hydrochloride

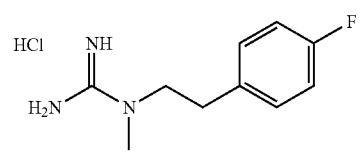

The title compound in white solid (230 mg, 43.6%) was obtained according to the same method of Example 133, except that 4-fluorophenethyl)-1-methyl amine was used instead of Dimethylphenethylamine.

1H NMR (600 MHz, DMSO) δ 7.34 (m, 2H), 7.12 (m, 2H), 3.53 (t, J=7.2 Hz, 2H), 2.88 (s, 3H), 2.49 (t, J=7.2 Hz, 2H) LCMS: 196.1 (M+H+)

Example 175

(S)-1-(2-phenylpropyl)guanide hydrochloride

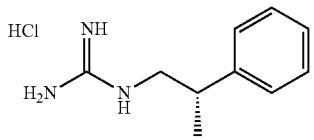

The title compound in white solid (250 mg, 47.3%) was obtained according to the same method of Example 133, except that (R)-2-phenylpropan-1-amine was used instead of Dimethylphenethylamine.

1H NMR (600 MHz, DMSO) δ 7.75 (m, 2H), 7.30 (m, 4H), 7.21 (m, 1H), 3.31 (t, J=6.0 Hz, 2H), 2.90 (m, 1H), 1.24 (s, 3H) LCMS: 178.2 (M+H+)

Example 176

1-(2-fluoro-4-hydroxybenzyl)guanide hydrochloride

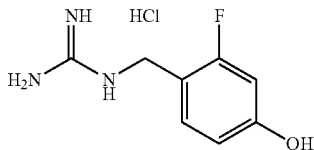 [SMILES: Cl ; N=C(N)NCc1ccc(O)cc1F]

The title compound in white solid (35.5 mg, 29%) was obtained according to the same method of Example 133, except that 2-fluoro-4-hydroxybenzyl amine was used instead of Dimethylphenethylamine.

1H NMR (600 MHz, DMSO) δ 10.02 (s, 1H), 7.85 (s, 1H), 7.20 (t, J=9 Hz, 2H), 6.63 (m, 2H), 4.18 (s, 2H) LCMS: 184.1 (M+H+)

Example 177

1-(2-bromobenzyl)guanide hydrochloride

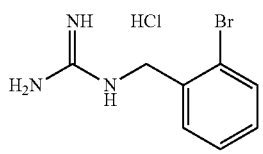 [SMILES: Cl ; N=C(N)NCc1ccccc1Br]

The title compound in white solid (177 mg, 31%) was obtained according to the same method of Example 133, except that 2-bromobenzyl amine was used instead of Dimethylphenethylamine.

1H NMR (600 MHz, CD3OD) δ 7.66 (d, J=8.4 Hz, 1H), 7.423 (m, 2H), 7.29 (m, 1H), 4.489 (s, 2H) LCMS: 228.1, 230.0((M−H+, M+H+)

Example 178

1-(3-fluorophenethyl)guanide hydrochloride

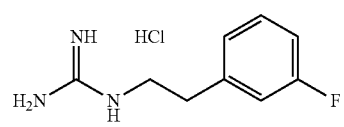 [SMILES: N=C(N)NCCc1cccc(F)c1 ; Cl]

The title compound in white solid (136 mg, 29%) was obtained according to the same method of Example 133, except that 3-fluorophenethyl amine was used instead of Dimethylphenethylamine.

1H NMR (600 MHz, CD3OD) δ 7.34 (q, J=7.2 Hz, 1H), 7.09 (d, J=7.2 Hz, 1H), 7.04 (d, J=7.2 Hz, 1H), 6.98 (t, J=7.2 Hz, 1H), 3.47 (t, J=7.2 Hz, 2H), 2.91 (t, J=7.2 Hz, 2H) LCMS: 182.1 (M+H+)

Example 179

1-(3-bromo-4-fluorobenzyl)guanide hydrochloride

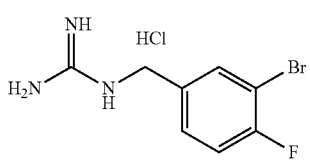

The title compound in white solid (440 mg, 37.6%) was obtained according to the same method of Example 133, except that (3-bromo-4-fluorobenzyl) amine was used instead of Dimethylphenethylamine.

1H NMR (600 MHz, CD3OD) δ 7.62 (d, J=7.2 Hz, 1H), 7.35 (m, 1H), 7.24 (t, J=8.4 Hz, 1H), 4.40 (s, 2H) LCMS: 246, 247 (M, M+H+)

Example 180

1-(2-fluoro-4-methylbenzyl)guanide hydrochloride

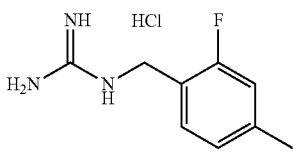

The title compound in white solid 120 mg, 17.5%) was obtained according to the same method of Example 133, except that (2-fluoro-4-methylbenzyl) amine was used instead of Dimethylphenethylamine.

1H NMR (600 MHz, CD3OD) δ 7.24 (t, J=7.2 Hz, 1H), 7.03 (d, J=7.8 Hz, 1H), 7.00 (d, J=10.8 Hz, 1H), 4.41 (s, 2H), 2.55 (s, 3H) LCMS: 182 (M+H+)

Example 181

1-(2-(piperidin-1-yl)ethyl)guanide hydrochloride

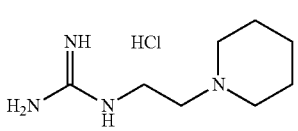

The title compound in white solid (500 mg, 98%) was obtained according to the same method of Example 133, except that 2-(piperidin-1-yl)ethyl amine was used instead of Dimethylphenethylamine.

1H NMR (600 MHz, DMSO) δ 3.68 (m, 2H), 3.43 (m, 4H), 3.14 (m, 2H), 2.83 (m, 2H), 1.79 (m, 4H), 1.70 (m, 1H), 1.38 (m, 1H) LCMS: 171.2 (M+H+)

Example 182

1-(4-cyclopropylphenethyl)guanide hydrochloride

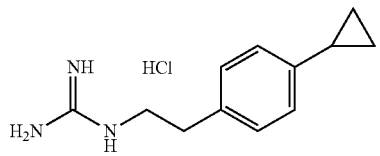 [SMILES: N=C(N)NCCc1ccc(C2CC2)cc1 ; Cl]

The title compound in white solid (110 mg, 30.6%) was obtained according to the same method of Example 133, except that 4-cyclopropylphenethyl amine was used instead of Dimethylphenethylamine.

1H NMR (400 MHz, CD3OD) δ 7.10 (d, J=8.0 Hz, 2H), 7.00 (d, J=6.4 Hz, 2H), 3.38 (t, J=7.2 Hz, 2H), 2.78 (t, J=6.8 Hz, 2H), 1.84 (m, 1H), 0.90 (m, 2H), 0.58 (m, 2H) LCMS: 204 (M+H+)

Example 183

1-(2-(5,6,7,8-tetrahydronaphthalen-2-yl)ethyl)guanide hydrochloride

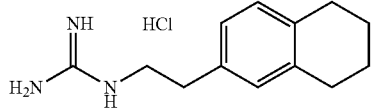 [SMILES: N=C(N)NCCc1ccc2c(c1)CCCC2 ; Cl]

The title compound in white solid (60 mg, 79%) was obtained according to the same method of Example 133, except that 2-(5,6,7,8-tetrahydronaphthalen-2-yl)ethyl amine was used instead of Dimethylphenethylamine.

1H NMR (400 MHz, DMSO) δ 7.57 (m, 1H), 6.99 (m, 3H), 3.30 (m, 2H), 2.68 (m, 6H), 1.71 (m, 4H) LCMS: 218.1 (M+H+)

Example 184

1-(4-bromobenzyl)guanide hydrochloride

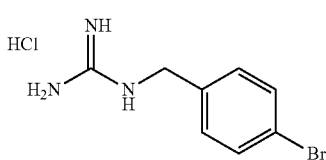 [SMILES: Cl ; N=C(N)NCc1ccc(Br)cc1]

The title compound in white solid (320 mg, 45%) was obtained according to the same method of Example 133, except that 4-bromobenzyl amine was used instead of Dimethylphenethylamine.

1H NMR (600 MHz, CD3OD) δ 7.54 (m, 2H), 7.26 (m, 2H), 4.38 (m, 2H), 3.31 (s, 3H) LCMS: 228 (M+H+)

Example 185

1-(3-(4-methoxyphenyl)propyl)guanide hydrochloride

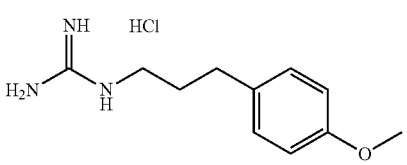

The title compound in white solid (485 mg, 58.4%) was obtained according to the same method of Example 133, except that 3-(4-methoxyphenyl)propyl amine was used instead of Dimethylphenethylamine.

1H NMR (600 MHz, CD3OD) 7.30 (t, J=7.8 Hz, 2H), 7.23 (d, J=7.8 Hz, 2H), 7.21 (t, J=7.8 Hz, 1H), 3.72 (S, 3H), 3.19 (t, J=6.6 Hz, 2H), 2.70 (t, J=6.6 Hz, 2H), 1.92 (m, 2H) LCMS: 208.1 (M+H+)

Example 186

1-(4-fluoro-2-methylbenzyl)-1-methylguanide hydrochloride

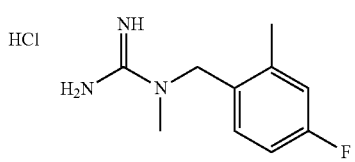

The title compound in white solid (61 mg, 20.3%) was obtained according to the same method of Example 133, except that (4-fluoro-2-methylbenzyl)-1-methyl amine was used instead of Dimethylphenethylamine.

1H NMR (600 MHz, CD3OD) δ 7.06 (m, 1H), 7.01 (m, 1H), 6.95 (m, 1H), 4.56 (s, 2H), 2.96 (s, 3H), 2.29 (s, 3H) LCMS: 196.1 [M+1]

Example 187

1-(4-phenethylphenethyl)guanide hydrochloride

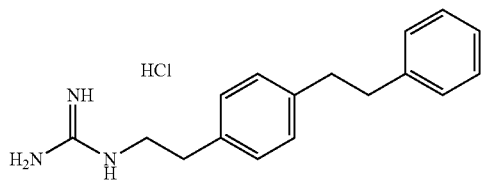 [SMILES: N=C(N)NCCc1ccc(CCc2ccccc2)cc1 ; Cl]

The title compound in white solid (110 mg, 40.7%) was obtained according to the same method of Example 133, except that 4-phenethylphenethyl amine was used instead of Dimethylphenethylamine.

1H NMR (400 MHz, CD3OD) δ 7.24~7.12 (m, 9H), 3.42 (t, J=7.2 Hz, 2H), 2.87 (s, 4H), 2.84 (t, J=7.2 Hz, 2H) LCMS: 268.1 [M+H]+

Example 188

1-methyl-1-(3-phenylpropyl)guanide hydrochloride

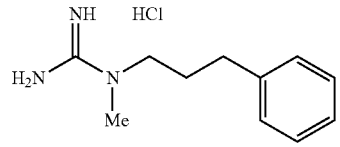 [SMILES: Cl ; CN(CCCc1ccccc1)C(=N)N]

The title compound in white solid (110 mg, 40.7%) was obtained according to the same method of Example 133, except that 1-methyl-1-(3-phenylpropyl)amine was used instead of Dimethylphenethylamine.

1H NMR (600 MHz, CD3OD) 7.30 (t, J=7.8 Hz, 2H), 7.23 (d, J=7.8 Hz, 2H), 7.21 (t, J=7.8 Hz, 1H), 3.19 (t, J=6.6 Hz, 2H), 2.70 (t, J=6.6 Hz, 2H), 2.47 (S, 3H), 1.92 (m, 2H) LCMS: 192.1 (M+H+)

Example 189

5-phenylpyrimidine-2-amine hydrochloride

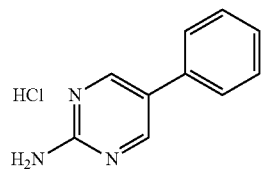 [SMILES: Cl ; Nc1ncc(-c2ccccc2)cn1]

5-bromopyrimidine-2-amine 33 mg (0.77 mmol), phenylboronic acid 112 mg (0.92 mmol), Pd catalyst and sodium carbonate 2M solution (1.54 ml) were poured to reaction vessel and heated at 100° C. at an atmosphere of nitrogen. After 18 hours, the reaction solution was added by ethylacetate and extracted by water. The organic layer was distilled under vacuum and purified with chromatograph using EA:Hex=2:1 to produce the title compound in white solid (92 mg, 70%).

1H NMR (600 MHz, CDCl3) δ 8.53 (s, 2H), 7.49 (m, 4H), 7.37 (t, J=6.6 Hz, 1H) LCMS: 172.1 [M+H]+

Example 190

1-(2-cyclopropylethyl)guanide hydrochloride

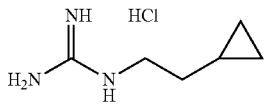

The title compound in white solid (62 mg, 19.2%) was obtained according to the same method of Example 133, except that 2-cyclopropylethyl amine was used instead of Dimethylphenethylamine.

1H NMR (600 MHz, CD3OD) δδ 3.28 (t, 2H), 1.47 (q, 2H), 0.77 (m, 1H), 0.49 (m, 1H), 0.10 (m, 2H) LCMS: 128.1 [M+H]+

Example 191

1-(4-cyclopropyl-2-fluorophenethyl)guanide hydrochloride

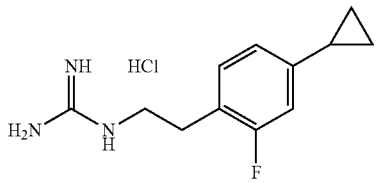 [SMILES: N=C(N)NCCc1ccc(C2CC2)cc1F ; Cl]

The title compound in white solid (46 mg, 2.4%) was obtained according to the same method of Example 133, except that (4-cyclopropyl-2-fluorophenethyl) amine was used instead of Dimethylphenethylamine.

1H NMR (600 MHz, CD3OD) δ 7.17 (t, J=8.4 hz, 1H), 6.86 (d, J=7.8 Hz, 1H), 6.77 (d, J=12 Hz, 1H), 3.43 (t, J=7.2 Hz, 2H), 2.87 (t, J=6.6 Hz, 2H), 1.89 (m, 1H), 0.96 (m, 2H), 0.64 (m, 2H) LCMS: 222.1 [M+H]+

Example 192

1-(1-(5,6,7,8-tetrahydronaphthalene-1-yl)ethyl)guanide hydrochloride

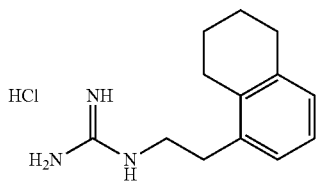 [SMILES: Cl ; N=C(N)NCCc1cccc2c1CCCC2]

The title compound in white solid (400 mg, 44%) was obtained according to the same method of Example 133, except that (2-(5,6,7,8-tetrahydronaphthalen-1-yl)ethyl) amine was used instead of Dimethylphenethylamine.

1H NMR (600 MHz, DMSO) δ 7.75 (m, 1H), 7.00 (m, 2H), 6.92 (m, 1H), 3.29 (m, 2H), 2.70 (m, 4H), 2.65 (m, 2H), 1.74 (m, 2H), 1.67 (m, 2H)

LCMS: 218.1 [M+1]

Example 193

1-methyl-1-((5,6,7,8-tetrahydronaphthalene-1-yl)methyl)guanide hydrochloride

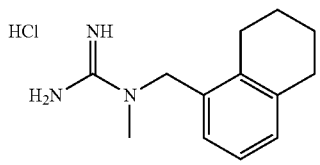 [SMILES: Cl ; CN(Cc1cccc2c1CCCC2)C(=N)N]

The title compound in white solid (75 mg, 10.1%) was obtained according to the same method of Example 133, except that 1-methyl-1-((5,6,7,8-tetrahydronaphthalen-1-yl) methyl amine was used instead of Dimethylphenethylamine.

1H NMR (600 MHz, DMSO) δ 7.52 (m, 4H), 7.11 (m, 1H), 7.02 (m, 1H), 6.71 (m, 1H), 4.49 (s, 2H), 3.35 (s, 2H), 2.94 (s, 3H), 2.74 (s, 2H), 2.54 (s, 2H), 1.77 (m, 2H), 1.70 (m, 2H) LCMS: 218.1 [M+1]

Example 194

1-(2-cyclobutylethyl)guanide hydrochloride

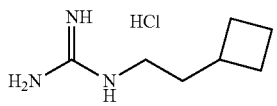

The title compound in white solid (14 mg, 3.9%) was obtained according to the same method of Example 133, except that 2-cyclobutylethyl amine was used instead of Dimethylphenethylamine.

1H NMR (400 MHz, CD3OD) δ3.09 (m, 2H), 2.10 (m, 2H), 1.19 (m, 1H), 1.68 (m, 2H), 1.32 (m, 4H) LCMS: 142.1 [M+H]+

Example 195

1-(4-phenylphenethyl)guanide hydrochloride

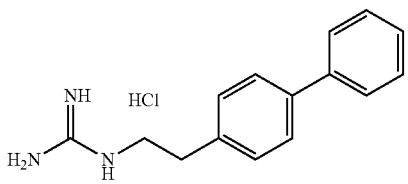 [SMILES: N=C(N)NCCc1ccc(-c2ccccc2)cc1 ; Cl]

The title compound in white solid (40 mg, 12%) was obtained according to the same method of Example 133, except that 4-phenylphenethyl amine was used instead of Dimethylphenethylamine.

1H NMR (600 MHz, CD3OD) δ 7.59 (m, 4H) 7.42 (m, 2H), 7.34 (m, 3H), 3.49 (t, J=6.6 Hz, 2H), 2.93 (t, 7.8 Hz, 2H) LCMS: 240.1 [M+H]+

Example 196

1-(naphthalen-1-ylmethyl)guanide hydrochloride

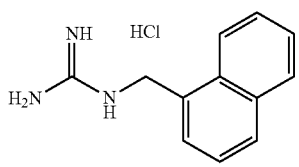 [SMILES: N=C(N)NCc1cccc2ccccc12 ; Cl]

The title compound in white solid (480 mg, 32%) was obtained according to the same method of Example 133, except that 1-naphthalenemethyl amine was used instead of Dimethylphenethylamine.

1H NMR (600 MHz, CD3OD) δ 8.00 (d, J=7.8 Hz, 1H), 7.94 (d, J=8.4 Hz, 1H), 7.90 (d, J=7.2 Hz, 1H), 7.62 (m, 1H), 7.55 (m, 1H), 7.50 (m, 2H), 4.87 (s, 2H)
LCMS: 200.1 [M+H]+

Example 197

1-(2-cyclohexylethyl)guanide hydrochloride

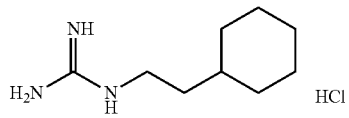 [SMILES: N=C(N)NCCC1CCCCC1 ; Cl]

The title compound in white solid (400 mg, 53.8%) was obtained according to the same method of Example 133, except that 2-cyclohexylethyl amine was used instead of Dimethylphenethylamine.

1H NMR (600 MHz, CD3OD) δ3.20 (t, J=7.2 Hz, 2H), 1.74 (m, 4H), 1.66 (d, 1H), 1.50 (q, 2H), 1.38 (m, 1H), 1.27 (m, 2H), 1.20 (m, 1H), 0.96 (m, 2H)

LCMS: 170.3 [M+H]+

Example 198

11-(naphthalen-2-ylmethyl)guanide hydrochloride

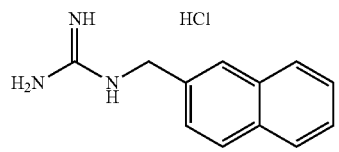 [SMILES: Cl ; N=C(N)NCc1ccc2ccccc2c1]

The title compound in white solid (200 mg, 37.7%) was obtained according to the same method of Example 133, except that 2-naphthylmethanamine was used instead of Dimethylphenethylamine.

1H NMR (600 MHz, CD3OD) δ 7.91 (d, J=8.4 Hz, 1H) 7.87 (m, 2H), 7.81 (s, 1H), 7.52 (m, 2H), 7.45 (d, J=9.0 Hz, 1H), 4.58 (s, 2H)

LCMS: 200.1 [M+H]+

Example 199

1-((5,6,7,8-tetrahydronaphthalen-2-yl)methyl guanide hydrochloride

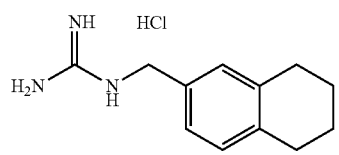 [SMILES: N=C(N)NCc1ccc2c(c1)CCCC2 ; Cl]

The title compound in white solid (110 mg, 31%) was obtained according to the same method of Example 133, except that (5,6,7,8-tetrahydronaphthalen-2-yl)methyl amine was used instead of Dimethylphenethylamine.

1H NMR (600 MHz, DMSO) 8.03 (m, 1H), 7.00 (m, 3H), 4.27 (d, J=5.3 Hz, 2H), 2.69 (m, 4H), 1.71 (m, 4H) LCMS: 204.1 (M+H+)

Example 200

N-(4-phenyl)benzyl guanide hydrochloride

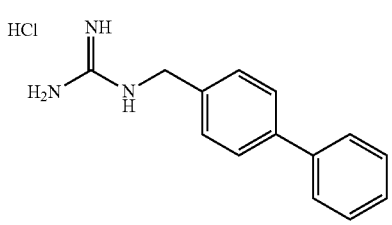 [SMILES: Cl ; N=C(N)NCc1ccc(-c2ccccc2)cc1]

The title compound in white solid (170 mg, 28.8%) was obtained according to the same method of Example 133, except that (4-phenyl)benzyl amine was used instead of Dimethylphenethylamine.
1H NMR (600 MHz, CD3OD) δ 7.91 (d, J=8.4 Hz, 1H) 7.87 (m, 2H), 7.81 (s, 1H), 7.52 (m, 2H), 7.45 (d, J=9.0 Hz, 1H), 4.58 (s, 2H) LCMS: 226.2 [M+H]+

Example 201

1-(2-(1,2,3,4-tetrahydronaphthalen-2-yl)ethyl) guanide hydrochloride

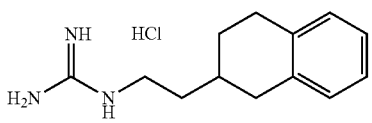 [SMILES: N=C(N)NCCC1CCc2ccccc2C1 ; Cl]

The title compound in white solid (39 mg, 23%) was obtained according to the same method of Example 133, except that 1-(2-(1,2,3,4-tetrahydronaphthalen-2-yl)ethyl amine was used instead of Dimethylphenethylamine.
1H NMR (600 MHz, DMSO-D6) 7.82 (m, 1H), 7.05 (m, 4H), 3.22 (m, 2H), 2.78 (m, 3H), 2.39 (m, 1H), 1.90 (m, 1H), 1.76 (m, 1H), 1.56 (m, 2H), 1.35 (m, 1H)
LCMS: 218.2 [M+H]+

Example 202

1-(1-adamantylmethyl) guanide hydrochloride

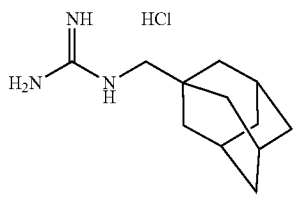 [SMILES: Cl ; N=C(N)NCC12CC3CC(CC(C3)C1)C2]

The title compound in white solid (280 mg, 47.5%) was obtained according to the same method of Example 133, except that (1-adamantylmethyl) amine was used instead of Dimethylphenethylamine.

1H NMR (600 MHz, CD3OD) δ 7.68 (m, 1H), 7.36 (s, 2H), 6.97 (s, 2H), 2.81 (s, J=6.0 Hz), 1.95 (s, 3H), 1.66 (m, 6H), 1.48 (m, 5H) LCMS: 208.2 [M+H]+

Example 203

1-(4-phenoxybenzyl) guanide hydrochloride

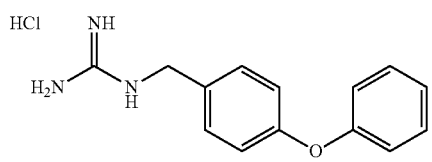 [SMILES: Cl ; N=C(N)NCc1ccc(Oc2ccccc2)cc1]

The title compound in white solid (40 mg, 7.1%) was obtained according to the same method of Example 133, except that (4-phenoxybenzyl) amine was used instead of Dimethylphenethylamine.
1H NMR (600 MHz, DMSO-D6) δ 8.21 (m, 1H), 7.39 (m, 2H), 7.34 (m, 2H), 7.14 (m, 1H), 7.01 (m, 3H), 4.36 (d, J=6.0 Hz, 2H) LCMS: 242.2 [M+H]+

Example 204

1-(2-cyclopentylethyl) guanide hydrochloride

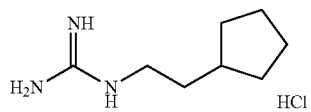 [SMILES: N=C(N)NCCC1CCCC1 ; Cl]

The title compound in white solid (90 mg, 10.6%) was obtained according to the same method of Example 133, except that (2-cyclopentylethyl) amine was used instead of Dimethylphenethylamine.
1H NMR (600 MHz, DMSO-D6) δ 7.82 (s, 1H), 7.40 (s, 2H), 6.98 (s, 2H), 2.95 (t, J=6.0 Hz, 2H), 1.68 (m, 2H), 1.61 (m, 1H), 1.47 (m, 2H), 1.18 (m, 4H), 0.91 (m, 2H) LCMS: 128.1 [M+H]+

Example 205

1-(1-cyclohexylmethyl) guanide hydrochloride

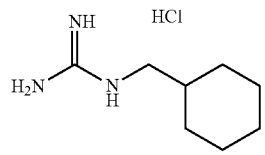 [SMILES: Cl ; N=C(N)NCC1CCCCC1]

The title compound in white solid (150 mg, 17.6%) was obtained according to the same method of Example 133, except that (1-cyclohexylmethyl) amine was used instead of Dimethylphenethylamine.
1H NMR (600 MHz, CD3OD) δ 7.78 (t, J=5.4 Hz, 7.38 (s, 2H), 7.01 (s, 2H), 3.10 (q, 2H), 1.77 (m, 1H), 1.71 (m, 2H), 1.58 (m, 2H), 1.49 (m, 4H), 1.08 (m, 2H) LCMS: 156.2 [M+H]+

Example 206

1-(4-chloro-3-methylphenthyl)guanide hydrochloride

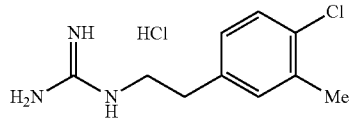

The title compound in white solid (61 mg, 28%) was obtained according to the same method of Example 133, except that (4-chloro-3-methylphenethyl) amine was used instead of Dimethylphenethylamine.

1H NMR (600 MHz, DMSO-D6) 7.66 (m, 1H), 7.36 (s, 1H), 7.29 (d, J=7.8 Hz, 1H), 7.14 (d, J=7.8 Hz, 1H), 3.39 (m, 2H), 2.76 (t, J=7.2 Hz, 2H), 2.29 (s, 3H)

LCMS: 212.1 (M+H+)

Example 207

1-(4-bromo-3-methylbenzyl) guanide hydrochloride

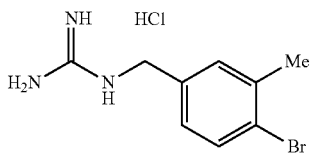

The title compound in white solid (73 mg, 30%) was obtained according to the same method of Example 133, except that (4-bromo-3-methylbenzyl) amine was used instead of Dimethylphenethylamine.

1H NMR (600 MHz, DMSO-D6) 8.17 (m, 1H), 7.59 (d, J=7.8 Hz, 1H), 7.29 (s, 1H), 7.08 (d, J=7.8 Hz, 1H), 4.33 (s, 2H), 2.34 (s, 3H)

LCMS: 242.0 244.0 (M, M+2H+)

Example 208

1-(4-bromo-3-chlorophenethyl) guanide hydrochloride

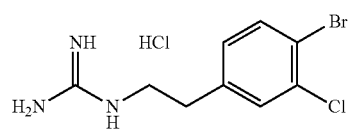

The title compound in white solid (25 mg, 5%) was obtained according to the same method of Example 133, except that (4-bromo-3-chlorophenethyl) amine was used instead of Dimethylphenethylamine.

1H NMR (600 MHz, DMSO-D6) 7.71 (m, 2H), 7.59 (s, 1H), 7.21 (d, J=8.4 Hz, 1H), 3.37 (q, 2H), 2.77 (t, J=7.2 Hz, 2H); LCMS: 276.0 278.0 [M, M+2]

Example 209

3-(benzyl formimidate)-1,1-dimethyl guanide hydrochloride

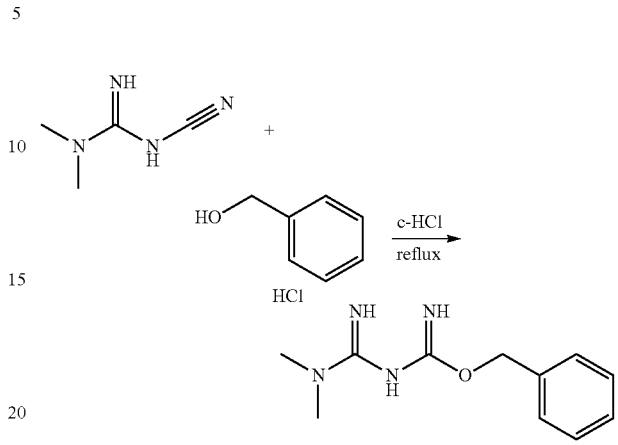

Mixed solution of N1-dimethyl cyanoguanide (200 mg, 1.78 mmol) and benzylalcohol (6 mL) were added by concentrate HCl (0.126 ml) and agitated with reflux for 18 hours. The reaction product was concentrated with vacuum and purified with chromatograph using MC:MeOH=9:1 to produce the title compound in white solid (182 mg, 40%).

1H NMR (600 MHz, CD3OD) δ 7.38 (d, J=7.8 Hz, 2H), 7.3 (m, 2H), 7.28 (m, 1H), 5.08 (s, 2H) LCMS: 222.1 [M+H]+

Example 210

3-(phenethyl formimidate)-1,1-dimethyl guanide drochloride

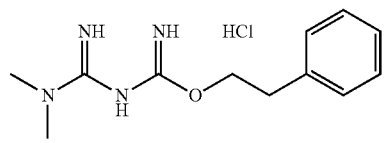 [SMILES: CN(C)C(=N)NC(=N)OCCc1ccccc1 ; Cl]

The title compound in white solid (23 mg, yield: 4.6%) was obtained according to the same method of Example 209, except that phenethyl alcohol was used instead of benzyl alcohol.

1H NMR (600 MHz, MeOH) δ 7.24 (m, 5H), 4.23 (t, J=7.2 Hz, 2H), 3.03 (s, 6H), 2.95 (t, J=7.2 Hz, 2H); LC-MS m/z 235.1 [M+1]

Example 211

3-(propyl formimidate)-1,1-dimethyl guanide hydrochloride

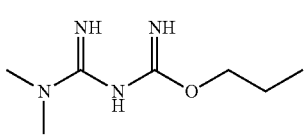

The title compound in white solid (12 mg, yield: 6.2%) was obtained according to the same method of Example 209, except that butyl alcohol was used instead of benzyl alcohol.

1H NMR (600 MHz, CD3OD) 4.13 (t, J=6.6 Hz, 2H), 3.10 (d, j=15 Hz, 6H), 1.72 (m, 2H), 0.98 (t, J=6.6 Hz, 3H); LC-MS m/z 173.2 [M+1]

Example 212

Butyl imino(pyrolidin-1-yl)methylcarbamidate hydrochloride

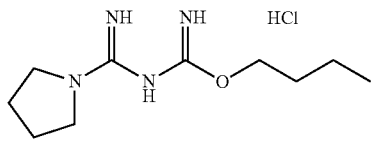

The title compound in white solid (145 mg, 40%) was obtained according to the same method of Example 209, except that N I-pyrolidine cyanoguanide was used instead of N1-dimethyl cyanoguanide and butanol was used instead of benzyl alcohol.

1H NMR (400 MHz, DMSO-d6) δ 7.83 (bs, 2H), 7.24 (bs, 2H), 4.06 (t, J=6.4 Hz, 2H), 3.34 (m, 4H), 1.95 (m, 4H), 1.60 (m, 2H), 1.379 (m, 2H), 0.91 (t, J=6.4 Hz, 3H); LC-MS m/z 213.2 [M+1]

Example 213 phenethyl imino(pyrolidin-1-yl)methylcarbamidate hydrochloride

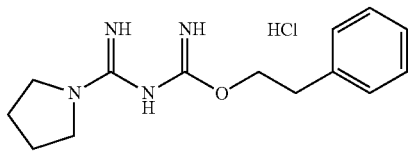 [SMILES: N=C(NC(=N)N1CCCC1)OCCc1ccccc1 ; Cl]

The title compound in white solid (145 mg, 40%) was obtained according to the same method of Example 209, except that N1-pyrolidine cyanoguanide was used instead of N1-dimethyl cyanoguanide and phenethyl alcohol was used instead of benzyl alcohol.

1H NMR (600 MHz, DMSO) δ 7.32 (m, 5H), 4.31 (t, J=6.6 Hz, 2H), 3.27 (m, 4H), 2.96 (t, J=6.6 Hz, 2H), 1.95 (m, 4H); LC-MS m/z 261.2 [M+1]

Example 214

Benzylimino(pyrolidin-1-yl)methylcarbamidothioate hydrochloride

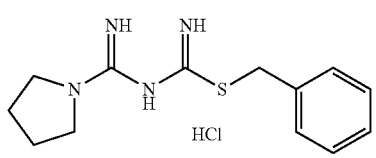 [SMILES: N=C(NC(=N)N1CCCC1)SCc1ccccc1 ; Cl]

The title compound in white solid (290 mg, 13.4%) was obtained according to the same method of Example 209, except that N1-pyrolidine cyanoguanide was used instead of N1-dimethyl cyanoguanide and benzylthiol was used instead of benzyl alcohol.

1H NMR (600 MHz, MeOH) δ 7.38 (d, J=7.2 Hz, 2H), 7.32 (t, J=7.2 Hz, 2H), 7.26 (t, J=7.2 Hz, 1H), 4.24 (s, 2H), 3.43 (t, J=7.2 Hz, 2H), 3.21 (t, J=7.2 Hz, 2H), 2.06 (t, J=6.6 Hz, 2H), 1.90 (t, J=6.6 Hz, 2H); LC-MS m/z 273.5 [M+1]

Example 215

4-fluorophenethyl imino(pyrolidin-1-yl)methylcarbamidate hydrochloride

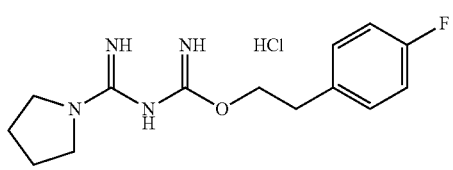 [SMILES: N=C(NC(=N)N1CCCC1)OCCc1ccc(F)cc1 ; Cl]

The title compound in white solid (27 mg, 4%) was obtained according to the same method of Example 209, except that N1-pyrolidine cyanoguanide was used instead of N1-dimethyl cyanoguanide and 4-fluorophenethyl alcohol was used instead of benzyl alcohol.

1H NMR (600 MHz, MeOH) δ 7.33 (m, 2H), 7.03 (m, 2H), 4.38 (t, J=7.2 Hz, 2H), 3.42 (m, 4H), 2.99 (t, J=7.2 Hz, 2H), 2.08 (m, 2H), 1.94 (m, 2H); LC-MS m/z 279.1 [M+1]

Example 216

1-(4-fluorophenethyl formimidate)guanide hydrochloride

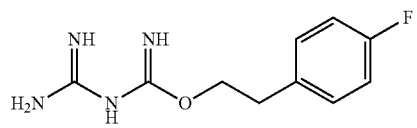 [SMILES: N=C(N)NC(=N)OCCc1ccc(F)cc1]

The title compound in white solid (300 mg, 22.5%) was obtained according to the same method of Example 209, except that dicyanamide was used instead of N1-dimethyl cyanoguanide and 4-fluorophenethyl alcohol was used instead of benzyl alcohol.

1H NMR (600 MHz, CD3OD) 7.31 (m, 2H), 7.03 (m, 2H), 4.36 (t, J=6.0 Hz, 2H), 3.05 (t, J=6.0 Hz, 2H); LC-MS m/z 225.1 [M+1]

Example 217

1-(phenethyl formimidate)guanide hydrochloride

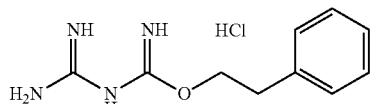

The title compound in white solid (17 mg, 24%) was obtained according to the same method of Example 209, except that dicyanamide was used instead of N1-dimethyl cyanoguanide and phenethyl alcohol was used instead of benzyl alcohol.

1H NMR (600 MHz, CD3OD) δ 7.38 (d, J=7.8 Hz, 2H), 7.23 (d, J=7.8 Hz, 2H), 2.98 (bs, 6H); LC-MS m/z 208.1 [M+1]

Example 218

1-(butyl formimidate)guanide hydrochloride

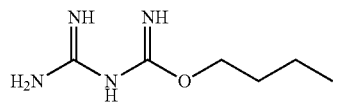

The title compound in white solid (6 mg, 2%) was obtained according to the same method of Example 209, except that dicyanamide was used instead of N1-dimethyl cyanoguanide and butyl alcohol was used instead of benzyl alcohol.

1H NMR (600 MHz, CD3OD) δ 7.23 (m, 2H), 7.00 (m, 2H) [ [0] ], 3.32 (m, 2H), 2.77 (m, 2H) LCMS: 225.1 [M+H]+

Example 219

1-(benzyl formimidate)guanide hydrochloride

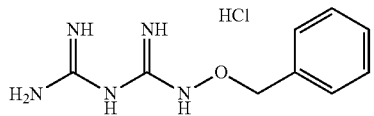

The title compound in white solid (130 mg, 14.2%) was obtained according to the same method of Example 209, except that dicyanamide was used instead of N1-dimethyl cyanoguanide and O-benzylhydroxylamine was used instead of benzyl alcohol.

1H NMR (600 MHz, CD3OD) δ 7.42 (m, 2H) 7.35 (m, 3H), 4.97 (m, 2H)
LCMS: 208.1 [M+H]+

Example 220

1-(butyl formimidate)-3-(2-(benzo[d][1,3]dioxol-5-yl)ethyl) guanide hydrochloride

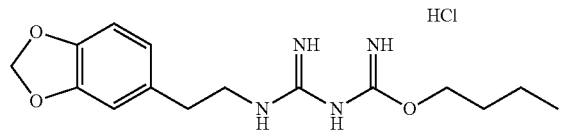 [SMILES: Cl ; CCCCOC(=N)NC(=N)NCCc1ccc2c(c1)OCO2]

The title compound in white solid (8 mg, 2%) was obtained according to the same method of Example 209, except that N1-homopiperonyl cyanoguanide was used instead of N1-dimethyl cyanoguanide and butyl alcohol was used instead of benzyl alcohol.

1H NMR (600 MHz, CD3OD) δ 6.73 (m, 3H), 4.16 (m, 2H), 3.42 (m, 2H), 2.76 (m, 2H), 1.67 (m, 2H), 1.45 (m, 2H), 0.96 (s, 3H) LCMS: 307.4 [M+H]+

Example 221

1-(phenethyl formimidate)-3-(2-(benzo[d][1,3]dioxol-5-yl)ethyl) guanide

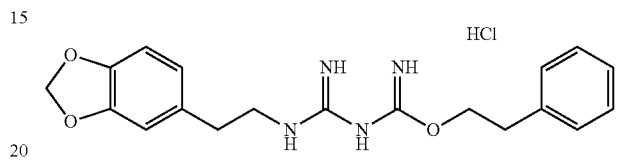

The title compound in white solid (16 mg, 3.3%) was obtained according to the same method of Example 209, except that N1-homopiperonyl cyanoguanide was used instead of N1-dimethyl cyanoguanide and phenethyl alcohol was used instead of benzyl alcohol.

1H NMR (600 MHz, CD3OD) δ 7.44 (m, 2H), 7.38 (m, 3H), 1.38 (m, 2H)

LCMS: 166.2 [M+H]+

Example 222

N-1-(N-dimethylaminosulphonyl)-N-3-phenethyl guanide hydrochloride

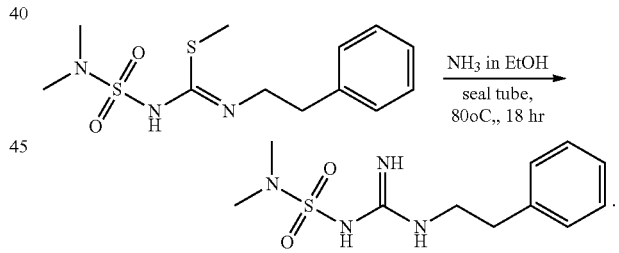

4 g of (Z)-methyl N—N,N-dimethylsulphamoyl-N'-phenethylcarbamidothioate (4.7 mmol) was poured to seal tube, added by ammonium solution, and reacted at 80° C. for 18 hours. The reaction product was cooled to room temperature, concentrated under vacuum and purified with chromatograph using MC:MeOH=9:1. The product was dissolved in a small amount of methanol, agitated with addition of 12N hydrochloride (0.28 ml, 3.41 mmol) at a room temperature for 1 hour. Then, the reaction product was agitated with addition of 10 ml of ethylacetate for 30 minutes. The produced solid was filtered, washed with ethylacetate and dried under vacuum to obtain the title compound in white solid (790 mg, 54.7%).

1H NMR (400 MHz, DMSO-D6) δ 7.31 (m, 2H), 7.22 (m, 3H), 3.32 (m, 2H), 2.77 (m, 2H), 2.50 (s, 3H), 2.49 (s, 3H) LCMS: 293.1 [M+Na]

Example 223

N-1-(aminosulphonyl)-N-3-phenethyl guanide hydrochloride

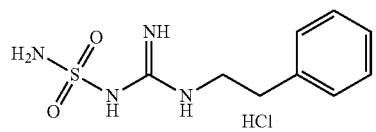 [SMILES: N=C(NCCc1ccccc1)NS(N)(=O)=O ; Cl]

The title compound in white solid (270 mg. 36%) was obtained according to the same method of Example 222, except that (Z)-methyl N-sulphamoyl-N'-phenethylcarbamidothioate was used instead of (Z)-methyl N—N,N-dimethylsulphamoyl-N'-phenethylcarbamidothioate.

1H NMR (600 MHz, DMSO-D6) δ 7.31 (m, 2H), 7.24 (m, 2H), 7.21 (m, 1H), 6.46 (bs, 2H), 6.07 (bs, 2H), 3.30 (q, J=7.2 Hz, 2H), 2.76 (t, J=7.2 Hz, 2H)

LCMS: 243.4 [M+H]

Example 224

N-(5-methyl-1H-benzo[d]imidazol-2-yl)pyrrolidine-1-carboximidamide hydrochloride

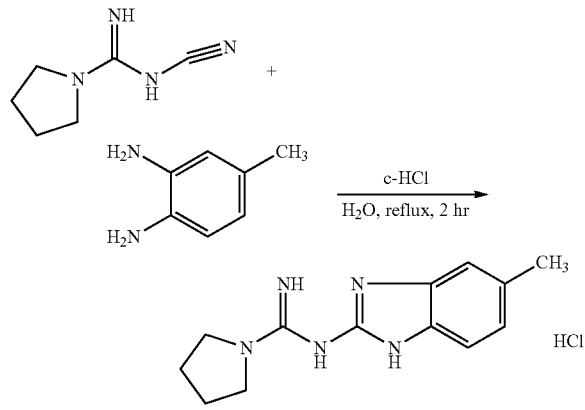

3,4-diaminotoluene (0.88 g, 7.24 mmol) was dissolved in H2O (20 ml) at room temperature, and agitated by reflux with the addition of N-pyrrolcyanoguanide (1.0 g, 7.23 mmol) and 12N HCl (1.3 ml, 14.47 mmol) for 2 hours. The reaction product was cooled to room temperature, added by 10% potassium hydroxide solution and then the produced solid was filtered. The obtained solid was dissolved in a small amount of methanol, agitated with the addition of 12N HCl (1.3 ml, 14.47 mmol) at a room temperature, and distilled under vacuum to produce the title compound in white solid (500 mg, 24.9%).

1H NMR (600 MHz, CD3OD) δ 7.13 (d, 1H), 7.06 (s, 1H), 6.82 (d, 1H), 3.47 (s, 4H), 2.37 (s, 3H), 1.98 (s, 4H) LCMS: 244.0 [M+H]+

Example 225

N-(5-fluoro-1H-benzo[d]imidazol-2-yl)pyrrolidine-1-carboximidamide hydrochloride

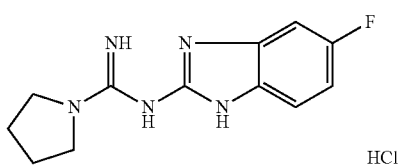 [SMILES: N=C(Nc1nc2cc(F)ccc2[nH]1)N1CCCC1 ; Cl]

The title compound in white solid (860 mg. 42%) was obtained according to the same method of Example 224, except that 1,2-Diamino-4-fluorobenzene was used instead of 3,4-diaminotoluene.

1H NMR (600 MHz, CD3OD) δ 7.15 (dd, 1H), 6.95 (dd, 1H), 6.72 (m, 1H), 3.48 (s, 4H), 1.98 (s, 4H) LCMS: 248.0 [M+H]+

Example 226

N-(5-trifluoromethoxy-1H-benzo[d]imidazol-2-yl)pyrrolidine-1-carboximidamide hydrochloride

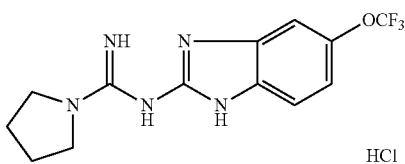 [SMILES: N=C(Nc1nc2cc(OC(F)(F)F)ccc2[nH]1)N1CCCC1 ; Cl]

The title compound in white solid (20 mg. 12%) was obtained according to the same method of Example 224, except that 1,2-Diamino-4-trifluoromehoxybenzene was used instead of 3,4-diaminotoluene.

1H NMR (600 MHz, CD3OD) δ 7.20 (d, 1H), 7.12 (s, 1H), 6.87 (s, 1H), 3.46 (s, 4H), 1.95 (S, 4H) LCMS: 314.0 [M+H]+

Example 227

N-(5-methoxy-1H-benzo[d]imidazol-2-yl)pyrrolidine-1-carboximidamide hydrochloride

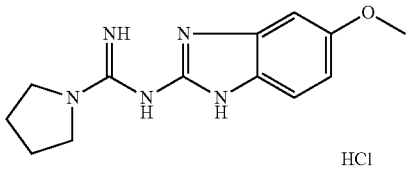 [SMILES: COc1ccc2[nH]c(NC(=N)N3CCCC3)nc2c1 ; Cl]

The title compound in white solid (460 mg. 43%) was obtained according to the same method of Example 224, except that 1,2-Diamino-4-methoxybenzene was used instead of 3,4-diaminotoluene.

1H NMR (600 MHz, CD3OD) δ 7.13 (d, 1H), 6.85 (s, 1H), 6.64 (d, 1H), 3.78 (s, 3H), 3.62 (s, 4H), 1.98 (s, 4H) LCMS: 260.0 [M+H]+

Example 228

N-(1H-benzo[d]imidazol-2-yl)pyrrolidine-1-carboximidamide hydrochloride

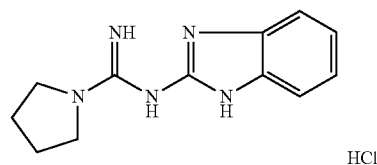 [SMILES: N=C(Nc1nc2ccccc2[nH]1)N1CCCC1 ; Cl]

The title compound in white solid (300 mg. 31.2%) was obtained according to the same method of Example 224, except that 1,2-Diaminobenzene was used instead of 3,4-diaminotoluene.

1H NMR (600 MHz, CD3OD) δ 7.25 (m, 2H), 6.99 (sm 2H), 3.50 (s, 4H), 1.98 (s, 4H) LCMS: 230.1 [M+H]+

Example 229

1-phenethyl-3-(thiazol-2-yl)urea hydrochloride

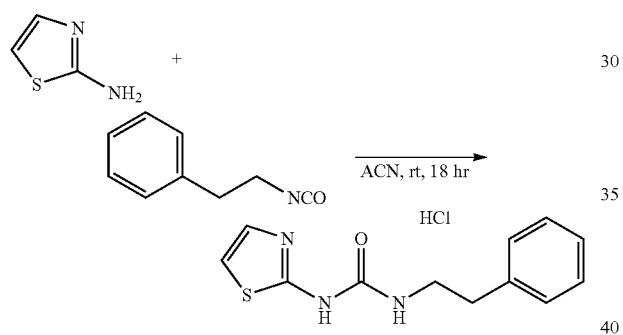

Thiazole-2-amine (0.5 g, 4.99 mmol) was dissolved in acetonitrile solution (20 ml) at a room temperature, and agitated with the slow addition of phenethylisocyanate (0.83 ml, 5.99 mmol) at 0° C. for 2 hours. After the reaction completed, the product was distilled under vacuum and purified with chromatograph using EA:Hex=1:3. The purified product was dissolved in a small amount of methylol, agitated with the addition of 12N HCl (0.43 ml, 4.99 mmol) at a room temperature, and distilled under vacuum to produce the title compound in white solid (790 mg, 56.0%).

1H NMR (600 MHz, CD3OD) δ 7.29 (m, 4H), 7.24 (m, 1H), 6.93 (m, 1H), 3.49 (m, 2H), 2.83 (m, 2H) LCMS: 248.2 [M+1]

Example 230

1-(oxazol-2-yl)-3-phenethyl urea hydrochloride

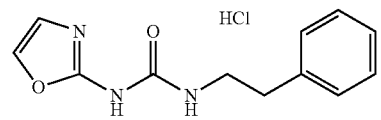 [SMILES: O=C(NCCc1ccccc1)Nc1ncco1 ; Cl]

The title compound in white solid (15 mg. 5.7%) was obtained according to the same method of Example 229, except that 2-aminooxazole was used instead of thiazole-2-amine.

1H NMR (600 MHz, CD3OD) δ 7.48 (s, 1H), 7.24 (m, 4H), 7.17 (m, 1H), 6.90 (s, 1H), 3.51 (m, 2H), 2.84 (m, 2H) LCMS: 232.2 [M+1

Example 231

1-benzyl-3-(oxazol-2-yl)urea hydrochloride

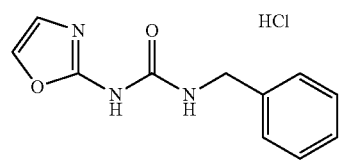 [SMILES: O=C(NCc1ccccc1)Nc1ncco1 ; Cl]

The title compound in white solid (23 mg. 10.9%) was obtained according to the same method of Example 229, except that 2-aminooxazole was used instead of thiazole-2-amine, and benzyl isocyanate was used instead of phenethyl isocyanate.

1H NMR (600 MHz, CD3OD) δ 7.47 (m, 2H), 7.29 (m, 2H), 7.04 (m, 1H), 6.76 (m, 2H) LCMS: 203.2 [M+H]+

Example 232

1-(4-fluorobenzyl)-3-(thioazol-2-yl)urea hydrochloride

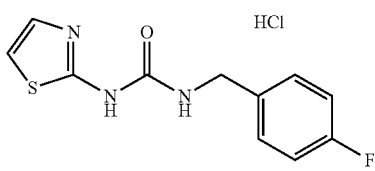 [SMILES: O=C(NCc1ccc(F)cc1)Nc1nccs1 ; Cl]

The title compound in white solid (23 mg. 6.1%) was obtained according to the same method of Example 229, except that 4-fluorobenzyl isocyanate was used instead of phenethylisocyanate.

1H NMR (600 MHz, CD3OD) δ 7.33 (m, 2H), 7.24 (m, 1H), 7.05 (m, 2H), 6.96 (m, 1H), 4.56 (s, 2H) LCMS: 252.2 [M+1]+

Example 233

1-(4-fluorobenzyl)-3-(oxazol-2-yl)urea hydrochloride

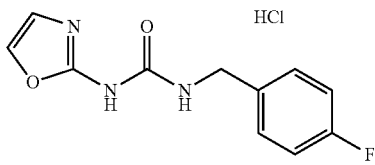 [SMILES: O=C(NCc1ccc(F)cc1)Nc1ncco1 ; Cl]

The title compound in white solid (60 mg. 16.8%) was obtained according to the same method of Example 229, except that 2-aminooxazole was used instead of thiazole-2-amine, and 4-fluorobenzyl isocyanate was used instead of phenethylisocyanate.

1H NMR (600 MHz, CD3OD) δ 7.51 (s, 1H), 7.33 (m, 2H), 7.06 (m, 2H), 6.964 (s, 1H), 4.46 (s, 2H) LCMS: 236.2 [M+1]

Example 234

1-ethyl-3-(oxazol-2-yl)urea hydrochloride

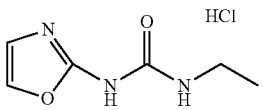

The title compound in white solid (66 mg. 20.7%) was obtained according to the same method of Example 229, except that 2-aminooxazole was used instead of thiazole-2-amine, and ethyl isocyanate was used instead of phenethylisocyanate.

1H NMR (600 MHz, CD3OD) δ 7.50 (s. 1H), 6.95 (s, 1H), 3.31 (m, 2H), 1.20 (t, 3H) LCMS: 156.1 [M+H]+

Example 235

1-ethyl-3-(thioazol-2-yl)urea hydrochloride

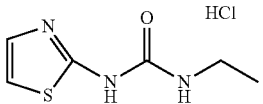

The title compound in white solid (66 mg. 20.7%) was obtained according to the same method of Example 229, except that ethyl isocyanate was used instead of phenethylisocyanate.

1H NMR (600 MHz, DMSO-D6) δ 7.39 (d, 1H), 7.10 (d, 1H), 7.07 (s, 1H), 3.16 (m, 2H), 1.07 (t, 3H) LCMS: 172.1 [M+H]+

Example 236

1-(4-fluorophenethyl)-3-(thioazol-2-yl)urea hydrochloride

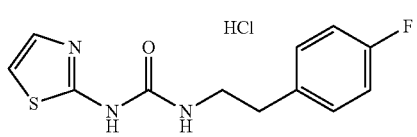 [SMILES: O=C(NCCc1ccc(F)cc1)Nc1nccs1 ; Cl]

The title compound in white solid (200 mg. 16.6%) was obtained according to the same method of Example 229, except that 4-fluorophenethyl isocyanate was used instead of phenethylisocyanate.

1H NMR (600 MHz, CD3OD) δ 7.26 (m, 3H), 6.99 (m, 3H), 3.46 (t, 2H), 2.83 (t, 2H) LCMS: 266.0 [M+H]+

Example 237

1-benzyl-3-(thioazol-2-yl)urea hydrochloride

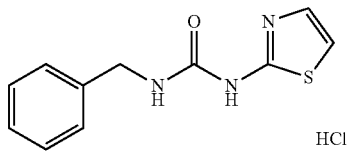 [SMILES: O=C(NCc1ccccc1)Nc1nccs1 ; Cl]

The title compound in white solid (55 mg, 30%) was obtained according to the same method of Example 229, except that benzyl isocyanate was used instead of phenethylisocyanate.

1H NMR (600 MHz, DMSO) δ 10.50 (bs, 1H), 7.36 (d, J=7.6 Hz, 2H), 7.30 (m, 3H), 7.26 (t, J=7.6 Hz, 1H), 7.06 (m, 1H), 7.01 (d, J=3.6 Hz, 1H), 4.34 (d, J=6 Hz, 2H); LC-MS m/z 234.0 [M+1]

Example 238

1-phenyl-3-(thioazol-2-yl)urea

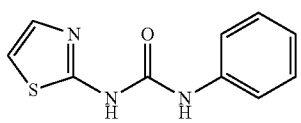 [SMILES: O=C(Nc1ccccc1)Nc1nccs1]

The title compound in white solid (272 mg, 41.4%) was obtained according to the same method of Example 229, except that phenyl isocyanate was used instead of phenethylisocyanate.

1H NMR (600 MHz, CD3OD) δ 7.57 (m, 1H), 7.51 (m, 2H), 7.32 (m, 2H), 7.09 (m, 1H), 7.05 (m, 1H); LC-MS m/z 220.1 [M+1]

Example 239

1-(oxazol-2-yl)-3-phenylurea

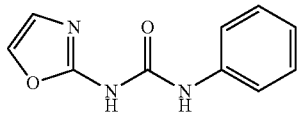 [SMILES: O=C(Nc1ccccc1)Nc1ncco1]

The title compound in white solid (44 mg, 18.2%) was obtained according to the same method of Example 229, except that phenyl isocyanate was used instead of phenethylisocyanate, and aminooxazole was used instead of aminothiazole.

1H NMR (600 MHz, CD3OD) δ 7.57 (m, 1H), 7.51 (m, 2H), 7.32 (m, 2H), 7.09 (m, 1H), 7.05 (m, 1H); LC-MS m/z 204.2 [M+1]

Example 240

1,1-dimethyl-3-(thioazol-2-yl)urea hydrochloride

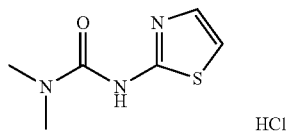

The title compound in white solid (53 mg, 32%) was obtained according to the same method of Example 229, except that NN-dimethyl isocyanate was used instead of phenethylisocyanate.

1H NMR (600 MHz, DMSO) δ 7.44 (d, J=4.2 Hz, 1H), 7.10 (d, J=4.2 Hz, 1H), 2.97 (s, 6H); LC-MS m/z 172.1 [M+1]

Example 241

1-(1H-imidazol-2-yl)-3-phenylurea

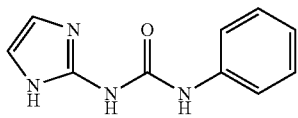 [SMILES: O=C(Nc1ccccc1)Nc1ncc[nH]1]

The title compound in white solid (18 mg, 41.6%) was obtained according to the same method of Example 229, except that phenyl isocyanate was used instead of phenethylisocyanate, and aminoimidazole was used instead of aminothiazole.

1H NMR (600 MHz, CD3OD) δ 7.47 (m, 2H), 7.29 (m, 2H), 7.04 (m, 1H), 6.76 (m, 2H); LC-MS m/z 203.2 [M+1]

Example 242

N-1-(N,N-dimethylaceteamide-N-5-(4-trifluoromethoxy)phenylbiguanide hydrochloride

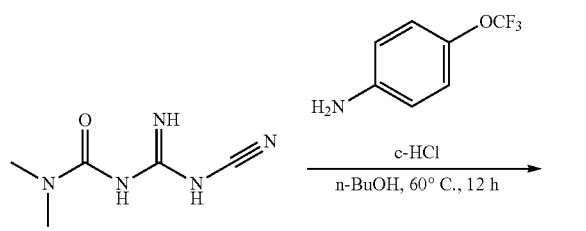

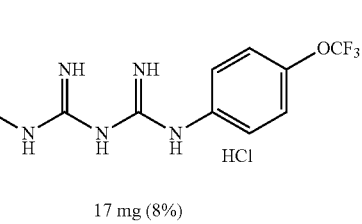

N—(N-cyanocarbamidoyl)dimethyl-1-carboxyamide (100 mg, 0.64 mmol) was added by butanol (6 ml) and 4-(trifluoromethoxy)aniline (0.085 ml, 0.64 mmol), and agitated for 18 hours at 60° C. The reaction product was purified with chromatograph using MC:MeOH=9:1 to produce the title compound in white solid (17 mg, 8%).

1H NMR (600 MHz, CD3OD) δ 7.38 (d, J=7.8 Hz, 2H), 7.23 (d, J=7.8 Hz, 2H), 2.98 (bs, 6H); LC-MS m/z 333.1 [M+1]

Example 243

N-carbamoylpyrolidine-1-carboxyimidamide hydrochloride

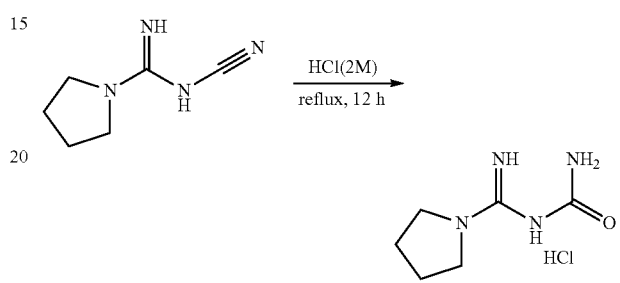

N1-pyrolidine cyanoguanide (300 mg, 2.17 mmol) was added by 2N HCl solution (6 ml) and agitated with reflux for 3 hours. The reaction product was added by 20 ml of ethylacetate and filtered. The obtained solid was washed with ethylacetate and dried under vacuum to produce the title compound in white solid (230 mg, 55%).

1H NMR (600 MHz, MeOH) δ 3.55 (m, 4H), 2.07 (m, 4H); LC-MS m/z 157.2 [M+1]

Example 244

N-1-carbamoyl-N-3-dimethyl guanide hydrochloride

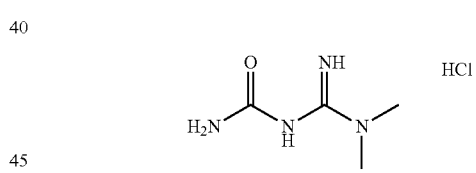

The title compound in white solid (280 mg, 88.6%) was obtained according to the same method of Example 243, except that NN-dimethyl cyanamide was used instead of N1-pyrolidine cyanoguanide 1H NMR (600 MHz, MeOH) δ 3.15 (s, 6H); LC-MS m/z 131.2 [M+1]

Example 245

N-phenylcarbamoyl-1-carboxyimidamide hydrochloride

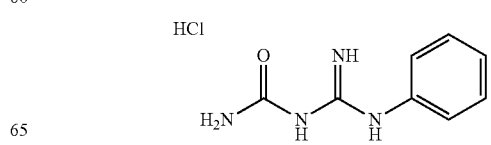

The title compound in white solid (300 mg, 74.6%) was obtained according to the same method of Example 243, except that N1-phenyl cyanoguanide was used instead of N1-pyrolidine cyanoguanide.

1H NMR (600 MHz, DMSO) δ 10.90 (bs, 1H), 10.33 (bs, 1H), 9.01 (bs, 1H), 8.48 (bs, 1H), 7.49 (d, J=7.6 Hz, 2H), 7.39 (m, 5H); LC-MS m/z 179.0 [M+1]

Example 246

N-1-butyl-N-3-carbamoyl guanide hydrochloride

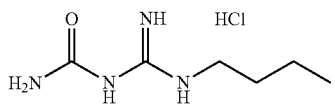

The title compound in white solid (40 mg, 17.8%) was obtained according to the same method of Example 243, except that N1-butyl cyanamide was used instead of N1-pyrolidine cyanamide.

1H NMR (600 MHz, CD3OD) δ 7.38 (d, J=7.8 Hz, 2H), 7.23 (d, J=7.8 Hz, 2H), 2.98 (bs, 6H); C-MS m/z 159.2 [M+1]

Example 247

N-1-phenethyl-N-3-carbamoyl guanide hydrochloride

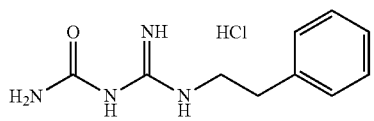 [SMILES: N=C(NCCc1ccccc1)NC(N)=O ; Cl]

The title compound in white solid (10 mg, 4%) was obtained according to the same method of Example 243, except that N1-phenethyl cyanamide was used instead of N1-pyrolidine cyanamide.

1H NMR (600 MHz, CD3OD) δ 7.38 (d, J=7.8 Hz, 2H), 7.23 (d, J=7.8 Hz, 2H), 2.98 (bs, 6H); LC-MS m/z 207.1 [M+1]

Example 248

N-1-imidamidyl-N-3-phenyl urea hydrochloride

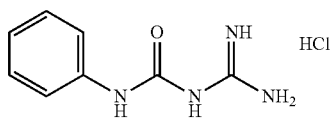 [SMILES: N=C(N)NC(=O)Nc1ccccc1 ; Cl]

1,3-bis(tert-butoxy-carbonyl)guanide was dissolved in acetonitrile and added by 1 to 2 equivalents of ethylamine. The mixture was agitated at room temperature for 30 minutes, and added by 1 equivalent of phenylcarbonylchloride. After 2 hours, the solvent was removed by vacuum distillation, dissolved in 1N HCl (10 ml) and agitated for 1 hour. The solvent was removed by vacuum distillation, agitated with the addition of ethylacetate 20 ml for 30 minutes, and the produced solid was filtered to produce the title compound in white solid (30 mg, 42%).

1H NMR (600 MHz, CD3OD) δ 7.45 (d, J=7.6 Hz, 2H), 7.31 (t, J=7.6 Hz, 2H), 7.08 (t, J=7.6 Hz, 1H); LC-MS m/z 179.0 [M+1]

Example 249

N-(imino(pyrolidin-1-yl)methyl)pyrolidine-1-carboxyamide

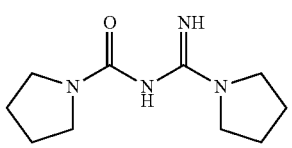 [SMILES: N=C(NC(=O)N1CCCC1)N1CCCC1]

The title compound in white solid (84 mg, 42%) was obtained according to the same method of Example 248, except that pyrolidine-1-carboxyimidamide was used instead of 1,3-bis(tert-butoxy-carbonyl)guanide, and pyrolidine-1-carbonyl chloride was used instead of phenylcarbonyl chloride.

1H NMR (600 MHz, CD3OD) δ 3.34 (m, 2H), 1.89 (m, 2H); LC-MS m/z 211.2 [M+1]

Example 250

N-(phenylcarbamoyl)pyrolidine-1-carboxyimidamide

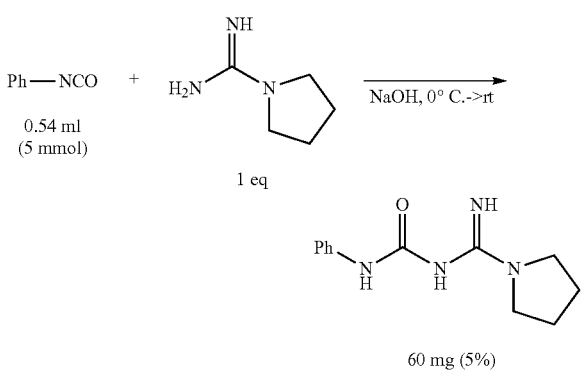

Pyrrolidine-1-carboximidamide (565 mg, 5 mmol) was added by 2N sodium hydroxide solution (1 0 ml) and then was slowly added by phenyl isocyanate (0.54 ml, 5 mmol) at 0° C. Then, the mixture was agitated for 18 hours at room temperature. The reaction product was concentrated under vacuum and purified with chromatograph using MC:MeOH=9:1 to produce the title compound in white solid (60 mg, 5%).

1H NMR (400 MHz, DMSO) δ 8.43 (bs, 1H), 7.57 (d, J=7.6 Hz, 2H), 7.16 (t, J=7.6 Hz, 2H), 6.82 (t, J=7.6 Hz, 1H), 3.35 (m, 4H), 1.83 (m, 4H); LC-MS m/z 233.1 [M+1]

Example 251

N-(phenylcarbamoyl)pyrolidine-1-carboxyimidamide hydrochloride

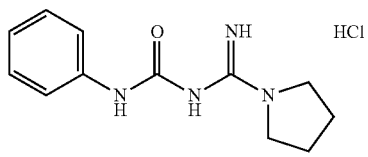 [SMILES: N=C(NC(=O)Nc1ccccc1)N1CCCC1 ; Cl]

The compound obtained in Example 250 (30 mg, 0.13 mmol) was dissolved in 10 ml of methanol, and agitated with the addition of concentrate HCl 0.5 ml for 1 hour at room temperature. The reaction product was agitated with the add-on of ethylacetate 20 ml for 30 minutes and the solid was filtered. The solid was washed with ethylacetate and dried under vacuum to produce the title compound in white solid (21 mg, 62%).

1H NMR (400 MHz, DMSO) δ 10.90 (m, 1H), 10.24 (m, 1H), 8.88 (m, 1H), 7.47 (d, J=7.6 Hz, 2H), 7.35 (t, J=7.6 Hz, 2H), 7.11 (t, J=7.6 Hz, 1H), 3.64 (m, 2H), 3.42 (m, 2H), 1.95 (m, 4H); LC-MS m/z 233.1 [M+1]

Example 252

N-(imidamidyl)-N-(4-fluoro)phenethyl urea hydrochloride

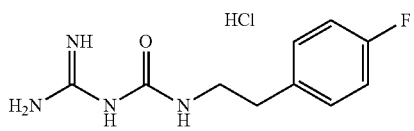 [SMILES: Cl ; N=C(N)NC(=O)NCCc1ccc(F)cc1]

The title compound in white solid (8 mg, 11%) was obtained according to the same method of Example 229, except that 1,3-Bis(tert-butoxycarbonyl)guanidine was used instead of thiazole-2-amine, and 4-fluorophenethyl isocyanate was used instead of phenethyl isocyanate.

1H NMR (600 MHz, CD3OD) δ 7.23 (m, 2H), 7.00 (m, 2H), 3.32 (m, 2H), 2.77 (m, 2H) LCMS: 225.1 [M+H]+

Example 253

N-(4-fluorobenzyl)-4,5-dihydro-1H-imidazole-2-amine hydrochloride

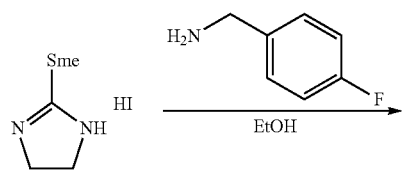

2-(methylthio)-4,5-dihydro-1H-imidazole hydroiodide (0.1 g, 0.41 mmol) was dissolved in ethanol (4 mL) at room temperature, and agitated by reflux with the addition of (4-fluorophenyl)methanamine (0.047 ml, 0.41 mmol) at 90° C. for 18 hours. After the reaction completed, the product was concentrated under vacuum and purified with chromatograph using MC:MeOH=9:1. The purified product was dissolved in a small amount of methylol and agitated with the addition of 1 equivalent of 12N HCl at room temperature to produce the title compound in white solid (45 mg, 45%).

1H NMR (600 MHz, CD3OD) δ 7.37 (m, 2H), 7.14 (m, 2H), 4.39 (s, 2H), 3.74 (s, 4H) LCMS: 194.1 [M+H]+

Example 254

N-(4-fluorophenethyl)-4,5-dihydro-1H-imidazole-2-amine hydrochloride

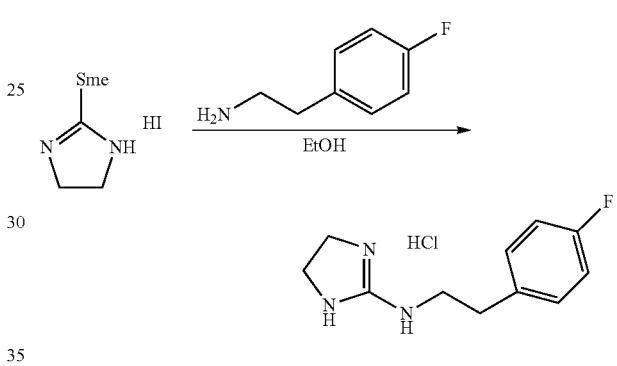

2-(methylthio)-4,5-dihydro-1H-imidazole hydroiodide (0.1 g, 0.41 mmol) was dissolved in ethanol (4 mL) at room temperature and agitated by reflux with the addition of (4-fluorophenyl)ethanamine (0.053 ml, 0.41 mmol) at 90° C. for 18 hours. After the reaction completed, the product was concentrated under vacuum and purified with chromatograph using MC:MeOH=9:1. The purified product was dissolved in a small amount of methylol and agitated with the addition of 1 equivalent of 12N HCl at a room temperature for 1 hour to produce the title compound in white solid (68 mg, 68%).

1H NMR (600 MHz, CD3OD) δ 7.28 (m, 2H), 7.04 (m, 2H), 3.66 (s, 4H), 3.44 (t, J=6.6 Hz, 2H), 2.87 (t, J=6.6 Hz, 2H) LCMS: 208.1 [M+H]+

Example 255

N-1-phenethyl-N-5-acetylbiguanide hydrochloride

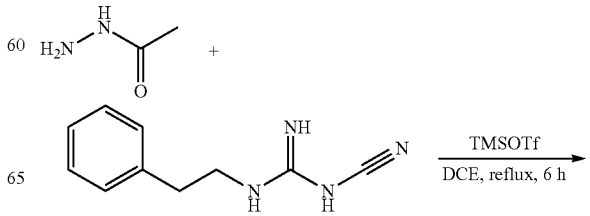

-continued

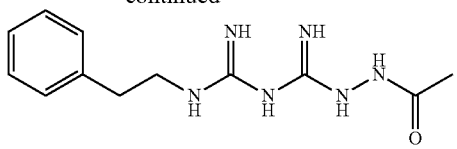

Acetohydrazide (0.1 g, 1.35 mmol) was dissolved in dichloromethane (10 mL) and was agitated with the addition of trimethylsilyl trifluoromethane sulphonate (0.24 ml, 1.35 mmol) at room temperature for 30 minutes. The reaction solution was added by the compound of Example 2 (0.25 g, 1.35 mmol) and was agitated by reflux at 80° C. for 6 hours. After the reaction completed, the reaction product was maintained at room temperature and agitated for 1 hour by the addition of 12N HCl (0.16 ml, 1.91 mmol). The produced solid was filtered and washed with dichloromethane 10 ml, and was dissolved completely in a small amount of ethanol and agitated with the addition of ethylacetate 10 ml at room temperature for 1 hour. The produced solid was filtered, washed with ethylacetate 10 ml and dried under vacuum to produce the title compound in white solid (170 mg, 48%).

1H NMR (600 MHz, CD3OD) δ 7.30 (t, J=7.2 Hz, 2H), 7.25 (d, J=7.2 Hz, 2H), 7.21 (t, J=7.2 Hz, 1H), 3.48 (t, J=7.2 Hz, 2H), 2.86 (t, J=7.2 Hz, 2H), 2.02 (s, 3H) LCMS: 263.2 [M+H]+

Example 256

1-(2,3-dihydro-1H-inden-2-yl)biguanide hydrochloride

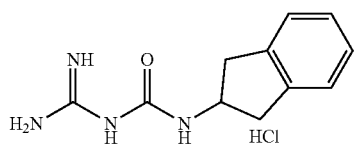 [SMILES: N=C(N)NC(=O)NC1Cc2ccccc2C1 ; Cl]

The title compound in white solid (90 mg, 30%) was obtained according to the same method of Example 1, except that 2-aminoindan was used instead of 3,4-dichloro phenethylamine.

1H NMR (600 MHz, DMSO) δ 7.25 (m, 2H), 7.17 (m, 2H), 4.40 (m, 1H), 3.26 (bs, 2H), 2.88 (bs, 2H) LCMS: 218 (M+H+)

Example 257

N-carbamimidoylisoindoline-2-carboximidamide hydrochloride

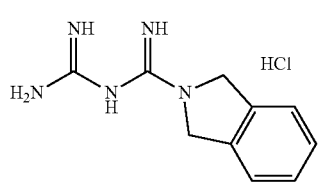 [SMILES: N=C(N)NC(=N)N1Cc2ccccc2C1 ; Cl]

The title compound in white solid (562 mg, 78.9%) was obtained according to the same method of Example 1, except that isoindoline was used instead of 3,4-dichloro phenethylamine.

1H NMR (400 MHz, DMSO) δ 8.16 (s, 1H), 7.26 (m, 2H), 7.17 (m, 2H), 4.33 (m, 1H), 3.28 (m, 2H), 2.82 (m, 2H) LCMS: 176 (M+H+)

Test Example 1

Test for Inhibition of OCR and Enhancement of ECAR

A549 cells were purchased from American Type Tissue Culture Collection (CCL-2) and cultured in RPMI 1640 supplied with 10% fetal bovine serum (FBS) and antibiotic-antimycotic (Lifetech, CA). A549 cells were separated with 0.5% Trypsin-EDTA and 3,000 cells were plated on 1 mg/ml poly-D-lysine (Sigma, P6407) coated XF 96 well culture media. A549 cells were allowed to adhere to the wells for 24 hours under the condition of temperature, 37° C. and 5% $CO_2$ The sensor cartridge of XF Analyzer was soaked in 200 Ad of Calibrant solution (Seahorse, MA) in a clear 96-well plate at 37° C. for 24 hours. The compounds of the present invention were diluted with RPMI 1640 without FBS, transferred to A549 cells on XF 96 well plate, and incubated further for 23 hours at 37° C. and 5% $CO_2$. After incubation, the compound solution was exchanged with pre-warmed and pH adjusted (pH7.4) XF assay media (Seahorse) supplied with 15 mM D-glucose (Sigma), 15 mM sodium pyruvate (Lifetechnologies, CA) and 4 mM L-glutamine (Lifetechnologies, CA). The compounds of present invention were prepared in XF Assay media and added to the assay plate. The assay plate was equilibrated in XF Analyzer for 1 hour, and the reading were started by sensor cartridge. The cytotoxicity assay was followed using Cyquant (Lifetechnologies, CA) in order to calibrate the inhibition with cytotoxicity of compounds. The concentrations of the compounds were tested at 0, 0.5, 1, 5, 10 and 2 μM and IC50 value was obtained from the inhibited values. That is, from OCR inhibition values at each concentration of the compound, IC50 was calculated according to Prism's dose response curve fitting.

In Table 1, the levels of OCR IC50 are evaluated by the following.
A Level: IC50<2 uM
B Level: IC50=2~5 uM
C Level: IC50>5 uM According to the test results of the compounds, the compounds were classified into A, B and C. The test results are summarized in Table 1. The test compounds had good OCR inhibitory effect, which suggested the excellent OXPHOX inhibitor. The most compounds having an OCR inhibitory activity showed the increased ECAR.

TABLE 1

| Example No. | OCR IC50 (A549, 24 hrs) | ECAR Enhancement (A549, 24 hrs) |
|---|---|---|
| 1 | C | No test |
| 3 | A | + |
| 4 | B | + |
| 8 | B | No test |
| 9 | C | No test |
| 10 | C | No test |
| 14 | C | No test |
| 16 | B | + |

TABLE 1-continued

| Example No. | OCR IC50 (A549, 24 hrs) | ECAR Enhancement (A549, 24 hrs) |
|---|---|---|
| 17 | B | + |
| 18 | C | + |
| 22 | A | + |
| 26 | A | No test |
| 27 | B | + |
| 28 | B | + |
| 30 | C | + |
| 31 | C | + |
| 32 | C | + |
| 37 | C | + |
| 41 | C | + |
| 44 | B | + |
| 45 | B | No test |
| 47 | C | + |
| 48 | A | + |
| 49 | C | + |
| 50 | B | + |
| 52 | C | + |
| 56 | C | + |
| 61 | B | + |
| 66 | B | + |
| 68 | B | No test |
| 70 | B | No test |
| 71 | C | No test |
| 72 | C | No test |
| 73 | B | No test |
| 74 | A | No test |
| 75 | A | No test |
| 76 | B | No test |
| 77 | B | No test |
| 78 | A | No test |
| 79 | A | No test |
| 80 | A | No test |
| 81 | A | No test |
| 122 | C | No test |
| 126 | C | No test |
| 127 | C | No test |
| 128 | C | No test |
| 133 | A | + |
| 137 | B | + |
| 138 | B | + |
| 140 | B | + |
| 151 | C | + |
| 153 | C | + |
| 155 | A | + |
| 161 | B | + |
| 165 | B | + |
| 169 | C | + |
| 174 | C | + |
| 175 | C | + |
| 178 | C | + |
| 182 | B | + |
| 183 | A | + |
| 184 | C | + |
| 185 | C | + |
| 187 | C | + |
| 188 | C | + |
| 190 | B | + |
| 192 | B | + |
| 195 | B | + |
| 197 | B | + |
| 198 | B | + |
| 199 | C | + |
| 200 | B | + |
| 203 | B | + |
| 204 | B | + |
| 205 | B | + |
| 206 | A | No test |
| 207 | C | No test |
| ** | ** | ** |

Test Example 2

Cytotoxicity in Low Glucose Condition

SK-MEL-28 (HTB-72) is a melanoma cell line obtained from ATCC (MA) and cultured in RPMI 1640 media (Lifetechnologies, CA) with supplement of 10% FBS and antibiotic-antimycotic (Lifetechnologies, CA). RPMI 1640 (-Glucose) was used to prepare low glucose media and 0.75 mM glucose was supplied with D-(+)-glucose solution from Sigma. SK-MEL-28 cells were separated from culture plate using 0.5% trypsin-EDTA and 5,000 cells were plated in 96-well plate with low glucose media. After incubation at 37° C. for 24 hour, 5% $CO_2$, the cells were treated with the compounds of present invention in FBS-free media for 72 hours. The cytotoxicity was measured by the MTT (AM-RESCO, OH) assay. NADH-dependent cellular oxidoreductase reduces MTT to its insoluble tetrazolium with purple color. The enzyme depends on cell number or energy state of cells. 10 μl of 5 mg/ml MIT solution was added to each well of the assay plate and skip the well for blank. The plate was incubated at 37° C. and 5% $CO_2$ for 2 hours. The MTT solution was removed from each well and 100 μl of DMSO was added. The plate was read by VICTOR X3 Multilabel Counter at the wavelength of 550 nm. In Table 2, the levels of IC50 are evaluated by the following criteria.

A Level: IC50<5 uM
B Level: IC50=5~10 uM
C Level: IC50>10 uM

According to the concentration of compound for killing the half of cell populations (the levels of IC50), the compounds were classified into A, B and C, when the compounds were treated on SK-MEL-28 cells at 0.75 mM glucose. The test result is summarized in Table 2. The test compounds have good cell death effect at a low concentration, and thus are suggested to show excellent anti-cancer activity.

TABLE 2

| Example No. | SK-MEL-28 0.75 mM glucose Cell viability (IC50 ia |
|---|---|
| 1 | B |
| 3 | B |
| 17 | C |
| 18 | C |
| 22 | C |
| 26 | A |
| 30 | A |
| 37 | B |
| 44 | A |
| 48 | C |
| 49 | C |
| 50 | A |
| 52 | B |
| 61 | A |
| 66 | A |
| 68 | B |
| 70 | A |
| 71 | C |
| 72 | B |
| 74 | A |
| 75 | A |
| 76 | A |
| ** | ** |
| 77 | B |
| 78 | A |
| 79 | B |
| 80 | C |
| 81 | B |
| 122 | B |

TABLE 2-continued

| Example No. | SK-MEL-28 0.75 mM glucose Cell viability (IC50 ia |
|---|---|
| 124 | C |
| 126 | A |
| 128 | A |
| 129 | C |
| 130 | C |
| 132 | C |
| 133 | B |
| 153 | C |
| 161 | C |
| 169 | C |
| 182 | B |
| 183 | A |
| 195 | A |
| 197 | C |
| 199 | C |
| 204 | C |
| 205 | C |

Test Example 3

In Vitro Combination Study

A549, H1975 (CRL5908, ATCC) or U937 cell (CRL1593.2™, ATCC) lines were cultured in RPMI 1640 media (Lifetechnologies, CA) with supplement of 10% FBS and antibiotic-antimycotic (Lifetechnologies, CA). Dasatinib (Combi-Blocks, San Diego, Calif.) is Bcr-Abl-tyrosine kinase inhibitor and Src family tyrosine kinase inhibitor approved for CML treatment. GDC094 (Selleckchem, Houston, Tex.) is a pan-PI3K inhibitor and effective in various cancer cells. H1975 or A549 cells were dissociated from culture plate using 0.5% trypsin-EDTA (Lifetechnologies, CA) and were suspended. U937 cells were spun down using centrifugation. A549 cells were seeded at a density of 3,000 cells/well and H1975 or U937 cells were seeded at a density of 5,000 cells/well in a 96-well plate, and were allowed to adhere at 37° C. and 5% $CO_2$ for 24 hours. $IC_{50}$ of each compounds were obtained from each cell line prior to the combination therapy test.

Among four concentrations of the compounds of present invention, the highest concentration was set to $IC_{80}$ and the lowest concentration was approximately $IC_{30}$. The concentrations of other anticancer drug were ranged from $IC_{50}$ to $IC_{30}$. The media in 96-well plate were exchanged with the prepared compound solution. To determine cell viability, except U937 cells, 10 μl of 5 mg/ml MTT in D-PBS (Lifetechnologies, CA) were added to each well after 72-hour treatment and plates were incubated at 37° C. and 5% CO2 for 2 hours. 100 μl of DMSO was added after removing MTT solution from each well, and were read by VICTOR X3 Multilabel Counter at the wavelength of 550 nm.

For the analysis of U937 cell viability, 20 μl of Cellti-ter96® AQueous one solution (MTS, Promega, Madison, Wis.) were added to each well, and plates were incubated at 37° C. and 5% CO2. After 2 hours later, plates read by VICTOR X3 Multilabel Counter at the wavelength of 490 nm. The combination index (CI value) was calculated using Calcusyn (Biosoft, UK). According to the Combination index analysis, the index having lower than 1 shows synergistic effect, and the index having 1 shows antagonism effect. The test results are shown in FIGS. 1 to 5.

The combination therapy of compound of Example 1 and Dasatinib were tested on 549 cells. Specifically, when 0.05 μM of Dasatinib and the compound of Example 1 were treated in combination, CI value was 0.289, which showed the high synergistic effect. When 0.05 μM of Dasatinib and 8 μM of Phenformin were treated in combination, they did not show the synergic effect. That is, compared to the test result of Phenformin and Dasatinib treated on A549 cells, the compound of Example 1 showed higher synergic effect (FIG. 1). FIG. 1 shows the treatment effect of the Compound of Example 1 in combination with Dasatinib on A549 cell.

In addition, the compounds of Examples 1, and 104 were tested on H1975 cell in combination with Dasatinib. When 0.2 μM of Dasatinib and 8 μM or 40 μM of the compound of Example 1 were treated, and when 0.2 μM of Dasatinib and 8 μM, 40 μM or 200 μM of the compound of Example 104 were treated, they showed low combination therapy effect (FIGS. 4 and 5) FIG. 4 shows the treatment effect of the Compound of Example 1 in combination with Dasatinib on H1975 cell. FIG. 5 shows the treatment effect of the Compound of Example 104 in combination with Dasatinib on H1975 cell.

When the compound of Example 1 was sued with GDC0941 on U937 cell and A549 cell, it showed CI value of lower than 1. Compared to the effect of Phenformin, the compound of Example 1 showed the same effect as that of Phenformin, when the compound of Example 1 was treated at an tenth concentration of Phenformin on U937 cell and half concentration of Phenformin on A549 cell. That is, when the compound of Example 1 is used in combination with GDC0941, it represented higher synergic effect on U937 cell and A549 cell than Phenformin (FIGS. 2 and 3). FIG. 2 shows the treatment effect of the Compound of Example 1 in combination with GDC0941 on U937 cell. FIG. 3 shows the treatment effect of the Compound of Example 1 in combination with GDC0941 on A549 cell.

Test Example 4

In Vivo Testing OXPHOS Inhibitors for Anticancer Activity

The SK-MEL-239 tumor cell line was maintained in vitro as monolayer in RPMII 640 medium supplemented with 10% heat inactivated fetal bovine serum, 100 U/ml penicillin and 100 μg/ml streptomycin, and L-glutamine (2 mM) at 37° C. in an atmosphere of 5% $CO_2$ in air. The tumor cells were routinely subcultured twice weekly with 0.5% trypsin-EDTA treatment. The cells growing in an exponential growth phase were harvested and counted for tumor cell inoculation.

Female BALB/c nude mice aged 6-8 weeks and weighing approximately 18-22 g were purchased from Vital River. Each mouse was inoculated subcutaneously at the right flank with SK-MEL-239 tumor cells ($1\times10^7$) in 0.1 ml of PBS for tumor development. The treatment was started, when the tumor size reaches approximately 100 mm³. 100 mg/kg of Phenformin and 15 mg/kg of Vemurafenib were administered via oral gavage twice daily and 100 mg/kg HLPOI (HL176001001) was administered once daily for 21 days. Tumor volumes were measured twice a week in two dimensions using a caliper, and the volume was expressed in mm³ using the formula: $V=0.5 \times a \times b^2$, where a and b were the long and short diameters of the tumor, respectively. The T/C value (in percentage) was an indication of antitumor effect. T and C were the mean volumes of the treated and control groups, respectively. The test results are shown in FIG. 6 and Table 3. FIG. 6 shows the treatment effect of the Compound of Example 1 or Phenformin on Vemurafenib in xenocraft model using SK-MEL-239 cell.

TABLE 3

| Treatment | Dosing (mg/kg) | Tumor Volume (Day 28, mm$^3$, a) | T/C (Day 28, %) | P value, b |
|---|---|---|---|---|
| G1: Vehicle control | — | 2,944 ± 289 | — | — |
| G2: Phenformin | 150/100 | 1,562 ± 166 | 52.2 | 0.017 |
| G3: Vemurafenib | 15 | 1,144 ± 101 | 38.0 | 0.002 |
| G4: Example No. 1 | 100 | 1,869 ± 82 | 65.4 | 0.071 |
| G5: Phenformin + Vemurafenib | 150/100 + 15 | 1,099 ± 103 | 38.2 | 0.001 |
| G6: Example No. 1 + Vemurafenib | 50 + 15 | 868 ± 81 | 30.0 | 0.001 |
| G7: Example No. 1 + Vemurafnib | 100 + 15 | 785 ± 161 | 25.5 | <0.001 |

As a test result, when each Phenformin and the compound of Exmple 1 was treated at a concentration of 100 mg/kg, they showed the significant reduction of tumor volume, compared to the control group. Phenformin was administrated at a dosage of 100 mg/kg twice daily. However, the compound of Example 1 was administered at a dosage of 100 mg/kg once daily, which means the smaller amount of Example 1 compound used for achieving the same effect of Phenformin. Also, when the compound of Example 1 was treated in combination with 15 mg/kg of Vemurafenib, the combined treatment reduced the tumor volume, compared to the single administration of Vemurafenib. However, the combined treatment of Phenformin and Vemurafenib did not show the significant reduction of tumor volume, compared to the single administration of Vemurafenib. Such result suggests that the compound of Example 1 in combination with Vemurafenib has more advantageous than Phenformin.

The invention claimed is:

1. A compound of chemical formula 1, or a pharmaceutically acceptable salt, or a pharmaceutically acceptable solvate thereof; wherein:

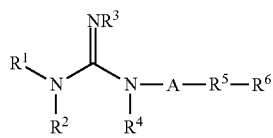

chemical formula 1 wherein R$^1$ is H,
R$^2$, R$^3$ and R$^4$ are H;
A is —C(NH)—NH—;
R$^5$ is —(CH$_2$)n- where n is an integer from 1 to 6,
R$^6$ is C$_8$-C$_9$ cycloalkyl, or 7 or 9-11-membered benzocycloalkyl, where cycloalkyl, and benzocycloalkyl may be substituted with at least one of hydroxyl, halogen, C$_1$-C$_4$ alkyl, C$_1$-C$_4$ haloalkyl, C$_3$-C$_7$ cycloalkyl, C$_6$-C$_9$ arylalkyl, SO$_2$NH$_2$, OR$^8$, or NR$^{10}$R$^{11}$, where each of R$^8$, R$^{10}$ and R$^{11}$ is, independently, hydrogen, C$_1$-C$_4$ alkyl, C$_1$-C$_4$ haloalkyl, or C$_6$-C$_{12}$ aryl; or
R$^6$ is C$_{10}$ cycloalkyl, or 7-membered heterocycloalkyl, where C$_{10}$ cycloalkyl and 7-membered heterocycloalkyl are substituted with at least one of hydroxyl, halogen, C$_1$-C$_4$alkyl, C$_1$-C$_4$ haloalkyl, C$_3$-C$_7$ cycloalkyl, C$_6$-C$_9$ arylalkyl, SO$_2$NH$_2$, OR$^8$, or NR$^{10}$R$^{11}$, where each of R$^8$, R$^{10}$, and R$^{11}$ is, independently, hydrogen, C$_1$-C$_4$ alkyl, C$_1$-C$_4$ haloalkyl, or C$_6$-C$_{12}$ aryl.

2. The compound of claim 1, wherein the compound having chemical formula 1 is a guanidine compound having chemical formula 2, or a pharmaceutically acceptable salt, or a pharmaceutically acceptable solvate thereof:

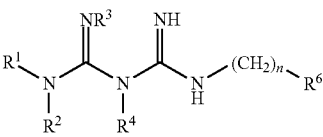

chemical formula 2 wherein R$^1$ is H,
R$^2$, R$^3$, and R$^4$ are H;
n is an integer from 1 to 6, and
R$^6$ is 7 or 9-11-membered benzocycloalkyl, where benzocycloalkyl may be substituted with at least one hydroxyl, halogen, C$_1$-C$_4$ alkyl, C$_1$-C$_4$ haloalkyl, C$_3$-C$_7$ cycloalkyl, C$_5$-C$_9$ arylalkyl, SO$_2$NH$_2$, OR$^8$, or NR$^{10}$R$^{11}$, where each of R$^8$, R$^{10}$ and R$^{11}$ is, independently, hydrogen, C$_1$-C$_4$ alkyl, C$_1$-C$_4$ haloalkyl, or C$_6$-C$_{12}$ aryl; or
R$^6$ is 7-membered heterocycloalkyl substituted with at least one of hydroxyl, halogen, C$_1$-C$_4$ alkyl, C$_1$-C$_4$ haloalkyl, C$_3$-C$_7$ cycloalkyl, C$_6$-C$_9$ arylalkyl, SO$_2$NH$_2$, OR$^8$, or NR$^{10}$R$^{11}$, where each of R$^8$, R$^{10}$, and R$^{11}$ is, independently, hydrogen, C$_1$-C$_4$ alkyl, C$_1$-C$_4$ haloalkyl, or C$_6$-C$_{12}$ aryl.

3. A compound of chemical formula 3, or a pharmaceutically acceptable salt, or a pharmaceutically acceptable solvate thereof:

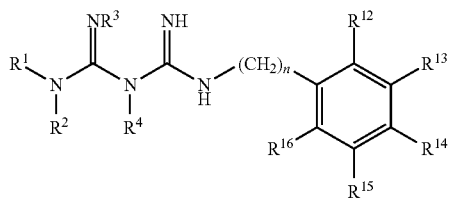

chemical formula 3 wherein R$^1$ is H,
R$^2$, R$^3$, and R$^4$ are H,
n is an integer from 1 to 6, and
an adjacent pair of R$^{12}$, R$^{13}$, R$^{14}$, R$^{15}$, or R$^{16}$ are C$_1$-C$_4$ alkyl groups that, together with the atoms to which they are attached, combine with each other to form a 4 to 7 membered saturated or unsaturated cycloalkyl group; and
the variables R$^{12}$, R$^{13}$, R$^{14}$, R$^{15}$, and R$^{16}$ that are not part of the adjacent pair that combine with each other to form a 4 to 7 membered saturated or unsaturated cycloalkyl group are hydrogen.

4. A compound selected from the group consisting of the following compounds, or a pharmaceutically acceptable salt thereof:
N-1-(3,4-dichloro)phenethylbiguanide,
N-1-(2,5-dichloro)phenethylbiguanide,
N-1-(2-chloro)phenethylbiguanide,
N-1-(3-methoxy)phenethylbiguanide,
N-1-(2-(5,6,7,8-tetrahydronaphthalen-1-yl)ethyl)biguanide, N-1-(2-(5,6,7,8-tetrahydronaphthalen-2-yl)ethyl)biguanide,
N-1-(2-(5,6,7,8-tetrahydronaphthalen-2-yl)methyl)biguanide, and
N-1-(2-(2,3-dihydro-1H-inden-5-yl)ethyl)biguanide.

5. A compound selected from the group consisting of:
N-1-(2-(2,3-dihydro-1H-inden-5-yl)ethyl)biguanide,
N-1-(2-(5,6,7,8-tetrahydronaphthalen-2-yl)ethyl)biguanide, and
N-1-(2-(5,6,7,8-tetrahydronaphthalen-2-yl)methyl)biguanide, or
a pharmaceutically acceptable salt thereof.

6. A compound selected from the group consisting of the following compounds, or a pharmaceutically acceptable salt thereof:
1-(4-trifluoromethoxyphenethyl)guanide, and
1-(1-(5,6,7,8-tetrahydronaphthalen-1-yl)ethyl)guanide.

\* \* \* \* \*